US007198927B2

(12) United States Patent
DiCosimo et al.

(10) Patent No.: US 7,198,927 B2
(45) Date of Patent: Apr. 3, 2007

(54) ENZYMATIC PRODUCTION OF GLYCOLIC ACID

(75) Inventors: Robert DiCosimo, Chadds Ford, PA (US); Mark S. Payne, Wilmington, DE (US); Anna Panova, Hockessin, DE (US); Jeffrey Thompson, Wilmington, DE (US); Daniel P. O'Keefe, Ridley Park, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/313,541

(22) Filed: Dec. 21, 2005

(65) Prior Publication Data

US 2006/0160199 A1 Jul. 20, 2006

Related U.S. Application Data

(60) Provisional application No. 60/638,176, filed on Dec. 22, 2004, provisional application No. 60/638,127, filed on Dec. 22, 2004.

(51) Int. Cl.
*C12P 7/42* (2006.01)
*C12P 7/40* (2006.01)
*C12N 9/80* (2006.01)
*C12N 15/74* (2006.01)

(52) U.S. Cl. ............... 435/146; 435/228; 435/69.1; 435/252.2; 435/136; 536/23.2

(58) Field of Classification Search .................. None
See application file for complete search history.

(56) References Cited

U.S. PATENT DOCUMENTS

| | | | |
|---|---|---|---|
| 3,940,316 | A | 2/1976 | Commeyras et al. |
| 5,223,416 | A | 6/1993 | Endo et al. |
| 5,234,826 | A | 8/1993 | Yamagami et al. |
| 5,296,373 | A | 3/1994 | Endo et al. |
| 5,326,702 | A | 7/1994 | Endo et al. |
| 5,508,181 | A | 4/1996 | Hashimoto |
| 5,605,793 | A | 2/1997 | Stemmer |
| 5,756,306 | A | 5/1998 | Yamaguchi et al. |
| 5,811,238 | A | 9/1998 | Stemmer et al. |
| 5,814,508 | A | 9/1998 | Di Cosimo et al. |
| 5,830,721 | A | 11/1998 | Stemmer et al. |
| 5,837,458 | A | 11/1998 | Minshull et al. |
| 6,037,155 | A | 3/2000 | Kobayashi et al. |
| 6,291,708 | B1 | 9/2001 | Cockrem |
| 6,383,786 | B1 | 5/2002 | Chauhan et al. |
| 6,416,980 | B1 | 7/2002 | Chauhan et al. |
| 6,870,038 | B2 | 3/2005 | Chauhan et al. |
| 2004/0138409 | A1 | 7/2004 | Hayashi et al. |
| 2004/0210087 | A1 | 10/2004 | Meng et al. |

FOREIGN PATENT DOCUMENTS

| | | |
|---|---|---|
| EP | 0 610 048 B1 | 8/1994 |
| EP | 0 610 049 B1 | 8/1994 |
| JP | 6-156086 | 6/1994 |
| JP | 9-28390 | 2/1997 |
| WO | WO 01/75077 A2 | 10/2001 |
| WO | WO 2005/106005 A1 | 11/2005 |

OTHER PUBLICATIONS

Kailas L. Wasewar et al., Reactive Extraction of Lactic Acid Using Alamine 336 in MIBK; Equilibria and Kinetics, Journal of Biotechnology, vol. 97:59-68, 2002.
Nikolay S. Outchkourov et al., Optimization of the Expression of Equistatin in *Pichia pastoris*, Protein Expression and Purification, vol. 24:18-24, 2002.
Alexandre Melnikov et al., Random Mutagenesis by Recombinational Capture of PCR Products in *Bacillus subtilis* and *Acinetobacter calcoaceticus*, Nucleic Acids Research, vol. 27(4):1056-1062, 1999.
IUPAC-IUB Joint Commission on Biochemical Nomenclature (JCBN), Nomenclature and Symbolism for Amino Acids and Peptides, Biochem. J., vol. 219:345-373, 1984.
National Center for Biotechnology Information General Identifier No. 20141090, Accession No. L09137, May 22, 2002, C. Yanisch-Perron et al., Improved M13 Phage Cloning Vectors and Host Strains: Nucleotide Sequences of the M13MP18 and PUC19 Vectors.
Janet A. Tamada et al., Extraction of Carboxylic Acids With Amine Extractants. 1. Equilibria and Law of Mass Action Modeling, Ind. Eng. Chem. Res., vol. 29:1319-1326, 1990.
Ismail Inci et al., Extraction of Glycolic Acid From Aqueous Solutions by Trioctyl Methylammonium Chloride and Organic Solvents, J. Chem. Eng. Data, vol. 50:536-540, 2005.
Janet A. Tamada et al., Extraction of Carboxylic Acids With Amine Extractants. 2. Chemical Interactions and Interpretation of Data, Ind. Eng. Chem. Res., vol. 29:1327-1333, 1990.
Mukund V. Deshpande, Ethanol Production From Cellulose by Coupled Saccharification/Fermentation Using *Saccharomyces cerevisiae* and Cellulase Complex From *Sclerotium rolfsii* UV-8 Mutant*, Applied Biochemistry and Biotechnology, vol. 36:227-234, 1992.
D. Tourneix, A. et al., Regulation of Nitrile-Hydratase Synthesis in a *Brevibacterium* Species, Antonie Van Leeuwenhoek, vol. 52:173-182, 1986.
Yasuhisa Asano et al., Aliphatic Nitrile Hydratase From *Arthrobacter* Sp. J-1 Purification and Characterization, Agric. Biol. Chem., vol. 46(5):1165-1174, 1982.

(Continued)

*Primary Examiner*—Tekchand Saidha
*Assistant Examiner*—Md. Younus Meah

(57) ABSTRACT

Various methods are provided for the enzymatic production of glycolic acid from glycolonitrile. These methods include: 1) use of *Acidovorax facilis* 72W nitrilase mutants having improved nitrilase activity for converting glycolonitrile to glycolic acid, and 2) methods to improve catalyst stability and/or productivity. The methods to improve catalyst stability/productivity include use of reaction stabilizers, running the reactions under substantially oxygen free conditions, and controlling the concentration of substrate in the reaction mixture.

21 Claims, No Drawings

OTHER PUBLICATIONS

C. O'Reilly et al., The Nitrilase Family of CN Hydrolysing Enzymes—A Comparative Study, Journal of Applied Microbiology, vol. 95:1161-1174, 2003.

Don Cowan et al., Biochemistry and Biotechnology of Mesophilic and Thermophilic Nitrile Metabolizing Enzymes, Extremophiles, vol. 2:207-216, 1998.

Helen C. Pace et al., The Nitrilase Superfamily: Classification, Structure and Function, Genome Biology, vol. 2(1):Reviews 1-9, 2001.

I. Inci, Distribution of Glycolic Acid Between Water and Different Organic Solutions, Chem. Biochem. Eng. Q., vol. 16(2):81-85 2002.

David T. Mowry, The Preparation of Nitriles, Chemical Reviews, vol. 42:189-283, 1947.

S. Chauhan et al., Purification, Cloning, Sequencing and Over-Expression in *Escherichia coli* of a Regioselective Aliphatic Nitrilase From *Acidovorax facilis* 72W, Appl. Microbiol. Biotechnol., vol. 61:118-122, 2003.

Li Feng et al., High-Level Expression and Mutagenesis of Recombinant Human Phosphatidylcholine Transfer Protein Using a Synthetic Gene: Evidence for a C-Terminal Membrane Binding Domain, Biochemistry, vol. 39:15399-15409, 2000.

Michel Fromant et al., Direct Random Mutagenesis of Gene-Sized DNA Fragments Using Polymerase Chain Reaction, Analytical Biochemistry, vol. 224:347-353, 1995.

Lin-Goerke, PCR-Based Random Mutagenesis Using Manganese and Reduced DNTP Concentration, Biotechniques, vol. 23(3):409-412, 1997.

J. Peter Guthrie et al., Effect of the Acyl Substituent on the Equilibrium Constnat for Hydration of Esters, Canadian Journal of Chemistry, vol. 58(13):1281-1294, 1980.

SEQUENCE LISTING

<160> NUMBER OF SEQ ID NOS: 38

<210> SEQ ID NO 1
<211> LENGTH: 49
<212> TYPE: DNA
<213> ORGANISM: artificial sequence
<220> FEATURE:
<223> OTHER INFORMATION: Primer

<400> SEQUENCE: 1
cgactgcagt aaggaggaat aggacatggt ttcgtataac agcaagttc        49

<210> SEQ ID NO 2
<211> LENGTH: 40
<212> TYPE: DNA
<213> ORGANISM: artificial sequence
<220> FEATURE:
<223> OTHER INFORMATION: Primer

<400> SEQUENCE: 2
tgatctagag cttggagaat aaagggggaag accagagatg                 40

<210> SEQ ID NO 3
<211> LENGTH: 31
<212> TYPE: DNA
<213> ORGANISM: artificial sequence
<220> FEATURE:
<223> OTHER INFORMATION: Primer

<400> SEQUENCE: 3
gcgcatatgg tttcgtataa cagcaagttc c                           31

<210> SEQ ID NO 4
<211> LENGTH: 32
<212> TYPE: DNA
<213> ORGANISM: artificial sequence
<220> FEATURE:
<223> OTHER INFORMATION: Primer

<400> SEQUENCE: 4
ataggatcct tatggctact ttgctgggac cg                          32

<210> SEQ ID NO 5
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 5

-continued

| | |
|---|---|
| atg gtt tcg tat aac agc aag ttc ctc gcg gca acc gtt cag gca gag<br>Met Val Ser Tyr Asn Ser Lys Phe Leu Ala Ala Thr Val Gln Ala Glu<br>1               5                  10                  15 | 48 |
| ccg gta tgg ctc gac gca gac gca acg atc gac aag tcg atc ggc atc<br>Pro Val Trp Leu Asp Ala Asp Ala Thr Ile Asp Lys Ser Ile Gly Ile<br>        20                  25                  30 | 96 |
| atc gaa gaa gct gcc caa aag ggc gcg agt ctg atc gct ttc ccg gaa<br>Ile Glu Glu Ala Ala Gln Lys Gly Ala Ser Leu Ile Ala Phe Pro Glu<br>            35                  40                  45 | 144 |
| gta ttc att ccg ggc tac ccc tat tgg gcg tgg ctc ggc gac gtg aag<br>Val Phe Ile Pro Gly Tyr Pro Tyr Trp Ala Trp Leu Gly Asp Val Lys<br>    50                  55                  60 | 192 |
| tac agc cta agc ttt act tca cgc tat cac gag aat tcg ttg gag cta<br>Tyr Ser Leu Ser Phe Thr Ser Arg Tyr His Glu Asn Ser Leu Glu Leu<br>65                  70                  75                  80 | 240 |
| ggt gac gac cgt atg cgt cgc ctc cag ctg gcc gcg cgc cgc aac aaa<br>Gly Asp Asp Arg Met Arg Arg Leu Gln Leu Ala Ala Arg Arg Asn Lys<br>                85                  90                  95 | 288 |
| atc gca ctc gtc atg ggc tat tcg gag cgg gaa gcc gga tcg cgc tat<br>Ile Ala Leu Val Met Gly Tyr Ser Glu Arg Glu Ala Gly Ser Arg Tyr<br>            100                 105                 110 | 336 |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>        115                 120                 125 | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>    130                 135                 140 | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145                 150                 155                 160 | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>                165                 170                 175 | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>            180                 185                 190 | 576 |
| cct ctt cag ccg gat gtt ttc caa ctg agc atc gaa gcc aac gcg acg<br>Pro Leu Gln Pro Asp Val Phe Gln Leu Ser Ile Glu Ala Asn Ala Thr<br>        195                 200                 205 | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>    210                 215                 220 | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225                 230                 235                 240 | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>                245                 250                 255 | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>            260                 265                 270 | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>        275                 280                 285 | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>    290                 295                 300 | 912 |
| gtc cag ttc gac ccg cgc aat cat acg cca gtt cat cgc atc ggc att<br>Val Gln Phe Asp Pro Arg Asn His Thr Pro Val His Arg Ile Gly Ile<br>305                 310                 315                 320 | 960 |

-continued

```
gac ggt cgc ttg gat gtg aat acc cgc agt cgc gtg gag aat ttc cga      1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga      1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca      1104
Thr Lys Leu Phe Glu Gln Ser Leu Leu Ala Glu Glu Pro Val Pro Ala
    355                 360                 365 aag tag                                                              1110
Lys

<210> SEQ ID NO 6
<211> LENGTH: 369
<212> TYPE: PRT
<213> ORGANISM: Acidovorax facilis 72W

<400> SEQUENCE: 6

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
```

-continued

```
            290                 295                 300
Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
            355                 360                 365

Lys

<210> SEQ ID NO 7
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 7 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
                20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
            35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
        50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa cag agc atc gaa gcc aac gcg acg     624
Pro Leu Gln Pro Asp Val Phe Gln Gln Ser Ile Glu Ala Asn Ala Thr
        195                 200                 205
```

```
gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                              1110
Lys

<210> SEQ ID NO 8
<211> LENGTH: 369
<212> TYPE: PRT
<213> ORGANISM: Acidovorax facilis 72W

<400> SEQUENCE: 8

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
```

-continued

```
                145                 150                 155                 160
        Gly Leu Asn Cys Trp Glu His Phe Gln Pro Leu Ser Lys Phe Met Met
                        165                 170                 175
        Tyr Ser Leu Gly Glu Gln Val His Val Ala Ser Trp Pro Ala Met Ser
                    180                 185                 190
        Pro Leu Gln Pro Asp Val Phe Gln Gln Ser Ile Glu Ala Asn Ala Thr
                    195                 200                 205
        Val Thr Arg Ser Tyr Ala Ile Glu Gly Gln Thr Phe Val Leu Cys Ser
                    210                 215                 220
        Thr Gln Val Ile Gly Pro Ser Ala Ile Glu Thr Phe Cys Leu Asn Asp
        225                 230                 235                 240
        Glu Gln Arg Ala Leu Leu Pro Gln Gly Cys Gly Trp Ala Arg Ile Tyr
                        245                 250                 255
        Gly Pro Asp Gly Ser Glu Leu Ala Lys Pro Leu Ala Glu Asp Ala Glu
                    260                 265                 270
        Gly Ile Leu Tyr Ala Glu Ile Asp Leu Glu Gln Ile Leu Leu Ala Lys
                    275                 280                 285
        Ala Gly Ala Asp Pro Val Gly His Tyr Ser Arg Pro Asp Val Leu Ser
                    290                 295                 300
        Val Gln Phe Asp Pro Arg Asn His Thr Pro Val His Arg Ile Gly Ile
        305                 310                 315                 320
        Asp Gly Arg Leu Asp Val Asn Thr Arg Ser Arg Val Glu Asn Phe Arg
                        325                 330                 335
        Leu Arg Gln Ala Ala Glu Gln Glu Arg Gln Ala Ser Lys Arg Leu Gly
                    340                 345                 350
        Thr Lys Leu Phe Glu Gln Ser Leu Leu Ala Glu Glu Pro Val Pro Ala
                    355                 360                 365
        Lys

<210> SEQ ID NO 9
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 9 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
```

-continued

| | | | | | | | | | | | | | | |
|---|---|---|---|---|---|---|---|---|---|---|---|---|---|---|
| Ile | Ala | Leu | Val | Met | Gly | Tyr | Ser | Glu | Arg | Glu | Ala | Gly | Ser | Arg | Tyr |
| | | | 100 | | | | 105 | | | | 110 | | | | |

```
ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
            165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
        180                 185                 190 cct ctt cag ccg gat gtt ttc caa gct agc atc gaa gcc aac gcg acg     624
Pro Leu Gln Pro Asp Val Phe Gln Ala Ser Ile Glu Ala Asn Ala Thr
    195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
            245                 250                 255 ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
        260                 265                 270 ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
    275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att     960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
            325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
        340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
    355                 360                 365 aag tag                                                            1110
Lys

<210> SEQ ID NO 10
<211> LENGTH: 369
<212> TYPE: PRT
<213> ORGANISM: Acidovorax facilis 72W

<400> SEQUENCE: 10

Met Val Ser Tyr Asn Ser Lys Phe Leu Ala Ala Thr Val Gln Ala Glu
```

|   | 1 |   | 5 |   |   |   | 10 |   |   |   | 15 |   |
|---|---|---|---|---|---|---|---|---|---|---|---|---|

Pro Val Trp Leu Asp Ala Asp Ala Thr Ile Asp Lys Ser Ile Gly Ile
                20                      25                      30

Ile Glu Glu Ala Ala Gln Lys Gly Ala Ser Leu Ile Ala Phe Pro Glu
                35                      40                      45

Val Phe Ile Pro Gly Tyr Pro Tyr Trp Ala Trp Leu Gly Asp Val Lys
            50                      55                      60

Tyr Ser Leu Ser Phe Thr Ser Arg Tyr His Glu Asn Ser Leu Glu Leu
65                      70                      75                  80

Gly Asp Asp Arg Met Arg Arg Leu Gln Leu Ala Ala Arg Arg Asn Lys
                        85                      90                      95

Ile Ala Leu Val Met Gly Tyr Ser Glu Arg Glu Ala Gly Ser Arg Tyr
                    100                     105                     110

Leu Ser Gln Val Phe Ile Asp Glu Arg Gly Glu Ile Val Ala Asn Arg
                115                     120                     125

Arg Lys Leu Lys Pro Thr His Val Glu Arg Thr Ile Tyr Gly Glu Gly
        130                     135                     140

Asn Gly Thr Asp Phe Leu Thr His Asp Phe Ala Phe Gly Arg Val Gly
145                     150                     155                     160

Gly Leu Asn Cys Trp Glu His Phe Gln Pro Leu Ser Lys Phe Met Met
                    165                     170                     175

Tyr Ser Leu Gly Glu Gln Val His Val Ala Ser Trp Pro Ala Met Ser
                180                     185                     190

Pro Leu Gln Pro Asp Val Phe Gln Ala Ser Ile Glu Ala Asn Ala Thr
            195                     200                     205

Val Thr Arg Ser Tyr Ala Ile Glu Gly Gln Thr Phe Val Leu Cys Ser
        210                     215                     220

Thr Gln Val Ile Gly Pro Ser Ala Ile Glu Thr Phe Cys Leu Asn Asp
225                     230                     235                     240

Glu Gln Arg Ala Leu Leu Pro Gln Gly Cys Gly Trp Ala Arg Ile Tyr
                    245                     250                     255

Gly Pro Asp Gly Ser Glu Leu Ala Lys Pro Leu Ala Glu Asp Ala Glu
                260                     265                     270

Gly Ile Leu Tyr Ala Glu Ile Asp Leu Glu Gln Ile Leu Leu Ala Lys
            275                     280                     285

Ala Gly Ala Asp Pro Val Gly His Tyr Ser Arg Pro Asp Val Leu Ser
        290                     295                     300

Val Gln Phe Asp Pro Arg Asn His Thr Pro Val His Arg Ile Gly Ile
305                     310                     315                     320

Asp Gly Arg Leu Asp Val Asn Thr Arg Ser Arg Val Glu Asn Phe Arg
                    325                     330                     335

Leu Arg Gln Ala Ala Glu Gln Glu Arg Gln Ala Ser Lys Arg Leu Gly
                340                     345                     350

Thr Lys Leu Phe Glu Gln Ser Leu Leu Ala Glu Glu Pro Val Pro Ala
            355                     360                     365

Lys

<210> SEQ ID NO 11
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

-continued

<400> SEQUENCE: 11

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa tgt agc atc gaa gcc aac gcg acg     624
Pro Leu Gln Pro Asp Val Phe Gln Cys Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att     960
```

```
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
                340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
                355                 360                 365 aag tag                                                             1110
Lys

<210> SEQ ID NO 12
<211> LENGTH: 369
<212> TYPE: PRT
<213> ORGANISM: Acidovorax facilis 72W

<400> SEQUENCE: 12

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Cys Ser Ile Glu Ala Asn Ala Thr
            195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
            275                 280                 285
```

| | | | | | | | | | | |
|---|---|---|---|---|---|---|---|---|---|---|
|Ala|Gly|Ala|Asp|Pro|Val|Gly|His|Tyr|Ser|Arg|Pro|Val|Leu|Ser|
| |290| | | |295| | | |300| |

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 13
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 13

```
atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa acc agc atc gaa gcc aac gcg acg     624
Pro Leu Gln Pro Asp Val Phe Gln Thr Ser Ile Glu Ala Asn Ala Thr
```

```
                195                 200                 205
gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att     960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
        355                 360                 365 aag tag                                                             1110
Lys

<210> SEQ ID NO 14
<211> LENGTH: 369
<212> TYPE: PRT
<213> ORGANISM: Acidovorax facilis 72W

<400> SEQUENCE: 14

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140
```

```
Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
            165                 170                 175

Tyr Ser Leu Gly Glu Gln Val His Val Ala Ser Trp Pro Ala Met Ser
        180                 185                 190

Pro Leu Gln Pro Asp Val Phe Gln Thr Ser Ile Glu Ala Asn Ala Thr
    195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 15
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 15 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95
```

```
atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc        432
Arg Lys Leu Lys Pro Thr His Val Glu Arg Thr Ile Tyr Gly Glu Gly
130                 135                 140 aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg        528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
            180                 185                 190 cct ctt cag ccg gat gtt ttc caa gga agc atc gaa gcc aac gcg acg        624
Pro Leu Gln Pro Asp Val Phe Gln Gly Ser Ile Glu Ala Asn Ala Thr
        195                 200                 205 gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365 aag tag                                                                1110
Lys

<210> SEQ ID NO 16
<211> LENGTH: 369
<212> TYPE: PRT
<213> ORGANISM: Acidovorax facilis 72W

<400> SEQUENCE: 16
```

```
Met Val Ser Tyr Asn Ser Lys Phe Leu Ala Ala Thr Val Gln Ala Glu
 1               5                  10                  15

Pro Val Trp Leu Asp Ala Asp Ala Thr Ile Asp Lys Ser Ile Gly Ile
             20                  25                  30

Ile Glu Glu Ala Ala Gln Lys Gly Ala Ser Leu Ile Ala Phe Pro Glu
         35                  40                  45

Val Phe Ile Pro Gly Tyr Pro Tyr Trp Ala Trp Leu Gly Asp Val Lys
     50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Ala Gly Ser Arg Tyr
            100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Gly Ser Ile Glu Ala Asn Ala Thr
            195                 200                 205

Val Thr Arg Ser Tyr Ala Ile Glu Gly Gln Thr Phe Val Leu Cys Ser
        210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
            355                 360                 365

Lys

<210> SEQ ID NO 17
<211> LENGTH: 1110
<212> TYPE: DNA
<213> ORGANISM: Acidovorax facilis 72W
<220> FEATURE:
<221> NAME/KEY: CDS
```

-continued

<222> LOCATION: (1)..(1110)

<400> SEQUENCE: 17

| | | |
|---|---|---|
| atg gtt tcg tat aac agc aag ttc ctc gcg gca acc gtt cag gca gag<br>Met Val Ser Tyr Asn Ser Lys Phe Leu Ala Ala Thr Val Gln Ala Glu<br>1                   5                    10                 15 | 48 |
| ccg gta tgg ctc gac gca gac gca acg atc gac aag tcg atc ggc atc<br>Pro Val Trp Leu Asp Ala Asp Ala Thr Ile Asp Lys Ser Ile Gly Ile<br>                 20                    25                 30 | 96 |
| atc gaa gaa gct gcc caa aag ggc gcg agt ctg atc gct ttc ccg gaa<br>Ile Glu Glu Ala Ala Gln Lys Gly Ala Ser Leu Ile Ala Phe Pro Glu<br>        35                   40                   45 | 144 |
| gta ttc att ccg ggc tac ccc tat tgg gcg tgg ctc ggc gac gtg aag<br>Val Phe Ile Pro Gly Tyr Pro Tyr Trp Ala Trp Leu Gly Asp Val Lys<br>50                    55                    60 | 192 |
| tac agc cta agc ttt act tca cgc tat cac gag aat tcg ttg gag cta<br>Tyr Ser Leu Ser Phe Thr Ser Arg Tyr His Glu Asn Ser Leu Glu Leu<br>65                     70                    75                 80 | 240 |
| ggt gac gac cgt atg cgt cgc ctc cag ctg gcc gcg cgc cgc aac aaa<br>Gly Asp Asp Arg Met Arg Arg Leu Gln Leu Ala Ala Arg Arg Asn Lys<br>                 85                    90                 95 | 288 |
| atc gca ctc gtc atg ggc tat tcg gag cgg gaa gcc gga tcg cgc tat<br>Ile Ala Leu Val Met Gly Tyr Ser Glu Arg Glu Ala Gly Ser Arg Tyr<br>                 100                 105               110 | 336 |
| ctg agc cag gtg ttc atc gac gag cgt ggc gag atc gtt gcc aat cgg<br>Leu Ser Gln Val Phe Ile Asp Glu Arg Gly Glu Ile Val Ala Asn Arg<br>115                   120                 125 | 384 |
| cgc aag ctg aag ccc aca cac gtt gag cgt acg atc tac ggc gaa ggc<br>Arg Lys Leu Lys Pro Thr His Val Glu Arg Thr Ile Tyr Gly Glu Gly<br>130                   135                 140 | 432 |
| aac gga acc gat ttc ctc acg cac gac ttc gcg ttc gga cgc gtc ggt<br>Asn Gly Thr Asp Phe Leu Thr His Asp Phe Ala Phe Gly Arg Val Gly<br>145                   150                155               160 | 480 |
| gga ttg aac tgc tgg gaa cat ttc caa ccg ctc agc aag ttc atg atg<br>Gly Leu Asn Cys Trp Glu His Phe Gln Pro Leu Ser Lys Phe Met Met<br>                 165                 170               175 | 528 |
| tac agc ctc ggt gag cag gtc cac gtt gca tcg tgg ccg gcg atg tcc<br>Tyr Ser Leu Gly Glu Gln Val His Val Ala Ser Trp Pro Ala Met Ser<br>                 180                 185               190 | 576 |
| cct ctt cag ccg gat gtt ttc caa cac agc atc gaa gcc aac gcg acg<br>Pro Leu Gln Pro Asp Val Phe Gln His Ser Ile Glu Ala Asn Ala Thr<br>195                   200                 205 | 624 |
| gtc acc cgc tcg tac gca atc gaa ggc caa acc ttt gtg ctt tgc tcg<br>Val Thr Arg Ser Tyr Ala Ile Glu Gly Gln Thr Phe Val Leu Cys Ser<br>210                   215                 220 | 672 |
| acg cag gtg atc gga cct agc gcg atc gaa acg ttc tgc ctc aac gac<br>Thr Gln Val Ile Gly Pro Ser Ala Ile Glu Thr Phe Cys Leu Asn Asp<br>225                   230                235               240 | 720 |
| gaa cag cgc gca ctg ttg ccg caa gga tgt ggc tgg gcg cgc att tac<br>Glu Gln Arg Ala Leu Leu Pro Gln Gly Cys Gly Trp Ala Arg Ile Tyr<br>                 245                 250               255 | 768 |
| ggc ccg gat gga agc gag ctt gcg aag cct ctg gcg gaa gat gct gag<br>Gly Pro Asp Gly Ser Glu Leu Ala Lys Pro Leu Ala Glu Asp Ala Glu<br>                 260                 265               270 | 816 |
| ggg atc ttg tac gca gag atc gat ctg gag cag att ctg ctg gcg aag<br>Gly Ile Leu Tyr Ala Glu Ile Asp Leu Glu Gln Ile Leu Leu Ala Lys<br>275                   280                 285 | 864 |
| gct gga gcc gat ccg gtc ggg cac tat tcg cgg cct gac gtg ctg tcg<br>Ala Gly Ala Asp Pro Val Gly His Tyr Ser Arg Pro Asp Val Leu Ser<br>290                   295                 300 | 912 |

```
gtc cag ttc gac ccg cgc aat cat acg cca gtt cat cgc atc ggc att         960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga        1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga        1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca        1104
Thr Lys Leu Phe Glu Gln Ser Leu Leu Ala Glu Glu Pro Val Pro Ala
        355                 360                 365 aag tag                                                                 1110
Lys
```

<210> SEQ ID NO 18
<211> LENGTH: 369
<212> TYPE: PRT
<213> ORGANISM: Acidovorax facilis 72W

<400> SEQUENCE: 18

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln His Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270
```

```
Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 19
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 19 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190
```

```
cct ctt cag ccg gat gtt ttc caa aag agc atc gaa gcc aac gcg acg      624
Pro Leu Gln Pro Asp Val Phe Gln Lys Ser Ile Glu Ala Asn Ala Thr
            195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                             1110
Lys

<210> SEQ ID NO 20
<211> LENGTH: 369
<212> TYPE: PRT
<213> ORGANISM: Acidovorax facilis 72W

<400> SEQUENCE: 20

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125
```

```
Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Lys Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 21
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 21 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                  10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
```

|   |   |   |   |   |   |   |   |   |   |   |   |   |   |   |   |   |
|---|---|---|---|---|---|---|---|---|---|---|---|---|---|---|---|---|
| Gly | Asp | Asp | Arg | Met | Arg | Arg | Leu | Gln | Leu | Ala | Ala | Arg | Arg | Asn | Lys | |
|   |   |   |   | 85 |   |   |   | 90 |   |   |   |   | 95 |   |   |   |

```
atc gca ctc gtc atg ggc tat tcg gag cgg gaa gcc gga tcg cgc tat        336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg        384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc        432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt        480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg        528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc        576
Tyr Ser Leu Gly Glu Gln Val His Val Ala Ser Trp Pro Ala Met Ser
            180                 185                 190 cct ctt cag ccg gat gtt ttc caa aat agc atc gaa gcc aac gcg acg        624
Pro Leu Gln Pro Asp Val Phe Gln Asn Ser Ile Glu Ala Asn Ala Thr
        195                 200                 205 gtc acc cgc tcg tac gca atc gaa ggc caa acc ttt gtg ctt tgc tcg        672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac        720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac        768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag        816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag        864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg        912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att        960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga       1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga       1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca       1104
Thr Lys Leu Phe Glu Gln Ser Leu Leu Ala Glu Glu Pro Val Pro Ala
        355                 360                 365 aag tag                                                               1110
Lys

<210> SEQ ID NO 22
<211> LENGTH: 369
<212> TYPE: PRT
<213> ORGANISM: Acidovorax facilis 72W
```

<400> SEQUENCE: 22

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Asn Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys
```

<210> SEQ ID NO 23
<211> LENGTH: 1110
<212> TYPE: DNA
<213> ORGANISM: Acidovorax facilis 72W -continued

```
<220> FEATURE:
<221> NAME/KEY: CDS
<222> LOCATION: (1)..(1110)

<400> SEQUENCE: 23 atg gtt tcg tat aac agc aag ttc ctc gcg gca acc gtt cag gca gag      48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc      96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa     144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag     192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta     240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa     288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat     336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg     384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc     432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt     480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg     528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc     576
Tyr Ser Leu Gly Glu Gln Val His Val Ala Ser Trp Pro Ala Met Ser
            180                 185                 190 cct ctt cag ccg gat gtt ttc caa tct agc atc gaa gcc aac gcg acg     624
Pro Leu Gln Pro Asp Val Phe Gln Ser Ser Ile Glu Ala Asn Ala Thr
        195                 200                 205 gtc acc cgc tcg tac gca atc gaa ggc caa acc ttt gtg ctt tgc tcg     672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac     720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac     768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag     816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag     864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
```

```
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
                340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
                355                 360                 365 aag tag                                                              1110
Lys
```

<210> SEQ ID NO 24
<211> LENGTH: 369
<212> TYPE: PRT
<213> ORGANISM: Acidovorax facilis 72W

<400> SEQUENCE: 24

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Val Lys
        50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Ser Ser Ile Glu Ala Asn Ala Thr
            195                 200                 205

Val Thr Arg Ser Tyr Ala Ile Glu Gly Gln Thr Phe Val Leu Cys Ser
        210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
```

US 7,198,927 B2
101                                                                 102

-continued

```
                      260                 265                 270
        Gly Ile Leu Tyr Ala Glu Ile Asp Leu Glu Gln Ile Leu Leu Ala Lys
                      275                 280                 285

Ala Gly Ala Asp Pro Val Gly His Tyr Ser Arg Pro Asp Val Leu Ser
                      290                 295                 300

Val Gln Phe Asp Pro Arg Asn His Thr Pro Val His Arg Ile Gly Ile
        305                 310                 315                 320

Asp Gly Arg Leu Asp Val Asn Thr Arg Ser Arg Val Glu Asn Phe Arg
                          325                 330                 335

Leu Arg Gln Ala Ala Glu Gln Glu Arg Gln Ala Ser Lys Arg Leu Gly
                          340                 345                 350

Thr Lys Leu Phe Glu Gln Ser Leu Leu Ala Glu Pro Val Pro Ala
                          355                 360                 365

Lys

<210> SEQ ID NO 25
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 25 atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat aaa caa ccg ctc agc aag ttc atg atg       528
Gly Leu Asn Cys Trp Glu His Lys Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
```

```
                                                                              624
cct ctt cag ccg gat gtt ttc caa ctg agc atc gaa gcc aac gcg acg
Pro Leu Gln Pro Asp Val Phe Gln Leu Ser Ile Glu Ala Asn Ala Thr
        195                 200                 205

672
gtc acc cgc tcg tac gca atc gaa ggc caa acc ttt gtg ctt tgc tcg
Val Thr Arg Ser Tyr Ala Ile Glu Gly Gln Thr Phe Val Leu Cys Ser
210                 215                 220

720
acg cag gtg atc gga cct agc gcg atc gaa acg ttc tgc ctc aac gac
Thr Gln Val Ile Gly Pro Ser Ala Ile Glu Thr Phe Cys Leu Asn Asp
225                 230                 235                 240

768
gaa cag cgc gca ctg ttg ccg caa gga tgt ggc tgg gcg cgc att tac
Glu Gln Arg Ala Leu Leu Pro Gln Gly Cys Gly Trp Ala Arg Ile Tyr
            245                 250                 255

816
ggc ccg gat gga agc gag ctt gcg aag cct ctg gcg gaa gat gct gag
Gly Pro Asp Gly Ser Glu Leu Ala Lys Pro Leu Ala Glu Asp Ala Glu
                260                 265                 270

864
ggg atc ttg tac gca gag atc gat ctg gag cag att ctg ctg gcg aag
Gly Ile Leu Tyr Ala Glu Ile Asp Leu Glu Gln Ile Leu Leu Ala Lys
                    275                 280                 285

912
gct gga gcc gat ccg gtc ggg cac tat tcg cgg cct gac gtg ctg tcg
Ala Gly Ala Asp Pro Val Gly His Tyr Ser Arg Pro Asp Val Leu Ser
290                 295                 300

960
gtc cag ttc gac ccg cgc aat cat acg cca gtt cat cgc atc ggc att
Val Gln Phe Asp Pro Arg Asn His Thr Pro Val His Arg Ile Gly Ile
305                 310                 315                 320

1008
gac ggt cgc ttg gat gtg aat acc cgc agt cgc gtg gag aat ttc cga
Asp Gly Arg Leu Asp Val Asn Thr Arg Ser Arg Val Glu Asn Phe Arg
            325                 330                 335

1056
ctg cga caa gcg gct gag cag gag cgt cag gca tcc aag cgg ctc gga
Leu Arg Gln Ala Ala Glu Gln Glu Arg Gln Ala Ser Lys Arg Leu Gly
                340                 345                 350

1104
acg aaa ctc ttt gaa caa tcc ctt ctg gct gaa gaa ccg gtc cca gca
Thr Lys Leu Phe Glu Gln Ser Leu Leu Ala Glu Glu Pro Val Pro Ala
                    355                 360                 365

1110
aag tag
Lys

<210> SEQ ID NO 26
<211> LENGTH: 369
<212> TYPE: PRT
<213> ORGANISM: Acidovorax facilis 72W

<400> SEQUENCE: 26

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
```

```
                    115                 120                 125
Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Lys Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 27
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 27 atg gtt tcg tat aac agc aag ttc ctc gcg gca acc gtt cag gca gag    48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc    96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa   144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag   192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta   240
Tyr Ser Leu Ser Phe Thr Ser Arg Tyr His Glu Asn Ser Leu Glu Leu
65                  70                  75                  80
```

```
ggt gac gac cgt atg cgt cgc ctc cag ctg gcc gcg cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat   336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg   384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc   432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt   480
Asn Gly Thr Asp Phe Leu Thr His Asp Phe Ala Phe Gly Arg Val Gly
145                 150                 155                 160 gga ttg aac tgc tgg gaa cat atg caa ccg ctc agc aag ttc atg atg   528
Gly Leu Asn Cys Trp Glu His Met Gln Pro Leu Ser Lys Phe Met Met
                165                 170                 175 tac agc ctc ggt gag cag gtc cac gtt gca tcg tgg ccg gcg atg tcc   576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg   624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg   672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac   720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac   768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag   816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag   864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg   912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att   960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga  1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga  1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca  1104
Thr Lys Leu Phe Glu Gln Ser Leu Leu Ala Glu Glu Pro Val Pro Ala
        355                 360                 365 aag tag                                                          1110
Lys

<210> SEQ ID NO 28
<211> LENGTH: 369
```

<212> TYPE: PRT
<213> ORGANISM: Acidovorax facilis 72W

<400> SEQUENCE: 28

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Leu Gln Leu Ala Ala Arg Arg Asn Lys
                85                  90                  95

Ile Ala Leu Val Met Gly Tyr Ser Glu Arg Ala Gly Ser Arg Tyr
                100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Met Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys
```

<210> SEQ ID NO 29
<211> LENGTH: 1110

```
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 29 atg gtt tcg tat aac agc aag ttc ctc gcg gca acc gtt cag gca gag        48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc        96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa       144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag       192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta       240
Tyr Ser Leu Ser Phe Thr Ser Arg Tyr His Glu Asn Ser Leu Glu Leu
65              70                  75                  80 ggt gac gac cgt atg cgt cgc ctc cag ctg gcc gcg cgc cgc aac aaa       288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat       336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg       384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc       432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt       480
Asn Gly Thr Asp Phe Leu Thr His Asp Phe Ala Phe Gly Arg Val Gly
145                 150                 155                 160 gga ttg aac tgc tgg gaa cat acc caa ccg ctc agc aag ttc atg atg       528
Gly Leu Asn Cys Trp Glu His Thr Gln Pro Leu Ser Lys Phe Met Met
                165                 170                 175 tac agc ctc ggt gag cag gtc cac gtt gca tcg tgg ccg gcg atg tcc       576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg       624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg       672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac       720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac       768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag       816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag       864
Gly Ile Leu Tyr Ala Glu Ile Asp Leu Glu Gln Ile Leu Leu Ala Lys
        275                 280                 285
```

```
gct gga gcc gat ccg gtc ggg cac tat tcg cgg cct gac gtg ctg tcg    912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att    960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga   1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga   1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca   1104
Thr Lys Leu Phe Glu Gln Ser Leu Leu Ala Glu Glu Pro Val Pro Ala
        355                 360                 365 aag tag                                                           1110
Lys
```

<210> SEQ ID NO 30
<211> LENGTH: 369
<212> TYPE: PRT
<213> ORGANISM: Acidovorax facilis 72W

<400> SEQUENCE: 30

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Thr Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255
```

-continued

```
Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
            290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
            355                 360                 365

Lys
```

<210> SEQ ID NO 31
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 31

```
atg gtt tcg tat aac agc aag ttc ctc gcg gca acc gtt cag gca gag     48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc     96
Pro Val Trp Leu Asp Ala Asp Ala Thr Ile Asp Lys Ser Ile Gly Ile
                20                  25                  30 atc gaa gaa gct gcc caa aag ggc gcg agt ctg atc gct ttc ccg gaa    144
Ile Glu Glu Ala Ala Gln Lys Gly Ala Ser Leu Ile Ala Phe Pro Glu
            35                  40                  45 gta ttc att ccg ggc tac ccc tat tgg gcg tgg ctc ggc gac gtg aag    192
Val Phe Ile Pro Gly Tyr Pro Tyr Trp Ala Trp Leu Gly Asp Val Lys
        50                  55                  60 tac agc cta agc ttt act tca cgc tat cac gag aat tcg ttg gag cta    240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa    288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat    336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg    384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc    432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt    480
Asn Gly Thr Asp Phe Leu Thr His Asp Phe Ala Phe Gly Arg Val Gly
145                 150                 155                 160 gga ttg aac tgc tgg gaa cat gtg caa ccg ctc agc aag ttc atg atg    528
Gly Leu Asn Cys Trp Glu His Val Gln Pro Leu Ser Lys Phe Met Met
                165                 170                 175
```

```
tac agc ctc ggt gag cag gtc cac gtt gca tcg tgg ccg gcg atg tcc      576
Tyr Ser Leu Gly Glu Gln Val His Val Ala Ser Trp Pro Ala Met Ser
            180                 185                 190 cct ctt cag ccg gat gtt ttc caa ctg agc atc gaa gcc aac gcg acg      624
Pro Leu Gln Pro Asp Val Phe Gln Leu Ser Ile Glu Ala Asn Ala Thr
        195                 200                 205 gtc acc cgc tcg tac gca atc gaa ggc caa acc ttt gtg ctt tgc tcg      672
Val Thr Arg Ser Tyr Ala Ile Glu Gly Gln Thr Phe Val Leu Cys Ser
    210                 215                 220 acg cag gtg atc gga cct agc gcg atc gaa acg ttc tgc ctc aac gac      720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac      768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag      816
Gly Pro Asp Gly Ser Glu Leu Ala Lys Pro Leu Ala Glu Asp Ala Glu
            260                 265                 270 ggg atc ttg tac gca gag atc gat ctg gag cag att ctg ctg gcg aag      864
Gly Ile Leu Tyr Ala Glu Ile Asp Leu Glu Gln Ile Leu Leu Ala Lys
        275                 280                 285 gct gga gcc gat ccg gtc ggg cac tat tcg cgg cct gac gtg ctg tcg      912
Ala Gly Ala Asp Pro Val Gly His Tyr Ser Arg Pro Asp Val Leu Ser
    290                 295                 300 gtc cag ttc gac ccg cgc aat cat acg cca gtt cat cgc atc ggc att      960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga     1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga     1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca     1104
Thr Lys Leu Phe Glu Gln Ser Leu Leu Ala Glu Glu Pro Val Pro Ala
        355                 360                 365 aag tag                                                              1110
Lys

<210> SEQ ID NO 32
<211> LENGTH: 369
<212> TYPE: PRT
<213> ORGANISM: Acidovorax facilis 72W

<400> SEQUENCE: 32

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110
```

```
Leu Ser Gln Val Phe Ile Asp Glu Arg Gly Glu Ile Val Ala Asn Arg
        115                 120                 125
Arg Lys Leu Lys Pro Thr His Val Glu Arg Thr Ile Tyr Gly Glu Gly
    130                 135                 140
Asn Gly Thr Asp Phe Leu Thr His Asp Phe Ala Phe Gly Arg Val Gly
145                 150                 155                 160
Gly Leu Asn Cys Trp Glu His Val Gln Pro Leu Ser Lys Phe Met Met
                165                 170                 175
Tyr Ser Leu Gly Glu Gln Val His Val Ala Ser Trp Pro Ala Met Ser
            180                 185                 190
Pro Leu Gln Pro Asp Val Phe Gln Leu Ser Ile Glu Ala Asn Ala Thr
        195                 200                 205
Val Thr Arg Ser Tyr Ala Ile Glu Gly Gln Thr Phe Val Leu Cys Ser
    210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
            260                 265                 270
Gly Ile Leu Tyr Ala Glu Ile Asp Leu Glu Gln Ile Leu Leu Ala Lys
        275                 280                 285
Ala Gly Ala Asp Pro Val Gly His Tyr Ser Arg Pro Asp Val Leu Ser
    290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Gly Arg Gln Ala Ser Lys Arg Leu Gly
            340                 345                 350
Thr Lys Leu Phe Glu Gln Ser Leu Leu Ala Glu Glu Pro Val Pro Ala
        355                 360                 365
Lys

<210> SEQ ID NO 33
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 33 atg gtt tcg tat aac agc aag ttc ctc gcg gca acc gtt cag gca gag     48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc     96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa    144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag    192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta    240
```

```
                                                                                         -continued Tyr Ser Leu Ser Phe Thr Ser Arg Tyr His Glu Asn Ser Leu Glu Leu
 65              70                  75                  80 ggt gac gac cgt atg cgt cgc ctc cag ctg gcc gcg cgc cgc aac aaa          288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat          336
Ile Ala Leu Val Met Gly Tyr Ser Glu Arg Glu Ala Gly Ser Arg Tyr
                100                 105                 110 ctg agc cag gtg ttc atc gac gag cgt ggc gag atc gtt gcc aat cgg          384
Leu Ser Gln Val Phe Ile Asp Glu Arg Gly Glu Ile Val Ala Asn Arg
            115                 120                 125 cgc aag ctg aag ccc aca cac gtt gag cgt acg atc tac ggc gaa ggc          432
Arg Lys Leu Lys Pro Thr His Val Glu Arg Thr Ile Tyr Gly Glu Gly
        130                 135                 140 aac gga acc gat ttc ctc acg cac gac ttc gcg ttc gga cgc gtc ggt          480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg          528
Gly Leu Asn Cys Trp Glu His Phe Gln Pro Leu Ser Lys Phe Met Met
                165                 170                 175 tac agc ctc ggt gag cag gtc cac gtt gca tcg tgg ccg gcg atg tcc          576
Tyr Ser Leu Gly Glu Gln Val His Val Ala Ser Trp Pro Ala Met Ser
                180                 185                 190 cct ctt cag ccg gat gtt ttc caa ctg agc atc gaa gcc aac gcg acg          624
Pro Leu Gln Pro Asp Val Phe Gln Leu Ser Ile Glu Ala Asn Ala Thr
            195                 200                 205 gtc gcc cgc tcg tac gca atc gaa ggc caa acc ttt gtg ctt tgc tcg          672
Val Ala Arg Ser Tyr Ala Ile Glu Gly Gln Thr Phe Val Leu Cys Ser
        210                 215                 220 acg cag gtg atc gga cct agc gcg atc gaa acg ttc tgc ctc aac gac          720
Thr Gln Val Ile Gly Pro Ser Ala Ile Glu Thr Phe Cys Leu Asn Asp
225                 230                 235                 240 gaa cag cgc gca ctg ttg ccg caa gga tgt ggc tgg gcg cgc att tac          768
Glu Gln Arg Ala Leu Leu Pro Gln Gly Cys Gly Trp Ala Arg Ile Tyr
                245                 250                 255 ggc ccg gat gga agc gag ctt gcg aag cct ctg gcg gaa gat gct gag          816
Gly Pro Asp Gly Ser Glu Leu Ala Lys Pro Leu Ala Glu Asp Ala Glu
                260                 265                 270 ggg atc ttg tac gca gag atc gat ctg gag cag att ctg ctg gcg aag          864
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg          912
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att          960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga         1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga         1056
Leu Arg Gln Ala Ala Glu Gln Glu Arg Gln Ala Ser Lys Arg Leu Gly
                340                 345                 350 acg aaa ctc ttt gaa caa tcc ctt ctg gct gaa gaa ccg gtc cca gca         1104
Thr Lys Leu Phe Glu Gln Ser Leu Leu Ala Glu Glu Pro Val Pro Ala
            355                 360                 365 aag tag                                                                 1110
Lys
```

<210> SEQ ID NO 34
<211> LENGTH: 369
<212> TYPE: PRT
<213> ORGANISM: Acidovorax facilis 72W

<400> SEQUENCE: 34

```
Met Val Ser Tyr Asn Ser Lys Phe Leu Ala Ala Thr Val Gln Ala Glu
1               5                   10                  15
Pro Val Trp Leu Asp Ala Asp Ala Thr Ile Asp Lys Ser Ile Gly Ile
            20                  25                  30
Ile Glu Glu Ala Ala Gln Lys Gly Ala Ser Leu Ile Ala Phe Pro Glu
        35                  40                  45
Val Phe Ile Pro Gly Tyr Pro Tyr Trp Ala Trp Leu Gly Asp Val Lys
    50                  55                  60
Tyr Ser Leu Ser Phe Thr Ser Arg Tyr His Glu Asn Ser Leu Glu Leu
65                  70                  75                  80
Gly Asp Asp Arg Met Arg Arg Leu Gln Leu Ala Ala Arg Arg Asn Lys
                85                  90                  95
Ile Ala Leu Val Met Gly Tyr Ser Glu Arg Glu Ala Gly Ser Arg Tyr
            100                 105                 110
Leu Ser Gln Val Phe Ile Asp Glu Arg Gly Glu Ile Val Ala Asn Arg
        115                 120                 125
Arg Lys Leu Lys Pro Thr His Val Glu Arg Thr Ile Tyr Gly Glu Gly
    130                 135                 140
Asn Gly Thr Asp Phe Leu Thr His Asp Phe Ala Phe Gly Arg Val Gly
145                 150                 155                 160
Gly Leu Asn Cys Trp Glu His Phe Gln Pro Leu Ser Lys Phe Met Met
                165                 170                 175
Tyr Ser Leu Gly Glu Gln Val His Val Ala Ser Trp Pro Ala Met Ser
            180                 185                 190
Pro Leu Gln Pro Asp Val Phe Gln Leu Ser Ile Glu Ala Asn Ala Thr
        195                 200                 205
Val Ala Arg Ser Tyr Ala Ile Glu Gly Gln Thr Phe Val Leu Cys Ser
    210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Cys Gly Trp Ala Arg Ile Tyr
                245                 250                 255
Gly Pro Asp Gly Ser Glu Leu Ala Lys Pro Leu Ala Glu Asp Ala Glu
            260                 265                 270
Gly Ile Leu Tyr Ala Glu Ile Asp Leu Glu Gln Ile Leu Leu Ala Lys
        275                 280                 285
Ala Gly Ala Asp Pro Val Gly His Tyr Ser Arg Pro Asp Val Leu Ser
    290                 295                 300
Val Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
            340                 345                 350
Thr Lys Leu Phe Glu Gln Ser Leu Leu Ala Glu Glu Pro Val Pro Ala
        355                 360                 365
Lys
```

<210> SEQ ID NO 35
<211> LENGTH: 1110
<212> TYPE: DNA
<213> ORGANISM: Acidovorax facilis 72W
<220> FEATURE:
<221> NAME/KEY: CDS
<222> LOCATION: (1)..(1110)

<400> SEQUENCE: 35

| | | | | | | | | | | | | | | | | |
|---|---|---|---|---|---|---|---|---|---|---|---|---|---|---|---|---|
| atg | gtt | tcg | tat | aac | agc | aag | ttc | ctc | gcg | gca | acc | gtt | cag | gca | gag | 48 |
| Met | Val | Ser | Tyr | Asn | Ser | Lys | Phe | Leu | Ala | Ala | Thr | Val | Gln | Ala | Glu | |
| 1 | | | | 5 | | | | | 10 | | | | | 15 | | |
| ccg | gta | tgg | ctc | gac | gca | gac | gca | acg | atc | gac | aag | tcg | atc | ggc | atc | 96 |
| Pro | Val | Trp | Leu | Asp | Ala | Asp | Ala | Thr | Ile | Asp | Lys | Ser | Ile | Gly | Ile | |
| | | | 20 | | | | | 25 | | | | | 30 | | | |
| atc | gaa | gaa | gct | gcc | caa | aag | ggc | gcg | agt | ctg | atc | gct | ttc | ccg | gaa | 144 |
| Ile | Glu | Glu | Ala | Ala | Gln | Lys | Gly | Ala | Ser | Leu | Ile | Ala | Phe | Pro | Glu | |
| | | 35 | | | | | 40 | | | | | 45 | | | | |
| gta | ttc | att | ccg | ggc | tac | ccc | tat | tgg | gcg | tgg | ctc | ggc | gac | gtg | aag | 192 |
| Val | Phe | Ile | Pro | Gly | Tyr | Pro | Tyr | Trp | Ala | Trp | Leu | Gly | Asp | Val | Lys | |
| 50 | | | | | 55 | | | | | 60 | | | | | | |
| tac | agc | cta | agc | ttt | act | tca | cgc | tat | cac | gag | aat | tcg | ttg | gag | cta | 240 |
| Tyr | Ser | Leu | Ser | Phe | Thr | Ser | Arg | Tyr | His | Glu | Asn | Ser | Leu | Glu | Leu | |
| 65 | | | | | 70 | | | | | 75 | | | | | 80 | |
| ggt | gac | gac | cgt | atg | cgt | cgc | ctc | cag | ctg | gcc | gcg | cgc | cgc | aac | aaa | 288 |
| Gly | Asp | Asp | Arg | Met | Arg | Arg | Leu | Gln | Leu | Ala | Ala | Arg | Arg | Asn | Lys | |
| | | | | 85 | | | | | 90 | | | | | 95 | | |
| atc | gca | ctc | gtc | atg | ggc | tat | tcg | gag | cgg | gaa | gcc | gga | tcg | cgc | tat | 336 |
| Ile | Ala | Leu | Val | Met | Gly | Tyr | Ser | Glu | Arg | Glu | Ala | Gly | Ser | Arg | Tyr | |
| | | | 100 | | | | | 105 | | | | | 110 | | | |
| ctg | agc | cag | gtg | ttc | atc | gac | gag | cgt | ggc | gag | atc | gtt | gcc | aat | cgg | 384 |
| Leu | Ser | Gln | Val | Phe | Ile | Asp | Glu | Arg | Gly | Glu | Ile | Val | Ala | Asn | Arg | |
| | | 115 | | | | | 120 | | | | | 125 | | | | |
| cgc | aag | ctg | aag | ccc | aca | cac | gtt | gag | cgt | acg | atc | tac | ggc | gaa | ggc | 432 |
| Arg | Lys | Leu | Lys | Pro | Thr | His | Val | Glu | Arg | Thr | Ile | Tyr | Gly | Glu | Gly | |
| | 130 | | | | | 135 | | | | | 140 | | | | | |
| aac | gga | acc | gat | ttc | ctc | acg | cac | gac | ttc | gcg | ttc | gga | cgc | gtc | ggt | 480 |
| Asn | Gly | Thr | Asp | Phe | Leu | Thr | His | Asp | Phe | Ala | Phe | Gly | Arg | Val | Gly | |
| 145 | | | | | 150 | | | | | 155 | | | | | 160 | |
| gga | ttg | aac | tgc | tgg | gaa | cat | ttc | caa | ccg | ctc | agc | aag | ttc | atg | atg | 528 |
| Gly | Leu | Asn | Cys | Trp | Glu | His | Phe | Gln | Pro | Leu | Ser | Lys | Phe | Met | Met | |
| | | | | 165 | | | | | 170 | | | | | 175 | | |
| tac | agc | ctc | ggt | gag | cag | gtc | cac | gtt | gca | tcg | tgg | ccg | gcg | atg | tcc | 576 |
| Tyr | Ser | Leu | Gly | Glu | Gln | Val | His | Val | Ala | Ser | Trp | Pro | Ala | Met | Ser | |
| | | | 180 | | | | | 185 | | | | | 190 | | | |
| cct | ctt | cag | ccg | gat | gtt | ttc | caa | ctg | agc | atc | gaa | gcc | aac | gcg | acg | 624 |
| Pro | Leu | Gln | Pro | Asp | Val | Phe | Gln | Leu | Ser | Ile | Glu | Ala | Asn | Ala | Thr | |
| | | 195 | | | | | 200 | | | | | 205 | | | | |
| gtc | tgc | cgc | tcg | tac | gca | atc | gaa | ggc | caa | acc | ttt | gtg | ctt | tgc | tcg | 672 |
| Val | Cys | Arg | Ser | Tyr | Ala | Ile | Glu | Gly | Gln | Thr | Phe | Val | Leu | Cys | Ser | |
| | 210 | | | | | 215 | | | | | 220 | | | | | |
| acg | cag | gtg | atc | gga | cct | agc | gcg | atc | gaa | acg | ttc | tgc | ctc | aac | gac | 720 |
| Thr | Gln | Val | Ile | Gly | Pro | Ser | Ala | Ile | Glu | Thr | Phe | Cys | Leu | Asn | Asp | |
| 225 | | | | | 230 | | | | | 235 | | | | | 240 | |
| gaa | cag | cgc | gca | ctg | ttg | ccg | caa | gga | tgt | ggc | tgg | gcg | cgc | att | tac | 768 |
| Glu | Gln | Arg | Ala | Leu | Leu | Pro | Gln | Gly | Cys | Gly | Trp | Ala | Arg | Ile | Tyr | |
| | | | | 245 | | | | | 250 | | | | | 255 | | |
| ggc | ccg | gat | gga | agc | gag | ctt | gcg | aag | cct | ctg | gcg | gaa | gat | gct | gag | 816 |
| Gly | Pro | Asp | Gly | Ser | Glu | Leu | Ala | Lys | Pro | Leu | Ala | Glu | Asp | Ala | Glu | |
| | | | 260 | | | | | 265 | | | | | 270 | | | |
| ggg | atc | ttg | tac | gca | gag | atc | gat | ctg | gag | cag | att | ctg | ctg | gcg | aag | 864 |

-continued

```
Gly Ile Leu Tyr Ala Glu Ile Asp Leu Glu Gln Ile Leu Leu Ala Lys
            275                 280                 285 gct gga gcc gat ccg gtc ggg cac tat tcg cgg cct gac gtg ctg tcg     912
Ala Gly Ala Asp Pro Val Gly His Tyr Ser Arg Pro Asp Val Leu Ser
        290                 295                 300 gtc cag ttc gac ccg cgc aat cat acg cca gtt cat cgc atc ggc att     960
Val Gln Phe Asp Pro Arg Asn His Thr Pro Val His Arg Ile Gly Ile
305                 310                 315                 320 gac ggt cgc ttg gat gtg aat acc cgc agt cgc gtg gag aat ttc cga    1008
Asp Gly Arg Leu Asp Val Asn Thr Arg Ser Arg Val Glu Asn Phe Arg
                325                 330                 335 ctg cga caa gcg gct gag cag gag cgt cag gca tcc aag cgg ctc gga    1056
Leu Arg Gln Ala Ala Glu Gln Glu Arg Gln Ala Ser Lys Arg Leu Gly
            340                 345                 350 acg aaa ctc ttt gaa caa tcc ctt ctg gct gaa gaa ccg gtc cca gca    1104
Thr Lys Leu Phe Glu Gln Ser Leu Leu Ala Glu Glu Pro Val Pro Ala
        355                 360                 365 aag tag                                                              1110
Lys
```

<210> SEQ ID NO 36
<211> LENGTH: 369
<212> TYPE: PRT
<213> ORGANISM: Acidovorax facilis 72W

<400> SEQUENCE: 36

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Cys Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240
```

-continued

```
Glu Gln Arg Ala Leu Leu Pro Gln Gly Cys Gly Trp Ala Arg Ile Tyr
            245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
        290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
                355                 360                 365

Lys

<210> SEQ ID NO 37
<211> LENGTH: 1110
<212> TYPE: DNA
<213> ORGANISM: Escherichia coli SS1001
<220> FEATURE:
<221> NAME/KEY: CDS
<222> LOCATION: (1)..(1110)

<400> SEQUENCE: 37 atg gtt tcg tat aac agc aag ttc ctc gcg gca acc gtt cag gca gag       48
Met Val Ser Tyr Asn Ser Lys Phe Leu Ala Ala Thr Val Gln Ala Glu
1               5                   10                  15 ccg gta tgg ctc gac gca gac gca acg atc gac aag tcg atc ggc atc       96
Pro Val Trp Leu Asp Ala Asp Ala Thr Ile Asp Lys Ser Ile Gly Ile
            20                  25                  30 atc gaa gaa gct gcc caa aag ggc gcg agt ctg atc gct ttc ccg gaa      144
Ile Glu Glu Ala Ala Gln Lys Gly Ala Ser Leu Ile Ala Phe Pro Glu
        35                  40                  45 gta ttc att ccg ggc tac ccc tat tgg gcg tgg ctc ggc gac gtg aag      192
Val Phe Ile Pro Gly Tyr Pro Tyr Trp Ala Trp Leu Gly Asp Val Lys
    50                  55                  60 tac agc cta agc ttt act tca cgc tat cac gag aat tcg ttg gag cta      240
Tyr Ser Leu Ser Phe Thr Ser Arg Tyr His Glu Asn Ser Leu Glu Leu
65                  70                  75                  80 ggt gac gac cgt atg cgt cgc ctc cag ctg gcc gcg cgc cgc aac aaa      288
Gly Asp Asp Arg Met Arg Arg Leu Gln Leu Ala Ala Arg Arg Asn Lys
                85                  90                  95 atc gca ctc gtc atg ggc tat tcg gag cgg gaa gcc gga tcg cgc tat      336
Ile Ala Leu Val Met Gly Tyr Ser Glu Arg Glu Ala Gly Ser Arg Tyr
            100                 105                 110 ctg agc cag gtg ttc atc gac gag cgt ggc gag atc gtt gcc aat cgg      384
Leu Ser Gln Val Phe Ile Asp Glu Arg Gly Glu Ile Val Ala Asn Arg
        115                 120                 125 cgc aag ctg aag ccc aca cac gtt gag cgt acg atc tac ggc gaa ggc      432
Arg Lys Leu Lys Pro Thr His Val Glu Arg Thr Ile Tyr Gly Glu Gly
    130                 135                 140 aac gga acc gat ttc ctc acg cac gac ttc gcg ttc gga cgc gtc ggt      480
Asn Gly Thr Asp Phe Leu Thr His Asp Phe Ala Phe Gly Arg Val Gly
145                 150                 155                 160 gga ttg aac tgc tgg gaa cat ttc caa ccg ctc agc aag ttc atg atg      528
Gly Leu Asn Cys Trp Glu His Phe Gln Pro Leu Ser Lys Phe Met Met
```

|  |  |  |  |  |  |  |  |  |  |  |  |  |  |  |  |
|---|---|---|---|---|---|---|---|---|---|---|---|---|---|---|---|
|  |  |  | 165 |  |  |  | 170 |  |  |  | 175 |  |  |  |  |
| tac | agc | ctc | ggt | gag | cag | gtc | cac | gtt | gca | tcg | tgg | ccg | gcg | atg | tcc | 576 |
| Tyr | Ser | Leu | Gly<br>180 | Glu | Gln | Val | His | Val<br>185 | Ala | Ser | Trp | Pro | Ala<br>190 | Met | Ser |  |
| cct | ctt | cag | ccg | gat | gtt | ttc | caa | ctg | agc | atc | gaa | gcc | aac | gcg | acg | 624 |
| Pro | Leu | Gln<br>195 | Pro | Asp | Val | Phe | Gln<br>200 | Leu | Ser | Ile | Glu | Ala<br>205 | Asn | Ala | Thr |  |
| gtc | acc | cgc | tcg | tac | gca | atc | gaa | ggc | caa | acc | ttt | gtg | ctt | tgc | tcg | 672 |
| Val | Thr<br>210 | Arg | Ser | Tyr | Ala | Ile<br>215 | Glu | Gly | Gln | Thr<br>220 | Phe | Val | Leu | Cys | Ser |  |
| acg | cag | gtg | atc | gga | cct | agc | gcg | atc | gaa | acg | ttc | tgc | ctc | aac | gac | 720 |
| Thr<br>225 | Gln | Val | Ile | Gly | Pro<br>230 | Ser | Ala | Ile | Glu | Thr<br>235 | Phe | Cys | Leu | Asn | Asp<br>240 |  |
| gaa | cag | cgc | gca | ctg | ttg | ccg | caa | gga | tgt | ggc | tgg | gcg | cgc | att | tac | 768 |
| Glu | Gln | Arg | Ala | Leu<br>245 | Leu | Pro | Gln | Gly | Cys<br>250 | Gly | Trp | Ala | Arg | Ile<br>255 | Tyr |  |
| ggc | ccg | gat | gga | agc | gag | ctt | gcg | aag | cct | ctg | gcg | gaa | gat | gct | gag | 816 |
| Gly | Pro | Asp | Gly | Ser<br>260 | Glu | Leu | Ala | Lys | Pro<br>265 | Leu | Ala | Glu | Asp<br>270 | Ala | Glu |  |
| ggg | atc | ttg | tac | gca | gag | atc | gat | ctg | gag | cag | att | ctg | ctg | gcg | aag | 864 |
| Gly | Ile | Leu | Tyr<br>275 | Ala | Glu | Ile | Asp<br>280 | Leu | Glu | Gln | Ile | Leu<br>285 | Leu | Ala | Lys |  |
| gct | gga | gcc | gat | ccg | gtc | ggg | cac | tat | tcg | cgg | cct | gac | gtg | ctg | tcg | 912 |
| Ala | Gly<br>290 | Ala | Asp | Pro | Val | Gly<br>295 | His | Tyr | Ser | Arg | Pro<br>300 | Asp | Val | Leu | Ser |  |
| gtc | cag | ttc | gac | ccg | cgc | aat | cat | acg | cca | gtt | cat | cgc | atc | ggc | att | 960 |
| Val<br>305 | Gln | Phe | Asp | Pro | Arg<br>310 | Asn | His | Thr | Pro | Val<br>315 | His | Arg | Ile | Gly | Ile<br>320 |  |
| gac | ggt | cgc | ttg | gat | gtg | aat | acc | cgc | agt | cgc | gtg | gag | aat | ttc | cga | 1008 |
| Asp | Gly | Arg | Leu | Asp<br>325 | Val | Asn | Thr | Arg | Ser<br>330 | Arg | Val | Glu | Asn | Phe<br>335 | Arg |  |
| ctg | cga | caa | gcg | gct | gag | cag | gag | cgt | cag | gca | tcc | aag | cgg | ctc | gga | 1056 |
| Leu | Arg | Gln | Ala<br>340 | Ala | Glu | Gln | Glu | Arg<br>345 | Gln | Ala | Ser | Lys | Arg<br>350 | Leu | Gly |  |
| acg | aaa | ctc | ttt | gaa | caa | tcc | ctt | ctg | gct | gaa | gaa | ccg | gtc | tca | gca | 1104 |
| Thr | Lys | Leu | Phe<br>355 | Glu | Gln | Ser | Leu | Leu<br>360 | Ala | Glu | Glu | Pro | Val<br>365 | Ser | Ala |  |
| aag | tag |  |  |  |  |  |  |  |  |  |  |  |  |  |  | 1110 |
| Lys |  |  |  |  |  |  |  |  |  |  |  |  |  |  |  |  |

<210> SEQ ID NO 38
<211> LENGTH: 369
<212> TYPE: PRT
<213> ORGANISM: Escherichia coli SS1001

<400> SEQUENCE: 38

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Val Lys
        50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

-continued

```
Ile Ala Leu Val Met Gly Tyr Ser Glu Arg Glu Ala Gly Ser Arg Tyr
            100             105             110

Leu Ser Gln Val Phe Ile Asp Glu Arg Gly Glu Ile Val Ala Asn Arg
        115             120             125

Arg Lys Leu Lys Pro Thr His Val Glu Arg Thr Ile Tyr Gly Glu Gly
    130             135             140

Asn Gly Thr Asp Phe Leu Thr His Asp Phe Ala Phe Gly Arg Val Gly
145             150             155             160

Gly Leu Asn Cys Trp Glu His Phe Gln Pro Leu Ser Lys Phe Met Met
                165             170             175

Tyr Ser Leu Gly Glu Gln Val His Val Ala Ser Trp Pro Ala Met Ser
            180             185             190

Pro Leu Gln Pro Asp Val Phe Gln Leu Ser Ile Glu Ala Asn Ala Thr
            195             200             205

Val Thr Arg Ser Tyr Ala Ile Glu Gly Gln Thr Phe Val Leu Cys Ser
    210             215             220

Thr Gln Val Ile Gly Pro Ser Ala Ile Glu Thr Phe Cys Leu Asn Asp
225             230             235             240

Glu Gln Arg Ala Leu Leu Pro Gln Gly Cys Gly Trp Ala Arg Ile Tyr
                245             250             255

Gly Pro Asp Gly Ser Glu Leu Ala Lys Pro Leu Ala Glu Asp Ala Glu
            260             265             270

Gly Ile Leu Tyr Ala Glu Ile Asp Leu Glu Gln Ile Leu Leu Ala Lys
            275             280             285

Ala Gly Ala Asp Pro Val Gly His Tyr Ser Arg Pro Asp Val Leu Ser
    290             295             300

Val Gln Phe Asp Pro Arg Asn His Thr Pro Val His Arg Ile Gly Ile
305             310             315             320

Asp Gly Arg Leu Asp Val Asn Thr Arg Ser Arg Val Glu Asn Phe Arg
            325             330             335

Leu Arg Gln Ala Ala Glu Gln Glu Arg Gln Ala Ser Lys Arg Leu Gly
            340             345             350

Thr Lys Leu Phe Glu Gln Ser Leu Leu Ala Glu Glu Pro Val Ser Ala
        355             360             365

Lys
```

US 7,198,927 B2

ENZYMATIC PRODUCTION OF GLYCOLIC ACID

This application claims the benefit of U.S. Provisional Application Nos. 60/638,176 and 60/638,127, both filed Dec. 22, 2004.

FIELD OF THE INVENTION

This invention relates to the field of microbiology and molecular biology. More specifically, a method for enzymatic production of glycolic acid from glycolonitrile is provided using mutant nitrilases having improved nitrilase activity.

BACKGROUND OF THE INVENTION

Glycolic acid ($HOCH_2COOH$; CAS Registry Number is 79-14-1) is the simplest member of the α-hydroxy acid family of carboxylic acids. Its properties make it ideal for a broad spectrum of consumer and industrial applications, including use in water well rehabilitation, the leather industry, the oil and gas industry, the laundry and textile industry, as a monomer in the preparation of polyglycolic acid (PGA), and as a component in personal care products. Glycolic acid also is a principle ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]). Recently, it has been reported that polyglycolic acid is useful as a gas barrier material (i.e., exhibits high oxygen barrier characteristics) for packing foods and carbonated drinks (WO 2005/106005 A1). However, traditional chemical synthesis of glycolic acid produces a significant amount of impurities that must be removed prior to use in preparing polyglycolic acid for gas barrier materials. New technology to commercially produce glycolic acid, especially one that produces glycolic acid in high purity and at low cost, would be eagerly received by industry.

Various methods are known for preparing α-hydroxy acids using the corresponding α-hydroxy nitrile as the starting material and a microorganism as the catalyst. Examples of α-hydroxy acids produced include: glycolic acid, lactic acid, 2-hydroxyisobutyric acid, 2-hydroxy-2-phenyl propionic acid, mandelic acid, 2-hydroxy-3,3-dimethyl-4-butyrolactone, and 4-methylthiobutyric acid. These products are synthesized using microorganisms, such as those belonging to the genera *Nocardia, Bacillus, Brevibacterium, Aureobacterium, Pseudomonas, Caseobacter, Alcaligenes, Acinetobacter, Enterobacter, Arthrobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, Rhodococcus, Corynebacterium, Microbacterium, Obsumbacterium* and *Gordona*. (JP-A-4-99495, JP-A-4-99496 and JP-A-4-218385 corresponding to U.S. Pat. No. 5,223,416; JP-A4-99497 corresponding to U.S. Pat. No. 5,234,826; JP-A-5-95795 corresponding to U.S. Pat. No. 5,296,373; JP-A-5-192187; JP-A-5-192189 corresponding to U.S. Pat. No. 5,326,702; JP-A-6-237789 corresponding to EP-A-0610048; JP-A-6-284899 corresponding to EP-A-0610049; JP-A-7-213296 corresponding to U.S. Pat. No. 5,508,181).

However, most known methods for preparing α-hydroxy acids from the corresponding α-hydroxy nitrites as mentioned above do not produce and accumulate a product at a sufficiently high concentration to meet commercial needs. This is frequently a result of enzyme inactivation early in the reaction period. U.S. Pat. No. 5,756,306 teaches that "When an α-hydroxy nitrile is enzymatically hydrolyzed or hydrated using nitrilase or nitrile hydratase to produce an α-hydroxy acid or α-hydroxy amide, a problem occurs in that the enzyme is inactivated within a short period of time. It is therefore difficult to obtain the α-hydroxy acid or α-hydroxy amide in high concentration and high yield." (col. 1, lines 49–54). Maintaining the aldehyde concentration (formed by the disassociation of α-hydroxy nitrile to aldehyde and hydrogen cyanide) and/or the α-hydroxy nitrile concentration in the reaction mixture within a specified range is one method to avoid this problem.

U.S. Pat. No. 5,508,181 addresses further difficulties relating to rapid enzyme inactivation. Specifically, U.S. Pat. No. 5,508,181 mentions that α-hydroxy nitrile compounds partially disassociate into the corresponding aldehydes, according to the disassociation equilibrium. These aldehydes inactivate the enzyme within a short period of time by binding to the protein, thus making it difficult to obtain α-hydroxy acid or α-hydroxy amide in a high concentration with high productivity from α-hydroxy nitrites (col. 2, lines 16–29). As a solution to prevent enzyme inactivation due to accumulation of aldehydes, phosphate or hypophosphite ions were added to the reaction mixture. U.S. Pat. No. 5,326,702 uses sulfite, disulfite, or dithionite ions to sequester aldehyde and prevent enzyme inactivation. However, the concentration of α-hydroxy acid produced and accumulated even by using such additives as described above is not great.

U.S. Pat. No. 6,037,155 teaches that low accumulation of α-hydroxy acid products is related to enzyme inactivation within a short time due to the disassociated-aldehyde accumulation. These inventors suggest that enzymatic activity is inhibited in the presence of hydrogen cyanide (*Agricultural Biological Chemistry*, Vol. 46, page 1165 (1982)) generated in the partial disassociation of α-hydroxy nitrile in water together with the corresponding aldehyde or ketone (*Chemical Reviews*, Vol. 42, page 189 (1948)). The inventors solved the problem of aldehyde-induced enzyme inactivation by using microorganisms whose enzyme activity could be improved by adding a cyanide substance to the reaction mixture. The addition of a cyanide substance limited the disassociation of α-hydroxy nitrile to aldehyde and hydrogen cyanide.

With specific respect to the production of glycolic acid, glycolonitrile is known to reversibly disassociate to hydrogen cyanide and formaldehyde, either of which may inactivate enzyme activity. U.S. Pat. No. 3,940,316 describes a process for preparing an organic acid from the corresponding nitrile using bacteria with "nitrilasic" activity, and lists glycolonitrile as a substrate. In particular, this patent describes the use of *Bacillus, Bacteridium, Micrococcus*, and *Brevibacterium* for this purpose. Though described as having nitrilasic activity, *Brevibacterium* R312 is the only strain used in all of the U.S. Pat. No. 3,940,316 examples. *Brevibacterium* R312 is known to have nitrile hydratase and amidase activities, but no nitrilase activity (Tourneix et al., *Antonie van Leeuwenhoek*, 52:173–182 (1986)).

A method for preparing lactic acid, glycolic acid, and 2-hydroxyisobutyric acid by using a microorganism belonging to *Corynebacterium* spp. is disclosed in Japanese Patent Laid-open No. Sho 61-56086. JP 09028390 discloses a method for manufacturing glycolic acid from glycolonitrile by the action of *Rhodococcus* or *Gordona* hydrolase. Selectivity for glycolic acid is reported as almost 100%, without formation of glycolic acid amide. U.S. Pat. No. 6,037,155 discloses examples of methods for producing α-hydroxy acids from α-hydroxy nitriles, including glycolic acid. This disclosure acknowledges that not all microbial catalysts can produce high concentrations of glycolic acid due to the aforementioned problems and instructs that screening studies must be conducted in order to find industrially advantageous microorganisms. U.S. Pat. No. 6,037,155 specifically identifies *Variovorax* spp. and *Arthrobacter* spp. microorganisms that are resistant to the suppressing effect of α-hydroxy nitrile or α-hydroxy acid, have durable activity, and can produce the desired product at high concentration.

*Acidovorax facilis* 72W (ATCC 55746) is characterized by aliphatic nitrilase (EC 3.5.5.7) activity, as well as a combination of nitrile hydratase (EC 4.2.1.84) and amidase (EC 3.5.1.4) activities. U.S. Pat. No. 5,814,508 discloses heating a suspension of *Acidovorax facilis* 72W (ATCC 55746) in a suitable buffer at 35–70° C. for a short period of time to deactivate the undesirable nitrile hydratase and amidase activities of the whole-cell catalyst, without producing a significant decrease in the desired nitrilase activity.

The gene encoding the *A. facilis* 72W (ATCC 55746) nitrilase has been cloned and recombinantly expressed (WO 01/75077 corresponding to U.S. Pat. No. 6,870,038) and Chauhan et al., *Appl Microbiol Biotechnol*, 61:118–122 (2003)). The *A. facilis* 72W nitrilase converts α-hydroxynitriles to the corresponding α-hydroxycarboxylic acids in high yield (U.S. Pat. No. 6,383,786), including glycolic acid (U.S. Pat. No. 6,416,980). However, mutant nitrilases having improved nitrilase activity for the conversion of glycolonitrile to glycolic acid in high yield at up to 100% conversion would be very useful for reducing industrial production costs.

A method to produce glycolic acid using an enzyme catalyst economically requires the use of a catalyst that can convert glycolonitrile to glycolic acid in high concentrations, and with high catalyst productivity (kg glycolic acid/kg enzyme catalyst) and volumetric productivity (grams of glycolic acid/L/h). The enzyme catalyst may be employed in multiple consecutive batch reactions, or in a continuous reaction that employs constant addition of glycolonitrile and removal of glycolic acid; in either mode of operation, the catalyst activity and lifetime should be such that a high volumetric productivity and catalyst productivity are obtained, and in the case of batch reactions, the catalyst must be utilized in multiple reaction cycles without significant loss in enzyme activity between consecutive batch reactions. Mutant nitrilases having an improved nitrilase activity for glycolonitrile hydrolysis can provide improvements in volumetric productivity. Given the fact that the inactivating effect of free formaldehyde (and possibly other impurities) in the glycolonitrile reaction mixture will negatively affect all nitrilase catalysts to varying extents, improvements that stabilize enzyme activity under reaction conditions for hydrolysis of glycolonitrile (resulting in a relative increase in catalyst productivity) are also needed.

The problem to be solved is to provide a method to increase glycolic acid volumetric productivity using an enzyme catalyst exhibiting a significant improvement in nitrilase activity for hydrolysis of glycolonitrile. An additional problem to be solved is to provide a method to increase enzyme catalyst productivity and stability for glycolic acid production, thereby reducing enzyme catalyst cost and overall cost of manufacture.

SUMMARY OF THE INVENTION

The present invention provides methods for enzymatic production of glycolic acid from glycolonitrile. A process to produce glycolic acid from glycolonitrile is provided comprising:
(a) contacting glycolonitrile in a suitable aqueous reaction mixture with an enzyme catalyst comprising a polypeptide having nitrilase activity, said polypeptide having an amino acid sequence of SEQ ID NO: 6 with at least one amino acid substitution selected from the group consisting of:
 1) a substitution at amino acid residue 168 with lysine, methionine, threonine or valine; and
 2) a substitution at amino acid residue 201 with glutamine, glycine, histidine, lysine, asparagine, serine, alanine, cysteine, or threonine;
whereby glycolic acid is produced; and
(b) recovering the glycolic acid produced in (a) in the form of a salt or acid; wherein said enzyme catalyst provides at least a 1.5-fold increase in nitrilase activity relative to the nitrilase activity of the *Acidovorax facilis* 72W nitrilase when converting glycolonitrile to glycolic acid under identical reaction conditions.

In another aspect of the invention, an isolated nucleic acid molecule encoding a polypeptide having nitrilase activity is provided, said nucleic acid molecule encoding a polypeptide having an amino acid sequence of SEQ ID NO: 6 with at least one amino acid substitution selected from the group consisting of:
a) a substitution at amino acid residue 168 with methionine or threonine; and
b) a substitution at amino acid residue 201 with glutamine, glycine, histidine, lysine, asparagine, serine, alanine, cysteine, or threonine;
wherein said polypeptide provides at least a 1.5-fold increase in nitrilase activity relative to the nitrilase activity of the *Acidovorax facilis* 72W nitrilase when converting glycolonitrile to glycolic acid under identical reaction conditions.

In a further aspect, an isolated polypeptide is provided exhibiting a significant improvement in nitrilase activity when converting glycolonitrile to glycolic acid, said polypeptide comprising an amino acid sequence of SEQ ID NO: 6 with at least one amino acid substitution selected from the group consisting of:
a) a substitution at amino acid residue 168 with methionine or threonine; and
b) a substitution at amino acid residue 201 with glutamine, glycine, histidine, lysine, asparagine, serine, alanine, cysteine, or threonine;
wherein said polypeptide provides at least a 1.5-fold increase in nitrilase activity relative to the nitrilase activity of the *Acidovorax facilis* 72W nitrilase when converting glycolonitrile to glycolic acid under identical reaction conditions.

BRIEF DESCRIPTION OF THE SEQUENCE LISTING AND BIOLOGICAL DEPOSITS

The following sequence descriptions and sequences listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO: 1 is the nucleotide sequence of a primer 165 used to amplify the *Acidovorax facilis* 72W nitrilase coding sequence. The amplified PCR product was subsequently cloned into pUC19 (New England Biolabs, Beverly, Mass.; GenBank® L09137) to create plasmid pSW138.

SEQ ID NO: 2: is the nucleotide sequence of a primer 166 used to amplify the *Acidovorax facilis* 72W nitrilase coding sequence. The amplified PCR product was subsequently cloned into pUC19 (New England Biolabs, Beverly, Mass.; GenBank® L09137) to create plasmid pSW138.

SEQ ID NO: 3 is the nucleotide sequence of a primer used to amplify the *Acidovorax facilis* 72W nitrilase.

SEQ ID NO: 4 is the nucleotide sequence of a primer used to amplify the *Acidovorax facilis* 72W nitrilase.

SEQ ID NO: 5 is the nucleotide sequence of the *Acidovorax facilis* 72W nitrilase coding sequence comprising a change in the start codon from TTG to ATG to facilitate recombinant expression in *E. coli*.

SEQ ID NO: 6 is the deduced amino acid sequence of the *Acidovorax facilis* 72W nitrilase encoded by the nucleotide sequence of SEQ ID NO: 5 comprising a change in the start codon from TTG to ATG to facilitate recombinant expression in *E. coli*.

SEQ ID NO: 7 is the nucleotide sequence of an *A. facilis* 72W nitrilase mutant comprising a codon change which resulted in a single amino acid substitution at residue position 201 (L201Q; Leu→Gln).

SEQ ID NO: 8 is the deduced amino acid sequence of the mutant nitrilase (SEQ ID NO: 7) comprising a single amino acid substitution at residue position 201 (Leu201→Gln) of the *A. facilis* 72W nitrilase.

SEQ ID NO: 9 is the nucleotide sequence of an *A. facilis* 72W nitrilase mutant comprising a codon change which resulted in a single amino acid substitution at residue position 201 (L201A; Leu→Ala).

SEQ ID NO: 10 is the deduced amino acid sequence of the mutant nitrilase (SEQ ID NO: 9) comprising a single amino acid substitution at residue position 201 (Leu201→Ala) of the *A. facilis* 72W nitrilase.

SEQ ID NO: 11 is the nucleotide sequence of an *A. facilis* 72W nitrilase mutant comprising a codon change which resulted in a single amino acid substitution at residue position 201 (L201C; Leu→Cys).

SEQ ID NO: 12 is the deduced amino acid sequence of the mutant nitrilase (SEQ ID NO: 11) comprising a single amino acid substitution at residue position 201 (Leu201→Cys) of the *A. facilis* 72W nitrilase.

SEQ ID NO: 13 is the nucleotide sequence of an *A. facilis* 72W nitrilase mutant comprising a codon change which resulted in a single amino acid substitution at residue position 201 (L201T; Leu→Thr).

SEQ ID NO: 14 is the deduced amino acid sequence of the mutant nitrilase (SEQ ID NO: 13) comprising a single amino acid substitution at residue position 201 (Leu201→Thr) of the *A. facilis* 72W nitrilase.

SEQ ID NO: 15 is the nucleotide sequence of an *A. facilis* 72W nitrilase mutant comprising a codon change which resulted in a single amino acid substitution at residue position 201 (L201G; Leu→Gly).

SEQ ID NO: 16 is the deduced amino acid sequence of the mutant nitrilase (SEQ ID NO: 15) comprising a single amino acid substitution at residue position 201 (Leu201→Gly) of the *A. facilis* 72W nitrilase.

SEQ ID NO: 17 is the nucleotide sequence of an *A. facilis* 72W nitrilase mutant comprising a codon change which resulted in a single amino acid substitution at residue position 201 (L201 H; Leu→His).

SEQ ID NO: 18 is the deduced amino acid sequence of the mutant nitrilase (SEQ ID NO: 17) comprising a single amino acid substitution at residue position 201 (Leu201→His) of the *A. facilis* 72W nitrilase.

SEQ ID NO: 19 is the nucleotide sequence of an *A. facilis* 72W nitrilase mutant comprising a codon change which resulted in a single amino acid substitution at residue position 201 (L201 K; Leu→Lys).

SEQ ID NO: 20 is the deduced amino acid sequence of the mutant nitrilase (SEQ ID NO: 19) comprising a single amino acid substitution at residue position 201 (Leu201→Lys) of the *A. facilis* 72W nitrilase.

SEQ ID NO: 21 is the nucleotide sequence of an *A. facilis* 72W nitrilase mutant comprising a codon change which resulted in a single amino acid substitution at residue position 201 (L201 N; Leu→Asn).

SEQ ID NO: 22 is the deduced amino acid sequence of the mutant nitrilase (SEQ ID NO: 21) comprising a single amino acid substitution at residue position 201 (Leu201→Asn) of the *A. facilis* 72W nitrilase.

SEQ ID NO: 23 is the nucleotide sequence of an *A. facilis* 72W nitrilase mutant comprising a codon change which resulted in a single amino acid substitution at residue position 201 (L201S; Leu→Ser).

SEQ ID NO: 24 is the deduced amino acid sequence of the mutant nitrilase (SEQ ID NO: 23) comprising a single amino acid substitution at residue position 201 (Leu201→Ser) of the *A. facilis* 72W nitrilase.

SEQ ID NO: 25 is the nucleotide sequence of an *A. facilis* 72W nitrilase mutant comprising a codon change which resulted in a single amino acid substitution at residue position 168 (F168K; Phe→Lys).

SEQ ID NO: 26 is the deduced amino acid sequence of the mutant nitrilase (SEQ ID NO: 25) comprising a single amino acid substitution at residue position 168 (Phe168→Lys) of the *A. facilis* 72W nitrilase.

SEQ ID NO: 27 is the nucleotide sequence of an *A. facilis* 72W nitrilase mutant comprising a codon change which resulted in a single amino acid substitution at residue position 168 (F168M; Phe→Met).

SEQ ID NO: 28 is the deduced amino acid sequence of the mutant nitrilase (SEQ ID NO: 27) comprising a single amino acid substitution at residue position 168 (Phe168→Met) of the *A. facilis* 72W nitrilase.

SEQ ID NO: 29 is the nucleotide sequence of an *A. facilis* 72W nitrilase mutant comprising a codon change which resulted in a single amino acid substitution at residue position 168 (F68T; Phe→Thr).

SEQ ID NO: 30 is the deduced amino acid sequence of the mutant nitrilase (SEQ ID NO: 29) comprising a single amino acid substitution at residue position 168 (Phe168→Thr) of the *A. facilis* 72W nitrilase.

SEQ ID NO: 31 is the nucleotide sequence of an *A. facilis* 72W nitrilase mutant comprising a codon change which resulted in a single amino acid substitution at residue position 168 (F168V; Phe→Val).

SEQ ID NO: 32 is the deduced amino acid sequence of the mutant nitrilase (SEQ ID NO: 31) comprising a single amino acid substitution at residue position 168 (Phe168→Val) of the *A. facilis* 72W nitrilase.

SEQ ID NO: 33 is the nucleotide sequence of an *A. facilis* 72W nitrilase mutant comprising a codon change which resulted in a single amino acid substitution at residue position 168 (T210A; Thr→Ala).

SEQ ID NO: 34 is the deduced amino acid sequence of the mutant nitrilase (SEQ ID NO: 33) comprising a single amino acid substitution at residue position 210 (Thr210→Ala) of the *A. facilis* 72W nitrilase.

SEQ ID NO: 35 is the nucleotide sequence of an *A. facilis* 72W nitrilase mutant comprising a codon change which resulted in a single amino acid substitution at residue position 168 (T210C; Thr→Cys).

SEQ ID NO: 36 is the deduced amino acid sequence of the mutant nitrilase (SEQ ID NO: 35) comprising a single amino acid substitution at residue position 210 (Thr210→Cys) of the *A. facilis* 72W nitrilase.

SEQ ID NO: 37 is the nucleotide sequence of an *A. facilis* 72W nitrilase gene expressed in *E. coli* SS1001 (ATCC PTA-1177; U.S. Pat. No. 6,870,038 herein incorporated by reference).

SEQ ID NO: 38 is the deduced amino acid sequence of the *A. facilis* 72W nitrilase (SEQ ID NO: 33) expressed in *E. coli* SS1001 (ATCC PTA-1177).

The following biological deposits have been made under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| *Acidovorax facilis* 72W | ATCC 55746 | 8 Mar. 1996 |
| *E. coli* SS1001 | ATCC PTA-1177 | 11 Jan. 2000 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The stated problems have been solved by providing a process to prepare glycolic acid from the corresponding glycolonitrile in high yields and at high concentration using *Acidovorax facilis* 72W nitrilase mutants having improved nitrilase activity. The methods that solve the stated problems include: 1) use of *Acidovorax facilis* 72W nitrilase mutants having improved nitrilase activity and/or improved catalyst productivity for converting glycolonitrile to glycolic acid, and 2) methods to improve catalyst stability and/or productivity under reaction conditions for the conversion of glycolonitrile to glycolic acid. The methods to improve catalyst stability/productivity under reaction conditions for the conversion of glycolonitrile to glycolic acid include 1) the use of additives to stabilize enzyme catalyst activity, 2) running the reaction under substantially oxygen free conditions, and 3) controlling the feed rate of glycolonitrile to the reaction mixture so that a targeted concentration of glycolonitrile is maintained.

Definitions:

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent, error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the term "recovering" means isolating, purifying, or transferring the product formed by the present process. Methods to isolate and purify the product(s) from the reaction mixture are well known in the art may include, but are not limited to selective precipitation, crystallization, filtration, reactive solvent extraction, ion exchange, electrodialysis, polymerization, distillation, thermal decomposition, alcoholysis, and combinations thereof. In one embodiment, the term "recovering" may also include transferring the product mixture (typically after filtering out the enzyme catalyst) to another reaction to create one or more additional products.

As used herein, the term "enzyme catalyst" or "microbial cell catalyst" refers to a catalyst that is characterized by a nitrilase activity (i.e., comprises at least one polypeptide having nitrilase activity) for converting glycolonitrile to glycolic acid and ammonia. The enzyme catalyst may be in the form of a whole microbial cell, permeabilized microbial cell(s), one or more cell components of a microbial cell extract, partially purified enzyme, or purified enzyme. The enzyme catalyst can be free (unimmobilized) or immobilized in or on a soluble or insoluble support. As used herein, "recycled enzyme catalyst" refers to an enzyme catalyst that is reused as an enzyme catalyst in batch reactions.

As used herein, the terms "catalyst productivity" and "enzyme catalyst productivity" refer to the total amount of product produced per gram of catalyst. In the present invention, the catalyst is a nitrilase enzyme (EC 3.5.5.7) and the product formed is glycolic acid and/or ammonium glycolate (depending upon the pH of the reaction). In general, the present methods are conducted under essentially pH neutral conditions so that the glycolic acid produced is predominantly in the form of the corresponding salt of glycolic acid (i.e. ammonium glycolate). Generally, in batch reactions with catalyst recycle, the catalyst activity decreases with each recycle reaction (enzyme inactivation).

As used herein, the terms "*Acidovorax facilis*", "*Acidovorax facilis* 72W", and "*A. facilis*" are used interchangeably and refer to *Acidovorax facilis* 72W deposited to the American Type Culture Collection (an international depository authority) having accession number 55746 ("ATCC 55746").

As used herein, the terms "*Escherichia coli*" and "*E. coli*" are used interchangeably. Several strains of *E. coli* suitable for recombinant expression are described herein including, but not limited to *E. coli* MG1655 having international depository number ATCC 47076, *E. coli* FM5 having international depository number ATCC 53911, *E. coli* W3110 having international depository number ATCC 27325, *E. coli* MC4100 having international depository number ATCC 35695, and *E. coli* W1485 having international depository number ATCC 12435. In one embodiment, suitable *Escherichia coli* strains include *E. coli* FM5 (ATCC 53911) and *E. coli* MG1655 (ATCC 47076).

As used herein, the terms "*E. coli* SS1001" or "SS1001" refer to a transformed *E. coli* strain expressing the *Acidovorax facilis* 72W nitrilase having ATCC Accession No. PTA-1177 (U.S. Pat. No. 6,870,038; herein incorporated in its entirety by reference). The recombinantly expressed *E. coli* SS1001 nitrilase (SEQ ID NO: 38) contains 2 minor sequence changes in comparison to the wild-type 72W nitrilase sequence (SEQ ID NO: 6). The start codon was changed from GTG to ATG to facilitate recombinant expression and an artifact was introduced during cloning that resulted in a single amino acid change near the C-terminal (Pro367 [CCA]→Ser [TCA]).

As used herein, the term "glycolonitrile" is abbreviated as "GLN" and is synonymous with hydroxyacetonitrile, 2-hydroxyacetonitrile, hydroxymethyl nitrile, and all other synonyms of CAS Registry Number 107-16-4.

As used herein, the term "glycolic acid" is abbreviated as "GLA" and is synonymous with hydroxyacetic acid, hydroxyethanoic acid, and all other synonyms of CAS Registry Number 79-14-1. The glycolic acid produced by the present process may in the form of the protonated carboxylic acid and/or the corresponding ammonium salt.

As used herein, the term "ammonium glycolate" is abbreviated "NH$_4$GLA".

As used herein, the term "glycolide" refers to the compound of CAS Registry Number 502-97-6.

As used herein, the terms "suitable aqueous glycolonitrile reaction mixture" and "suitable aqueous reaction mixture" refer to the materials and water in which the glycolonitrile and enzyme catalyst come into contact.

As used herein, the term "nitrilase catalyst" refers herein to an enzyme catalyst that is characterized by nitrilase activity (EC 3.5.5.7). A nitrilase enzyme directly converts an aliphatic nitrile to the corresponding carboxylic acid, without forming the corresponding amide as intermediate (Equation 1).

Equation 1

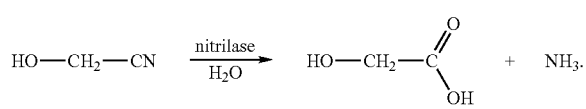

As used herein, the terms "improved nitrilase", "mutant nitrilase", "*Acidovorax facilis* 72W mutant nitrilase", and "protein engineered nitrilase" will be used interchangeably to refer to the present nitrilases having significantly improved nitrilase activity towards the conversion of glycolonitrile to glycolic acid in comparison to the activity of the *A. facilis* 72W nitrilase under identical reaction conditions. In one embodiment, the improvement in nitrilase activity can be determined by comparing the nitrilase activity of present mutant nitrilase catalysts against the nitrilase activity of the native *A. facilis* 72W nitrilase when recombinantly expressed (using identical expression systems) and assayed under essentially identical reaction conditions. SDS-PAGE analysis indicated that protein expression levels between the present mutants and their respective controls (SEQ ID NO: 6) were essentially identical. As such, improvements in nitrilase activity are attributed to structural modifications to the native *A. facilis* 72W nitrilase.

The term "nitrilase activity" refers to the enzyme activity per unit mass (for example, milligram) of protein, dry cell weight, or bead weight (immobilized catalyst) when converting glycolonitrile to glycolic acid (or the corresponding ammonium glycolate). Comparisons in nitrilase activity were measured proportional to the dry cell weight or bead weight. Since nitrilase expression levels between the *A. facilis* 72W controls (SEQ ID NO: 6) and the improved mutants were indistinguishable as quantified using laser densitometry analysis of an SDS-PAGE gel, comparisons and reported improvements in nitrilase activity were measured relative to dry cell weight (dcw) or bead weight (bw).

As used herein, the term "one unit of enzyme activity" or "one unit of nitrilase activity" or "U" is defined as the amount of enzyme activity required for the production of 1 μmol of glycolic acid product per minute (GLA U/g dry cell weight or bead weight) at a specified temperature (e.g. 25° C.).

As used herein, the terms "relative nitrilase activity", "improved nitrilase activity", and "relative improvement in nitrilase activity" refers to the nitrilase activity expressed as a multiple (or fraction) of a reference (control) nitrilase activity. The present mutant nitrilases exhibit a significant improvement in nitrilase activity relative to the nitrilase activity observed with native *Acidovorax facilis* 72W nitrilase. In the present invention, a "significant improvement" in relative nitrilase activity is an improvement of at least 1.5-fold higher nitrilase activity in comparison to the nitrilase activity of the control (*A. facilis* 72W nitrilase; SEQ ID NO: 6) under identical reaction conditions. In another embodiment, the improvement is at least 2-fold higher nitrilase activity in comparison to the nitrilase activity of the control under identical reaction conditions. In a further embodiment, the improvement is at least 4-fold higher nitrilase activity in comparison to the nitrilase activity of the control under identical reaction conditions.

As used herein, the term "initial reaction rate" is a measurement of the rate of conversion of glycolonitrile to glycolic acid under the stated reaction conditions, where the measurement of reaction rate begins upon the initial addition of glycolonitrile to the reaction mixture, and where the reaction rate is measured over a period of time where the concentration of glycolonitrile remains above ca. 50 millimolar (mM) during the course of the reaction. The reaction rate is measured as the change in concentration of glycolic acid produced per unit time (e.g., mole glycolic acid/L/min or mM glycolic acid/hour).

As used herein, the terms "recombinant organism", "transformed host", "transformant", "transgenic organism", and "transformed microbial host" refer to a host organism having been transformed with heterologous or foreign DNA.

The recombinant organisms of the present invention express foreign coding sequences or genes that encode active nitrilase enzyme. "Transformation" refers to the transfer of a DNA fragment into the host organism. The transferred DNA fragment can be chromosomally or extrachromosomally incorporated (i.e., via a vector) into the host organism. As used herein, the term "transformation cassette" refers to a specific fragment of DNA containing a set of genetic elements conveniently arranged for insertion into a host cell, usually as part of a plasmid. As used herein, the term "expression cassette" refers to a specific fragment of DNA containing a set of genetic elements conveniently arranged for insertion into a host cell, usually as part of a plasmid, that also allows for enhanced gene expression in the host.

As used herein, the terms "nucleic acid fragment" and "nucleic acid molecule" refer to DNA molecule that may encode an entire gene, coding sequence, and/or regulatory sequences preceding (5', upstream) or following (3', downstream) the coding sequence. In one aspect, the present nucleic acid molecules encode for polypeptides having nitrilase activity.

As used herein, the term "gene" refers to a nucleic acid molecule that expresses a specific protein. As used herein, it may or may not including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, the term "coding sequence" refers to a DNA sequence that codes for a specific amino acid sequence. As used herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. Promoters that cause a gene to be expressed in most cell types at most times or under most environmental conditions are commonly referred to as "constitutive promoters". Promoters that cause a gene to be expressed only in the presence of a particular compound or environmental condition are commonly referred to as "inducible promoters". Since in most cases the exact boundaries of regulatory sequences have not been completely defined, DNA fragments of different lengths may have identical promoter activity.

As used herein, the term "operably linked" refers to the association of nucleic acid sequences on a single nucleic acid molecule so that the function of one sequence is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

As used herein, the term "3' non-coding sequences" refers to DNA sequences located downstream of a coding sequence and include polyadenylation recognition sequences (normally limited to eukaryotes) and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

The skilled artisan is well aware of the "codon-bias" exhibited by a specific host cell in using nucleotide codons to specify a given amino acid. Therefore, when synthesizing a gene for improved expression in a host cell, it is desirable to design the gene such that its codon usage reflects the preferred codon bias of the host cell. A survey of genes derived from the host cell where sequence information is available can determine its codon bias. Codon-optimization is well known in the art and has been described for various systems including, but not limited to yeast (Outchkourov et al., *Protein Expr Purif*, 24(1): 18–24 (2002)) and *E. coli* (Feng et al., *Biochemistry*, 39(50): 15399–15409 (2000)).

*Acidovorax facilis* 72W (ATCC 55746) Nitrilase

The *A. facilis* 72W nitrilase (EC 3.5.5.1) is a robust catalyst for producing carboxylic acids from aliphatic or aromatic nitriles (WO 01/75077; U.S. Pat. No. 6,870,038; and Chauhan et al., supra). It has also been shown to catalyze the conversion of α-hydroxynitriles (i.e., glycolonitrile) to α-hydroxycarboxylic acids (i.e., glycolic acid) (see U.S. Pat. No. 6,383,786 and U.S. Pat. No. 6,416,980; hereby incorporated in their entirety by reference).

All known nitrilases, including the *A. facilis* 72W nitrilase, have a nucleophilic cysteine in the enzyme active site (Cowan et al., *Extremophiles*, 2:207–216 (1998); Pace, H. and Brenner, C., *Genome Biology*, 2(1): reviews 1–9 (2001); and Chauhan et al., supra) and all are susceptible to inactivation by thiol reagents (1.0 mM concentrations of copper chloride, silver nitrate, mercuric acetate, or ferric chloride each produced major decreases in *A. facilis* 72W nitrilase enzyme activity). Cysteine residues are also capable of being irreversibly oxidized to sulfinic acids, resulting in a loss of enzyme activity. Despite the sensitivity of nitrilase enzymes to various inactivating mechanisms, immobilized *A. facilis* 72W cells are robust, capable of retaining much of their nitrilase activity after numerous recycle reactions (U.S. Pat. No. 6,870,038).

Sequence comparisons of the *A. facilis* 72W nitrilase to other bacterial nitrilases have been reported (U.S. Pat. No. 6,870,038; Chauhan et al., supra). The 72W nitrilase has several conserved signature domains including a 16-amino acid region near the amino terminus (amino acid residues 40–55 of SEQ ID NO:6) and the catalytic region (amino acid residues 160–173 of SEQ ID NO:6) containing the essential cysteine residue. This cysteine residue (Cys164 of SEQ ID NO:6), along with conserved glutamic acid (Glu48 of SEQ ID NO:6) and lysine residues (Lys130 of SEQ ID NO:6), form the catalytic triad motif found in all nitrilases (Pace, H., and Brenner, C., supra). Despite some structural similarities conserved among the reported nitrilases, substrate specificity varies widely (O'Reilly, C. and Turner, P., *J Appl Microbiol*, 95:1161–1174 (2003)).

Mutant Nitrilase Enzyme Properties

Several mutant nitrilases derived from the *A. facilis* 72W nitrilase have been previously reported (U.S. Ser. No. 10/919182; hereby incorporated in its entirety by reference). In U.S. Ser. No. 10/919182, various mutant nitrilases were selected and screened for relative improvements (relative to the activity of recombinantly expressed, native 72W nitrilase) in nitrilase activity for converting 3-hydroxynitriles to 3-hydroxyacids (i.e. 3-hydroxybutyronitrile and 3-hydroxyvaleronitrile).

The expression system used with the nitrilase mutants described in U.S. Ser. No. 10/919182 is based on the plasmid pTrcHis2-TOPO® and the *E. coli* host TOP10 (both from Invitrogen, La Jolla, Calif.). The activity of nitrilase mutants F168L (residue 168 changed from Phe to Leu in SEQ ID NO: 6), F168V (residue 168 changed from Phe to Val; SEQ ID NO: 32), F168K (residue 168 changed from Phe to Lys; SEQ ID NO: 26), T210A (residue 210 changed form Thr to Ala; SEQ ID NO: 34), and T210C (residue 210 change from Thr to Cys; SEQ ID NO: 36) were compared to the native enzyme ("control"; SEQ ID NO: 6) in the same expression system using the method described in Example 2. Mutants F168L, T210A, and T210C, which were initially identified as possibly having significantly improved nitrilase activity when converting GLN to GLA, were later found to have similar nitrilase activity to the native 72W nitrilase. Unexpectedly, two of the mutant nitrilases (F168K, Phe168→Lys; F168V, Phe168→Val) described in U.S. Ser. No. 10/919182 (herein represented by SEQ ID NOs: 26 and 32; respectively) also exhibited a significant improvement in nitrilase activity when converting glycolonitrile (a 2-hydroxynitrile) to glycolic acid. However, the other mutant nitrilases described in U.S. Ser. No. 10/919182 (e.g. T210A, SEQ ID NO: 34; T210C, SEQ ID NO: 36) did not show a significant improvement in nitrilase activity when converting glycolonitrile to glycolic acid.

As described in the present examples, error-prone PCR and targeted saturation mutagenesis was used to randomly mutate the native 72W nitrilase coding sequence (SEQ ID NO: 5). Mutations that resulted in an amino acid substitution at amino acid residue positions 168 (phenylalanine in the wild type sequence) and 201 (leucine in the wild type sequence) appeared to increase nitrilase activity significantly. As used herein, the term "amino acid residue position" refers to the amino acid found at a particular location relative to the reference sequence (SEQ ID NO: 6) as measured from the N-terminal methionine residue. Targeted saturation mutagenesis was conducted to evaluate all amino acid substitutions at both residue positions (168 and 201). Several additional mutants were identified having a significant improvement nitrilase activity of converting glycolonitrile to glycolic acid (e.g. in the form of the ammonium glycolate salt under the present reaction conditions). The present mutant nitrilases are comprised of at least one amino acid substitution relative to the *Acidovorax facilis* 72W nitrilase sequence (SEQ ID NO: 6). As such, the amino acid sequence of each of the present mutant nitrilases have an amino acid sequence SEQ ID NO: 6 (reference sequence) with at least one amino acid substitution as described herein.

In one embodiment, suitable mutant nitrilases useful in the present process comprise a nucleotide sequence encoding a polypeptide having an amino acid sequence of SEQ ID NO: 6 with at least one amino acid substitution selected from the group consisting of:
  a) a substitution of lysine, methionine, threonine, or valine at amino acid position 168; and
  b) a substitution of glutamine, glycine, histidine, lysine, asparagine, serine, alanine, cysteine, or threonine at amine acid position 201;

wherein said polypeptide provides at least a 1.5-fold improvement in nitrilase activity when converting glycolonitrile to glycolic acid.

In another embodiment, suitable mutant nitrilase useful in the present process have an amino acid sequence selected from the group consisting of SEQ ID NOs: 8, 10, 12, 14, 16, 18, 20, 22, 24, 26, 28, 30, and 32. In yet another embodiment, suitable mutant nitrilase useful in the present process have a nucleotide sequence selected from the group consisting of SEQ ID NOs: 7, 9, 11, 13, 15, 17, 19, 21, 23, 25, 27, 29, and 31.

In one aspect, the present invention includes an isolated nucleic acid molecule encoding a polypeptide having nitrilase activity, said polypeptide having an amino acid sequence of SEQ ID NO: 6 with at least one amino acid substitution selected from the group consisting of:
  a) a substitution at amino acid residue 168 with methionine or threonine; and
  b) a substitution at amino acid residue 201 with glutamine, glycine, histidine, lysine, asparagine, serine, alanine, cysteine, or threonine; wherein said polypeptide provides at least a 1.5-fold increase in nitrilase activity relative to the nitrilase activity of the *Acidovorax facilis* 72W nitrilase when converting glycolonitrile to glycolic acid under identical reaction conditions.

In another aspect, the present invention includes an isolated nucleic acid molecule encoding a polypeptide having an amino acid sequence selected from the group consisting of SEQ ID NOs: 8, 10, 12, 14, 16, 18, 20, 22, 24, 28, and 30. In a further aspect, the present invention includes an isolated nucleic acid molecule having a nucleic acid sequence selected from the group consisting of SEQ ID NOs: 7, 9, 11, 13, 15, 17, 19, 21, 23, 27, and 29.

In one embodiment, the present invention includes an isolated polypeptide having nitrilase activity, said polypeptide having an amino acid sequence of SEQ ID NO: 6 with at least one amino acid substitution selected from the group consisting of:
  a) a substitution at amino acid residue 168 with methionine or threonine; and
  b) a substitution at amino acid residue 201 with glutamine, glycine, histidine, lysine, asparagine, serine, alanine, cysteine, or threonine; wherein said polypeptide provides at least a 1.5-fold increase in nitrilase activity relative to the nitrilase activity of the *Acidovorax facilis* 72W nitrilase when converting glycolonitrile to glycolic acid under identical reaction conditions.

In another embodiment, the present invention includes a polypeptide having nitrilase activity, said polypeptide having an amino acid sequence selected from the group consisting of SEQ ID NOs: 8, 10, 12, 14, 16, 18, 20, 22, 24, 28, and 30.

Nitrilase activity was calculated by dividing the measured units of activity (U) by catalyst weight. The catalyst weight can be measured in terms of purified protein weight, wet cell weight, dry cell weight or weight of the immobilized catalyst (i.e., using carrageenan and/or GA/PEI-crosslinked catalyst/alginate beads). In the present invention, the nitrilase activity was reported as units of activity per gram of dry cell weight (U/g DCW) or units of activity per gram of catalyst bead (immobilized catalyst comparisons). With nitrilase activity comparisons based on dry cell weight as the unit catalyst weight, the level of nitrilase protein production must be considered. The expression levels of nitrilase enzyme between the various transformants and their respective controls were measured and observed to be essentially identical (i.e., when compared in the same genetic background). Thus, improvements in the reported nitrilase activity for the various mutants were attributed to structural modifications to the enzymes.

The coding sequences of the mutant nitrilases (and also of the *A. facilis* 72W (ATCC 55746) nitrilase control) were expressed in identical vector backgrounds (pTrcHis2-TOPO® or pUC19) and hosts: *E. coli* TOP10 (Invitrogen), *E. coli* FM5 (ATCC 53911), or *E. coli* MG1655 (ATCC 47076). Relative improvements were based on comparisons to the appropriate control using the same vector and host background. SDS-PAGE analyses (as quantified using laser densitometry) demonstrated that nitrilase protein expression levels in each mutant (and control) were essentially equal (as expected due to the identical expression system and host used). The relative enzyme activity was reported as the fold increase in nitrilase activity measured for the various mutant catalysts relative to the nitrilase activity measured in the respective *E. coli* control transformant expressing the *A. facilis* 72W nitrilase (SEQ ID NO: 6).

For unimmobilized catalysts, nitrilase activity of the mutant nitrilases (U/g dry cell weight) was determined by measuring the rate of conversion of glycolonitrile to glycolic acid (μmol GLA/min) at 25° C. per gram of dry cell weight. For immobilized catalyst comparisons, activity was determined by measuring the rate of conversion of glycolonitrile to glycolic acid (μmol GLA/min) at 25° C. and reported as units of nitrilase activity per gram of immobilized cell catalyst bead (U/g bead). One unit of nitrilase activity (U) is equivalent to production of 1 micromole glycolic acid/min at 25° C. (μmol GLA/min).

For a particular mutant nitrilase, point substitution mutations within the DNA coding region and the resulting amino acid change are specified with reference to the *Acidovorax facilis* 72W amino acid sequence (SEQ ID NO:6), using one of the following formats:

1. Extended format: the wild-type amino acid is provided (using the standard 3-letter abbreviation) along with the corresponding amino acid residue position within SEQ ID NO:6 followed by the new amino acid found within the mutant at the same residue position. For example, "Phe168 to Lys" or "Phe168→Lys" describes a mutation in the SEQ ID NO:6 at amino acid residue position 168 where phenylalanine was changed to lysine as a result of the mutation.
2. Short-hand format: the wild-type amino acid (denoted by the standard single letter abbreviation) is followed by the amino acid residue position of SEQ ID NO:6 followed by the mutant amino acid (also denoted by the standard single letter abbreviation). For example, "F168K" describes a mutation in SEQ ID NO:6 at amino acid residue position 168 where phenylalanine was changed to lysine as a result of the mutation.

Hydrolysis of Glycolonitrile to Glycolic Acid Using a Nitrilase Catalyst

The hydrolysis reaction was performed by contacting an enzyme catalyst with an aqueous reaction mixture comprising glycolonitrile. Whole recombinant microbial cells (expressing the present mutant nitrilases) can be used as an enzyme catalyst without any pretreatment. The microbial cell catalyst can be added directly to a reaction mixture, or maintained separately from the bulk reaction mixture using hollow-fiber membrane cartridges or ultrafiltration membranes. Alternatively, the microbial cells can be immobilized in a polymer matrix (e.g., carrageenan or polyacrylamide gel (PAG) particles) or on an insoluble solid support (e.g., celite) to facilitate recovery and reuse of the enzyme catalyst (U.S. Pat. No. 6,870,038). Purified or partially-purified enzyme(s) can also be isolated from the whole cells and used directly as a catalyst, or the enzyme(s) can be immobilized in a polymer matrix or on an insoluble support. Methods for the immobilization of cells or for the isolated enzymes have been widely reported and are well known to those skilled in the art (Methods in Biotechnology, Vol. 1: *Immobilization of Enzymes and Cells*; Gordon F. Bickerstaff, Editor; Humana Press, Totowa, N.J., USA; 1997). The immobilization of the *A. facilis* 72W nitrilase catalyst has previously been reported (U.S. Pat. No. 6,870,038).

The concentration of enzyme catalyst in the aqueous reaction mixture depends on the specific activity of the enzyme catalyst and is chosen to obtain the desired rate of reaction. The wet cell weight of the microbial cells used as catalyst in hydrolysis reactions typically ranges from 0.001 grams to 0.250 grams of wet cells per mL of total reaction volume, preferably from 0.002 grams to 0.050 grams of wet cells per mL.

The temperature of the hydrolysis reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C. The microbial cell catalyst suspension may be prepared by suspending the cells in distilled water, or in a aqueous solution of a buffer which will maintain the initial pH of the reaction between about 5.0 and about 10.0, preferably between about 5.5 and about 8.0, more preferably between about 5.5 and about 7.7, and most preferably about 6.0 to about 7.7. As the reaction proceeds, the pH of the reaction mixture may change due to the formation of an ammonium salt of the carboxylic acid from the corresponding nitrile functionality. The reaction can be run to complete conversion of glycolonitrile with no pH control, or a suitable acid or base can be added over the course of the reaction to maintain the desired pH.

Glycolonitrile was found to be completely miscible with water in all proportions at 25° C. In cases where reaction conditions are chosen such that the solubility of the substrate (i.e. an α-hydroxynitrile) is also dependent on the temperature of the solution and/or the salt-concentration (buffer or product glycolic acid ammonium salt, also known as ammonium glycolate) in the aqueous phase, the reaction mixture may initially be composed of two phases: an aqueous phase containing the enzyme catalyst and dissolved α-hydroxynitrile, and an organic phase (the undissolved α-hydroxynitrile). As the reaction progresses, the α-hydroxynitrile dissolves into the aqueous phase, and eventually a single phase product mixture is obtained. The reaction may also be run by adding the α-hydroxynitrile to the reaction mixture at a rate approximately equal to the enzymatic hydrolysis reaction rate, thereby maintaining a single-phase aqueous reaction mixture, and avoiding the potential problem of substrate inhibition of the enzyme at high starting material concentrations.

Glycolic acid may exist in the product mixture as a mixture of the protonated carboxylic acid and/or its corresponding ammonium salt (dependent on the pH of the product mixture), and may additionally be present as a salt of the carboxylic acid with any buffer that may additionally be present in the product mixture. The glycolic acid product may be isolated from the reaction mixture as the protonated carboxylic acid, or as a salt of the carboxylic acid, as desired.

The final concentration of glycolic acid in the product mixture at complete conversion of glycolonitrile may range from 0.001 M to the solubility limit of the glycolic acid product. In one embodiment, the concentration of glycolic acid will range from about 0.10 M to about 9.0 M. In another embodiment, the concentration of glycolic acid will range from about 0.2 M to about 4.0 M. Glycolic acid may be isolated from the product mixture (after removal of the catalyst) by adjusting the pH of the reaction mixture to between about 1.0 and about 3.0 with a suitable mineral acid, such as concentrated hydrochloric acid or sulfuric acid, and extracting the glycolic acid with a suitable organic solvent. In one embodiment, the suitable organic solvent is a mixture of Alamine® 336 (a tertiary alkylamine wherein the alkyl groups are $C_8$ to $C_{10}$ in length; Cognis Corp., Cincinnati, Ohio) with one or more diluents selected from the group consisting of methyl isobutyl ketone, 1-octanol, 1-decanol, toluene, xylene (mixed), kerosene, methyl t-butyl ether, ethyl ether, and dichloromethane (see copending U.S. Provisional Patent Application 60/638128; herein incorporated by reference). The glycolic acid can be back-extracted from the organic solvent using water.

In one embodiment, the organic extract is saturated with sodium chloride, and is contacted with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation.

In another embodiment, the glycolic acid can be isolated directly from the ammonium glycolate using direct deammoniation and/or other purification methods including, but not limited to concentration, crystallization, reactive solvent extraction, ion exchange, electrodialysis, glycolysis, polymerization, distillation, thermal decomposition (salt cracking), alcoholysis, and combinations thereof (see copending U.S. Provisional Patent Applications 60/638148 and 60/638126; each application herein incorporated by reference in its entirety).

Microbial Expression

The present nitrilase mutants may be produced in heterologous host cells, preferably in microbial hosts. Particularly useful in the present invention will be cells that are readily adaptable to large-scale fermentation methods. Such organisms are well known in the art of industrial bioprocessing, examples of which may be found in *Recombinant Microbes for Industrial and Agricultural Applications*, Murooka et al., eds., Marcel Dekker, Inc., New York, N.Y. (1994), and include fermentative bacteria as well as yeast and filamentous fungi. Host cells may include, but are not limited to *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. Particularly preferred is *E. coli*. Examples of suitable *E. coli* host cells in which a mutant nitrilase gene can be expressed include, but are not limited to, host cells specified herein and MG1655 (ATCC 47076), FM5 (ATCC 53911), W3110 (ATCC 27325), MC4100 (ATCC 35695), W1485 (ATCC 12435), and their derivatives. In another aspect, the preferred *E. coli* host strains are MG1655 (ATCC 47076) or FM5 (ATCC 53911), Heterologous expression of the *A. facilis* 72W nitrilase has previously been reported (Chauhan et al., supra and U.S. Pat. No. 6,870,038). Chauhan et al. report an *E. coli* strain (*E. coli* SS1001 (ATCC PTA-1177)) that expressed active *A. facilis* 72W nitrilase (SEQ ID NO: 38). The coding sequence of the recombinantly expressed (*E. coli* SS1001) nitrilase contained two minor sequence changes in comparison to the wild-type 72W nitrilase sequence (SEQ ID NOs: 5 and 6). The start codon was changed from GTG to ATG to facilitate recombinant expression and an artifact was introduced during cloning that resulted in a single amino acid change near the C-terminal (Pro367 [CCA]→Ser [TCA]).

Recombinant expression in an industrially-suitable host has several advantages. First, the genetic toolbox for many of the commonly used production hosts is usually well developed in comparison to the genetic tools available for many of the microorganisms from which the gene of interest was obtained. Recombinant expression in these hosts is normally more cost effective than expression in the native host. For example, it has been shown that *A. facilis* 72W cells grow on glycerol, a relatively expensive carbon substrate, when grown by fermentation, and have not been successfully grown using inexpensive glucose. In contrast, *E. coli* transformants can be grown on glucose to the same cell density as *A. facilis* 72W cells in about half the time, significantly reducing biocatalyst production costs (U.S. Pat. No. 6,870,038).

Microbial expression systems and expression vectors containing regulatory sequences that direct high level expression of foreign proteins are well-known to those skilled in the art. These could be used to construct chimeric genes for production of the gene products of the present mutant nitrilases. These chimeric genes could then be introduced into appropriate microorganisms via transformation to provide high level expression of the mutant nitrilase enzymes. The nucleic acid molecules of the present invention are used to produce gene products having enhanced or altered nitrilase activity levels relative to that of the native *A. facilis* 72W nitrilase. In one aspect, the polypeptides encoded by the present mutant genes provide at least a 1.5 fold improvement in nitrilase activity (as compared to the activity of the *A. facilis* 72W nitrilase represented by SEQ ID NO: 6) for converting glycolonitrile to glycolic acid.

Chimeric genes will be effective in altering the properties of a host cell. For example, introducing at least one copy of chimeric genes encoding the present nitrilases under the control of the appropriate promoters into a host cell gives the host cell an improved ability to convert glycolonitrile to glycolic acid. The chimeric genes of the instant invention will comprise suitable regulatory sequences useful for driving gene expression of the present mutant nitrilase sequences. Regulatory sequences will include, but are not limited to promoters, translation leader sequences, and ribosomal binding sites. It is preferred if these sequences are derived from the host organism; however, the skilled person will recognize that heterologous regulatory sequences may also be used.

Chimeric genes can be introduced into an appropriate host by cloning it into a suitable expression vector. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the coding sequence that harbors transcriptional initiation controls and a region 3' of the DNA fragment which controls transcriptional termination. It is most preferred when both control regions are derived from genes homologous to the host cell, although such control regions need not be derived from the genes native to the specific species chosen as a production host.

In one embodiment, the regulatory sequences will include a promoter. Promoters may be constitutive or inducible. Inducible promoters are generally responsive to a specific stimulus (e.g., IPTG or lactose inducing the lac promoter). Inducible promoters may be responsive to a variety of stimuli, including, chemicals, growth cycle, changes in temperature, changes in pH and changes in osmolarity, to name only a few.

Initiation control regions or promoters that are useful to drive expression of the present mutant nitrilases in the desired host cell are numerous and familiar to those skilled in the art, including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, $P_{BAD}$, npr, and trc (particularly useful for expression in *Escherichia coli*). Additional examples of promoters particularly suitable for driving expression in *E. coli* include, but are not limited to the tryptophan operon promoter Ptrp of *E. coli*, a lactose operon promoter Plac of *E. coli*, a Ptac promoter of *E. coli*, a phage lambda right promoter $P_R$, a phage lambda left promoter $P_L$, a T7 promoter, and a promoter of the GAP gene from *Pichia pastoris*, or is at least one promoter isolated from the group of microorganisms selected from the group consisting of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Pichia, Zygosaccharomyces, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

Termination control regions may also be derived from various genes native to the preferred hosts. Optionally, a termination site may be unnecessary; however, it is most preferred if included.

Additionally, the inserted genetic material may include a ribosome binding site. The ribosome binding site may be from a phage lambda CII gene or is selected from the group consisting of ribosome binding sites from a gene of *Comamonas, Corynebacterium, Brevibacterium, Rhodococcus, Azotobacter, Citrobacter, Enterobacter, Clostridium, Klebsiella, Salmonella, Lactobacillus, Aspergillus, Saccharomyces, Zygosaccharomyces, Pichia, Kluyveromyces, Candida, Hansenula, Dunaliella, Debaryomyces, Mucor, Torulopsis, Methylobacteria, Bacillus, Escherichia, Pseudomonas, Rhizobium*, and *Streptomyces*.

Optionally, the gene products may preferably be a secreted product of the transformed host. Secretion of desired proteins into the growth media simplifies purification procedures and reduces costs. Secretion signal sequences are often useful in facilitating the active transport of expressible proteins across cell membranes. A transformed host capable of secretion may be created by incorporating in the host a DNA sequence that codes for a secretion signal. Methods for choosing appropriate signal sequences are well known in the art (see for example EP 546049; WO 93/24631). The secretion signal DNA may be located between the expression-controlling DNA and the instant coding sequence or coding sequence fragment, and in reading frame with the latter.

Protein Engineering

The present mutant nitrilases were produced by mutagenesis. It is contemplated that the present nucleotides may be used to produce gene products having further enhanced or altered activity. Various methods are known for mutating a native gene sequence to produce a gene product with altered or enhanced activity including, but not limited to 1) random mutagenesis, 2) domain swapping (using zinc finger domains or restriction enzymes, 3) error-prone PCR (Melnikov et al., *Nucleic Acids Research*, 27(4):1056–1062 (1999)); 4) site directed mutagenesis (Coombs et al., *Proteins* (1998), pp 259–311,1 plate. Angeletti, Ruth Hogue, Ed., Academic: San Diego, Calif.); and 5) "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The polymerase chain reaction (PCR) can be used to amplify a DNA fragment with the concomitant creation of numerous mutations by mis-incorporation of nucleotides. This can be achieved by modifying the PCR conditions such as altering the ratios of dNTPs or adding various amounts of manganese chloride in the reaction (Fromant et al., *Anal Biochem*, 224(1):347–53 (1995); Lin-Goerke et al., *Biotechniques*, 23(3):409–12 (1997)). The pool of mutated DNA fragments can then be cloned to yield a library of mutated plasmids that can then be screened following expression in a host such as *E. coli*.

The method of gene shuffling is particularly attractive due to its facile implementation, high rate of mutagenesis, and ease of screening. The process of gene shuffling involves the restriction endonuclease cleavage of a gene of interest into fragments of specific size in the presence of additional populations of DNA regions having similarity and/or difference to the gene of interest. This pool of fragments will then be denatured and reannealed to create a mutated gene. The mutated gene is then screened for altered activity.

The present microbial sequences can be further mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonuclease well known in the art (Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989); hereinafter "Maniatis"). In addition to the present sequences, populations of fragments that are hybridizable to all or portions of the present sequences may be added. Similarly, a population of fragments, which are not hybridizable to the instant sequences, may also be added. Typically these additional fragment populations are added in about a 10- to about a 20-fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to about 75° C. Renaturation can be accelerated by the addition of polyethylene glycol ("PEG") or salt. A suitable salt concentration may range from 0 mM to about 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to about 50 times, more preferably the sequence is repeated from 10 to about 40 times. The resulting nucleic acid is a larger double-stranded polynucleotide ranging from about 50 bp to about 100 kB and may be screened for expression and altered activity by standard cloning and expression protocols (Maniatis, supra).

Furthermore, a hybrid protein can be assembled by fusion of functional domains using the gene shuffling (exon shuffling) method (Nixon et al., *PNAS*, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

Stabilizing Agents to Improve Nitrilase Stability and Productivity When Converting Glycolonitrile to Glycolic Acid Glycolonitrile can be synthesized by reacting formaldehyde with hydrogen cyanide (U.S. Pat. No. 2,175,805, U.S. Pat. No. 2,890,238, U.S. Pat. No. 5,187,301, and copending U.S. Provisional Patent Application 60/638127). Depending upon the purity of the reactants and the reaction conditions used to make glycolonitrile, a variety of impurities may exist in the final product. These impurities can interfere with the efficiency of converting glycolonitrile to glycolic acid. In one embodiment, the aqueous glycolonitrile solution can be treated to remove undesirable impurities prior to being enzymatically converted to glycolic acid.

Another method to increase the stability/productivity of an enzyme catalyst is the addition of one or more compounds that will react with undesirable compounds in the glycolonitrile solution that may interfere with the catalyst stability and/or productivity. The undesirable compounds include, but are not limited to formaldehyde, formaldehyde-derived impurities, formaldehyde-derived oligomers and polymers, glycolamide, glycolamide-derived impurities, hydrogen cyanide-derived impurities, hydrogen cyanide-derived oligomers and polymers, glycolonitrile-derived impurities, glycolonitrile-derived oligomers and polymers, glycolide, linear oligomers of glycolic acid, and possibly oxygen (reactions conducted under substantially oxygen free conditions improved catalyst stability). The undesirable compounds may also include those that 1) react with and inactivate the nitrilase catalyst, 2) compete with glycolonitrile in the reaction, 3) react with glycolonitrile or glycolic acid to form unwanted byproducts, or 4) adversely affect the recombinant host cell (i.e. promote cell lysis). Examples of suitable compounds that can be added to the glycolonitrile reaction mixture may include, but are not limited to thiosulfates (e.g. potassium thiosulfate, $K_2S_2O_3$), dithionites (e.g., sodium dithionite, $Na_2S_2O_4$), and cyanide compounds (e.g. HCN, NaCN, KCN, etc.). In one embodiment, the compound is added to the glycolonitrile reaction mixture before, during, or after the addition of the enzyme catalyst. In another embodiment, the compound is added to the reaction mixture so that the final concentration in the reaction mixture is at least about 0.001 M to less than about 5 wt % of the reaction mixture. In a further embodiment, the compound is added to the reaction mixture so that the final concentration is at least about 0.01 M. In yet a further embodiment, the compound is added to the reaction mixture so that the final concentration of compound is about 0.01 M to about 1 M.

In a further aspect of the invention, the present process is conducted under substantially oxygen free conditions. As used herein, the terms "oxygen free conditions", "oxygen free atmosphere" and "substantially oxygen free conditions" refers to a reaction condition where a non-reactive gas, such as nitrogen, is used to purge and/or blanket the reaction vessel so that molecular oxygen ($O_2$) is not present during present process. One of skill in the art recognizes that trace amounts of molecular oxygen may exist under substantially oxygen free conditions. In one aspect, the term "substantially oxygen free" means a reaction condition where the molecular oxygen concentration is less than about 5%, preferably less than 2%, more preferably less than 1%, and most preferably less than 0.1% of the gas in the reaction vessel. In another aspect, the present process is conducted under substantially oxygen free conditions where nitrogen ($N_2$) is used to blanket the aqueous reaction mixture in the reaction vessel.

Controlling the Concentration of Glycolonitrile to Improve Catalyst Stability and Productivity Another method to increase the nitrilase stability is controlling the maximum concentration of glycolonitrile in the aqueous reaction mixture. As described previously, glycolonitrile dissociates in polar solvents to release formaldehyde and hydrogen cyanide. Formaldehyde in the reaction mixture may react with the enzyme catalyst leading to premature inactivation and a decrease in catalyst productivity. Controlling the concentration of the glycolonitrile in solution can increase both the catalyst stability and productivity of the catalyst (grams of glycolic acid produced per gram of catalyst). As shown in Examples 12–15 (Table 9), a nitrilase catalyst derived from the *Acidovorax facilis* 72W rapidly loses its activity in reactions that contain 3 M glycolonitrile after only 3 recycle reactions. Decreasing the concentration to 1 M and/or the stepwise addition of 3 M glycolonitrile in 1 M increments (added after the previous additions of glycolonitrile have been converted to ammonium glycolate) increases the catalyst productivity significantly (Table 9). In one embodiment, a stepwise addition (aliquots) of glycolonitrile to the aqueous reaction mixture increases the productivity of the catalyst. In another embodiment, the glycolonitrile is added to the aqueous reaction mixture in a stepwise fashion so that the total concentration of glycolonitrile remains about 1 M or less during the reaction.

As shown in Example 15, a continuous addition of glycolonitrile also increases the catalyst productivity over several recycle reactions. In one embodiment, the method to produce ammonium glycolate from glycolonitrile uses a continuous addition of glycolonitrile. In another embodiment, the rate of glycolonitrile addition is at least 5-times the Km of the catalyst. The present catalysts typically have a Km for glycolonitrile of approximately 1 mM (wild type *A. facilis* 72W; SEQ ID NO: 6) to about 2.7 mM. As known in the art, a substrate concentration of approximately 5-times the Km value (i.e., 5×2.7 mM=13.5 mM) results in a reaction rate that is approximately 97% of the maximum reaction rate (Vmax). In yet another embodiment, the glycolonitrile feed rate is controlled to maintain a glycolonitrile concentration in the reaction mixture of about 5 mM to about 1 M, preferably about 100 mM to about 1 M, more preferably about 100 mM to about 500 mM.

Control of pH

Reactions using the nitrilase catalysts of the present invention are typically run at a pH ranging from about 5 to about 10, preferably between 5.5 and about 8, more preferably about 5.5 to about 7.7, and most preferably about 6 to about 7.7.

Analysis of Glycolic Acid and Glycolonitrile

Analytical methods suitable for analyzing the production of glycolic acid are well-known in the art including, but not limited to HPLC, CE, GC, and MS. For example, HPLC analysis was used to determine the amount of glycolic acid production using a refractive index detector and a Bio-Rad HPX-87H column (30 cm×7.8 mm dia.) and 0.01 N sulfuric acid at 1.0 mL/min (isocratic) as a mobile phase at 50° C. The HPLC method was suitable for quantification of both the substrate (glycolonitrile) and product (glycolic acid).

Industrial Production of the Microbial Catalyst

Where commercial production of the present nitrilases using the present mutated nitrilase genes is desired, a variety of culture methodologies may be used. Fermentation runs may be conducted in batch, fed-batch, or continuous mode, methods well-known in the art (Thomas D. Brock in *Biotechnology: A Textbook of Industrial Microbiology*, Second Edition (1989) Sinauer Associates, Inc., Sunderland, Mass., (1989); Deshpande, Mukund V., *Appl. Biochem. Biotechnol.* 36(3): 227–234 (1992)).

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock (supra) and Deshpande (supra).

Commercial production of the present nitrilase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end cell concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady-state growth conditions and thus the cell loss due to media being drawn off must be balanced against the cell growth rate in the culture. Methods of modulating nutrients and growth factors for continuous culture processes, as well as techniques for maximizing the rate of cell formation, are well known in the art of industrial microbiology and a variety of methods are detailed by Brock (supra).

Fermentation media in the present invention must contain suitable carbon substrates. Suitable substrates may include, but are not limited to monosaccharides such as glucose and fructose, disaccharides such as lactose or sucrose, polysaccharides such as starch or cellulose or mixtures thereof, and unpurified mixtures from renewable feedstocks such as cheese whey permeate, cornsteep liquor, sugar beet molasses, and barley malt. Hence, it is contemplated that the source of carbon utilized in the present invention may encompass a wide variety of carbon-containing substrates and will only be limited by the choice of organism.

Methods to Recover Glycolic Acid from Ammonium Glycolate

Methods to recover and/or obtain an organic acid from the corresponding ammonium salt are known in the art. Methods to recover and/or obtain glycolic acid from an aqueous solution comprising ammonium glycolate may include, but are not limited to, ion exchange (anionic and/or cationic), electrodialysis, reactive solvent extraction, thermal decomposition, alcoholysis (esterification followed by hydrolysis of the glycolic acid ester into glycolic acid), and combinations thereof.

Ion Exchange (Cationic)

Cationic ion exchange is a reversible process is which a dissolved ionic species is taken up by a solid in a stoichiometric manner. Cationic ion exchange is well known in the art. In the present process, ammonium glycolate is fed to the cationic ion exchange resin where the ammonium ion is exchanged with a proton, forming glycolic acid (see Example 28). The glycolic acid passes through the column and is collected.

Once the resin is saturated with ammonium ion, regeneration with an acid, for example sulfuric acid, will produce the byproduct, ammonium sulfate salt. The cationic exchange can be performed in batches, using a simulated moving bed or carrousel (see *Perry's Chemical Engineers' Handbook*, 7$^{th}$ ed., Perry, Robert H., Green, Dow W., and Maloney, James O., editors; McGraw Hill Companies, Inc., New York, N.Y., 1997; hereinafter "Perry's"). Selection of the resin may impact feed concentration, which may range from about 0.02 wt % salt to about 50 wt % ammonium glycolate, preferably about 0.02 wt % to about 40 wt %. The regeneration acid used typically ranges from about 0.5 wt % to about 20 wt %.

Ion Exchange (Anionic)

Anionic ion exchange is also well known in the art. Anionic exchange is similar to cationic exchange except that a weak anionic resin is used (see Perry's, supra). Once again, selection of the resin may impact feed concentration, which may range from about 0.02 wt % to about 90 wt % ammonium glycolate, preferably about 0.02 wt % to about 40 wt %. Regeneration of the resin would typically use a weak acid.

Solvent Extraction (Reactive)

One method that has been used to isolate carboxylic acids is reactive extraction. This method has been reported to be useful for extracting lactic acid from ammonium lactate (Wasewar et al., *J. Biotechnol.*, 97:59–68 (2002)). Reactive extraction involves the use of a reactive organic solvent (i.e., an amine) to complex with the acid in the aqueous phase. The first step in the process typically involves acidification of the aqueous solution containing the salt of the desired acid. The acidified aqueous solution is then contacted with an organic solvent typically comprised of a reactive tertiary amine and one or more diluents. The reactive amine (typically a tertiary C8–C10 trialkylamine such as Alamine® 336, Cognis Corp, Cincinnati, Ohio) reacts with the carboxylic acid forming an acid/amine complex that is preferentially soluble in the organic phase (Tamada et al., *Ind. Eng. Chem. Res.* 29:1319–1326 (1990); Tamada et al., *Ind. Eng. Chem. Res.* 29:1327–1333 (1990)). The use of a tertiary alkylamine typically provides much higher distribution coefficients than would be obtainable with normal solvent extraction. Back extraction is then used to recover the acid from the organic phase.

Inci, I. (*Chem. Biochem. Eng. Q.*, 16(2):81–85 (2002); Inci, I. and Uslu, H., *J. Chem. Eng. Data*, 50:536–540 (2005)) report the use of reactive amine solvents for the extraction of glycolic acid. However, these experiments reported the extraction coefficients of pure glycolic acid dissolved in pure water. Inci does not illustrate or teach a process to obtain glycolic acid from a complex aqueous matrix (e.g., aqueous solutions of glycolic acid comprising significant amounts of mineral salts and other impurities), such as concentrated aqueous solutions of ammonium glycolate.

Reactive solvent extraction may also be used to obtain glycolic acid from an aqueous solution of ammonium glycolate (see Co-pending U.S. provisional patent application 60/638128; herein incorporated by reference). More specifically, a method to isolate glycolic acid from an aqueous solution comprising ammonium glycolate is provided comprising:

a) providing a first phase, wherein said first phase is a water-immiscible organic solvent mixture comprising:
  i) about 30 volume percent to about 99 volume percent of said first phase is at least one tertiary alkyl amine having the formula

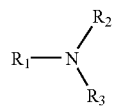

wherein $R_1$, $R_2$, and $R_3$ are independently a C8 to C12 alkyl group; and
  ii) about 1 volume percent to about 70 volume percent of said first phase is at least one diluent selected from the group consisting of methyl isobutyl ketone, 1-octanol, 1-decanol, methylene chloride, 1-chlorobutane, chlorobenzene, chloroform, kerosene, toluene, mixed xylenes, tributyl phosphate, and mixtures thereof;

b) providing a second phase, wherein said second phase is an aqueous solution comprising glycolic acid having a pH of about 3 or less; said second phase formed by the process of:
  i) providing an aqueous solution of ammonium glycolate; said aqueous solution of ammonium glycolate having a concentration about 5 weight % to about 40 weight % ammonium glycolate; and
  ii) adding an amount of mineral acid sufficient to lower the pH of the aqueous ammonium glycolate solution of (b)(i) to about 3 or less;
  whereby an aqueous solution comprising glycolic acid is formed;

c) contacting said first phase with said second phase in a reactive extraction process; thereby forming a glycolic acid-loaded first phase;

d) isolating said glycolic acid-loaded first phase;

e) contacting said glycolic acid-loaded first phase with a third phase in a back extraction process; whereby glycolic acid in the glycolic acid-loaded first phase is extracted into said third phase; wherein said third phase is an aqueous solution that is immiscible in said glycolic acid-loaded first phase; and f) recovering the glycolic acid from said third phase.

In one embodiment, the tertiary trialkylamine is selected from the group consisting of tri-n-octylamine, tri-isooctylamine, tri-n-nonylamine, tri-n-decylamine, and tri-n-dodecylamine. In another embodiment, the tertiary trialkylamine is selected from the group consisting of Alamine® 308 (CAS# 2757-28-0), Alamine® 300 (CAS# 1116-76-3), Alamine® 304-1 (CAS# 102-87-4), and Alamine® 336 (CAS# 68814-95-9) (Cognis Corp., Cincinnati, Ohio). In a further embodiment, the diluent is selected from the group consisting of methyl isobutyl ketone (MIBK), kerosene, toluene, mixed xylenes, 1-octanol, and mixtures thereof. In yet another embodiment, the water-immiscible organic solvent is selected from the group consisting of 90% (vol/vol) Alamine® 336:10% (vol/vol) MIBK; 90% Alamine® 336:10% 1-octanol; 90% Alamine® 336:10% toluene; and 90% Alamine® 336:10% mixed xylenes.

The concentration of tertiary trialkyl amine in the first phase may range from about 30 percent (vol/vol) to about 99 percent (vol/vol), preferably about 50 percent (vol/vol) to about 90 percent (vol/vol), and most preferably about 70 percent (vol/vol) to about 90 percent (vol/vol). The amount of diluent in the first phase may range from about 1 percent (vol/vol) to about 70 percent (vol/vol), preferably about 10 percent to about 50 percent, and most preferably about 10 to about 30 percent A suitable organic extraction mixture for extracting glycolic acid is comprised of a mixture of Alamine® 336 with one or more diluents selected from the group consisting of methyl isobutyl ketone (MIBK), 1-octanol, 1-decanol, methylene chloride, 1-chlorobutane, chlorobenzene, chloroform, kerosene, toluene, mixed xylenes, and tributyl phosphate. In one embodiment, the organic phase extractant is comprised of Alamine 336 in combination with one or more diluents selected from the group consisting of MIBK, 1-octanol, toluene, xylene, and kerosene. In another embodiment, the reactive organic solvent is comprised of about 50% to about 95% Alamine® 336, preferably about 65% to about 95% of the organic solvent mixture. The organic solvent is comprised of one or more diluents in a range of about 50% to about 5% diluent, preferably 35% to about 5% of the organic solvent mixture. In one embodiment, the mixed organic solvent is comprised of about 70% Alamine® 336, about 10% MIBK, and about 20% kerosene. In another embodiment, the mixed organic solvent is comprised of about 90% Alamine® 336 and about 10% diluent selected from the group consisting of MIBK, 1-octanol, toluene, and xylene.

One of skill in the art can determine the preferred temperature of the organic phase extraction. In one embodiment, the extraction reaction is conducted at a temperature from about 10° C. to about 90° C., more preferably about 20° C. to about 75° C., and most preferably about 25° C. to about 75° C.

The amount of mixed organic solvent required to extract the glycolic acid from the acidified aqueous phase is dependent upon the degree of solvent loading. One of skill in the art can adjust the volume of the mixed organic solvent used to extract the glycolic acid depending upon the amount of glycolic acid present in the aqueous phase. The glycolic acid can be recovered from the organic phase by back extraction.

Another method to obtain glycolic acid from ammonium glycolate is thermal decomposition in the presence of an esterifying agent. The solvent may act by protecting the glycolic acid from reactive ammonia (thereby preventing amide formation) or may act as an organic reactive extraction solvent, thereby aiding in the separation of the acid (Meng et al., US 2004/0210087; hereby incorporated by reference in its entirety). Optionally, this method can also include an alcohol, thereby creating the ester (which may be more soluble in the organic solvent). The organic solvent may be selected from the group consisting of tertiary alkylamines, alcohols, amides, ethers, ketones, phosphorus esters, phosphine oxides, phosphine sulfides, alkyl sulfides, and combinations thereof. Glycolic acid (or the corresponding ester) is then recovered from the organic solvent (liquid phase) during a back extraction step. The recovered solvent can be recycled to the salt splitting reaction step. Unfortunately, solvent extraction/back extraction may be problematic as various immiscible fluids form complex physical mixtures that are difficult to separate.

Alcoholysis (Esterification)

The ammonium glycolate can be reacted with an alcohol to form the corresponding glycolic acid ester. The glycolic acid ester can be converted into glycolic acid and the corresponding alcohol by hydrolysis of the ester bond. The hydrolysis can be accomplished chemically or enzymatically (i.e., use of an esterase, protease, etc.). Method to hydrolyze carboxylic acid esters are well-known in the art (see Gurthrie, J. and Cullimore, P., *Can J. Chem.*, 58(13): 1281–1294 and US2004/0138409 A1, herein incorporated by reference).

For example, Cockrem (U.S. Pat. No. 6,291,708 B1) teaches rapid heating of a mixture of ammonium salt of an organic acid with alcohol to produce a liquid stream containing acid, ester, and unreacted ammonium salt. The organic acid and/or ester may be subsequently isolated from the liquid product stream.

Alternatively, copending U.S. provisional patent application 60/638126 provides a process to obtain glycolic acid from an aqueous solution comprising ammonium glycolate comprising:

(a) providing
  (i) an aqueous solution comprising ammonium glycolate; and
  (ii) a heated alcohol vapor feed stream comprising an alcohol having the formula:

$R_2$—OH wherein $R_2$ is a C1 to C4 straight chain or branched alkyl group; and
  (iii) a reaction vessel;
(b) contacting said aqueous solution comprising ammonium glycolate with said heated alcohol vapor feed stream in said reaction vessel whereby a first vapor product stream is produced comprising a glycolic acid ester; and
(c) recovering the glycolic acid ester from said first vapor product stream.

The glycolic acid ester can be converted into glycolic acid and the corresponding alcohol by hydrolysis of the ester bond. The hydrolysis can be accomplished chemically or enzymatically (i.e., use of an esterase, protease, etc.). Method to hydrolyze carboxylic acid esters are well-known in the art (see Gurthrie, J. and Cullimore, P., *Can J. Chem.*, 58(13):1281–1294 and US2004/0138409 A1, herein incorporated by reference).

In one embodiment, the alcohol is selected from the group consisting of methanol, ethanol, n-propanol, isopropanol, n-butanol, isobutyl alcohol, and t-butanol. In a preferred embodiment, the alcohol is methanol.

The amount of heated alcohol vapor contacted with the carboxylic acid ammonium salt is typically in a molar excess relative to the amount of carboxylic acid ammonium salt in the aqueous feed stream. The molar ratio of the heated alcohol vapor to the carboxylic acid ammonium salt may vary, but it typically from about 5 to about 300 moles per mole of carboxylic acid ammonium salt (molar ration at least about 5:1 to about 300:1), preferably about 5 to about 200 moles per mole of the carboxylic acid ammonium salt, most preferably about 20 to about 100 moles per mole of carboxylic acid ammonium salt. A molar excess of the alcohol vapor tends to inhibit amide formation.

The alcohol vapor feed stream (e.g., methanol) temperature is typically chosen to ensure that the alcohol generally remains in its vapor phase so that it acts as both an esterifying agent and a stripping/carrying gas. The temperature of the heated alcohol vapor feed stream entering the reaction chamber may vary according to the selected alcohol as well as the specific equipment geometry. The heated alcohol vapor fed acts as a source of heat for the reaction, an esterifying agent, and as a stripping/carrying gas for the carboxylic acid ester formed by the present process.

The present examples illustrate the use a heated methanol vapor to form methyl glycolate (which is subsequently hydrolyzed to glycolic acid). Typically, the temperature of the heated methanol vapor is about 140° to about 350° C. In one embodiment, the temperature of the methanol vapor feed stream is about 170° C. to about 300° C. In another embodiment, the temperature of the methanol vapor feed stream is about 230° C. to about 250° C.

A typical operating temperature for the alcoholysis reactor is about 140° C. to about 300° C., preferably about 170° C. to about 200° C. In one aspect, the carboxylic acid ammonium salt is ammonium glycolate and the alcohol is methanol. The reactor temperature used in this particular combination is typically about 100° C. to about 300° C., preferably about 150° C. to about 250° C., more preferably about 170° C. to about 225° C., and most preferably about 170° C. to about 200° C.

The reactor may optionally include a packing material or a high boiling point fluid/liquid to improve the yield of the desired carboxylic acid ester. The benefit of the packing or high boiling point fluid is to improve the contacting between the aqueous salt solution and the alcohol vapor. The packing may be random packing, engineered packing, or various distillation plate designs. See Perry's $7^{th}$ edition Chapter 14.23 through 14.61 (*Perry's Chemical Engineers' Handbook*, $7^{th}$ ed., Perry, Robert H., Green, Dow W., and Maloney, James O., editors; McGraw Hill Companies, Inc., New York, N.Y., 1997). Commercial designs for gas liquid reaction systems are illustrated in Perry's FIGS. 23–25, 23–26, and 13.79. The high boiling point fluid should be selected to have a low vapor pressure at the chosen operating conditions or be easily separated from the recovered ester. The fluid may be inert to the esterification chemistry (such as mineral oil) or potentially participate in the esterification chemistry such as a polyalkylene glycol (polyol). The polyol is a material with a molecular weight greater than 150 and at least one hydroxyl group, such as. Typical polyols include polyethylene ether glycol (PEG), polypropylene glycol (PPG) and polytetramethylene ether glycol (PTMEG), as well as copolymers of these polyalkylene ether glycols.

Electrodialysis

Electrodialysis with bipolar membrane (EDBM) has been proposed to recovering organic acids from their corresponding ammonium salt. For EDBM to work, the solutions must be conductive. For the ammonium salt of weak acids, the products of EDBM (organic acid and ammonium hydroxide) are very weak conductors resulting in high resistance of the solutions and low production rates. To offset this, a conductive salt (i.e., ammonium chloride) is added to the base loop (ammonium hydroxide stream). As the base concentration increases, ammonia can be stripped from the solution and the ammonium salt recycled to maintain conductivity.

The composition of the ammonium salt of the organic acid must be carefully monitored for multivalent cations such as calcium. These cations may precipitate by associating with hydroxyl groups and destroy the membranes. Concentrations of the multivalent cations are preferably below about 5 ppm, most preferably below about 1 ppm.

For example, a typical lab scale EDBM system can be set up with membranes suitable for ammonium salts. First, a recirculating base loop containing about 5 wt % ammonium chloride is established. An approximately 3 M ammonium glycolate recirculation loop is also established. A typical batch test run is conducted at constant current of about 0.5 to about 1.0 $kA/m^2$. The circulation loops are maintained for about 1 hour to about 5 hours. As the EDBM proceeds, conductivity and pH in the ammonium glycolate loop decreases. Typically, an EDBM run under such conditions would be expected to convert at least about 80% of the ammonium glycolate into glycolic acid. The resulting glycolic acid/ammonium glycolate solution can be subsequently treated with a strong cationic ion exchange resin or other methods to complete the conversion.

Polymerization

The ammonium salt of a carboxylic acid comprised of a hydroxyl group can undergo condensation polymerization to form dimers, oligomers, and polymers while liberating ammonia. The resulting polymers can be separated from the reaction mixture using any number of well-known techniques. Once separated from the reaction mixture, depolymerization can be used to obtain the free acid.

Thermal Salt Cracking

Thermal decomposition ("salt cracking") may be used to obtain a product comprising glycolic acid (see co-pending U.S. Provisional Patent Application 60/638148; herein incorporated by reference in its entirety). This process does not require the addition of one or more chemicals prior to thermally decomposing the substantially anhydrous ammonium glycolate salt. Thermal salt cracking may be combined with one or more of the present recovery methods to further isolate glycolic acid.

The first step in the process is the removal of free water from a feed stream comprising an aqueous solution of ammonium glycolate, so that a substantially anhydrous ammonium glycolate salt is formed (the substantially anhydrous salt is a viscous liquid at room temperature (~25° C.)). Methods of removing the free water from the aqueous reaction mixture are well-known in the art including, but not limited to distillation, vacuum distillation, lyophilization, and evaporation The next step in the process involves heating the substantially anhydrous salt under a vacuum to a temperature sufficient to thermally decompose the ammonium salt into glycolic acid and ammonia. The temperature used should be chosen so that thermal decomposition of the salt occurs while minimizing decomposition of the acid and/or minimizing unwanted side reactions that may generate undesirable byproducts such as glycolamide. The substantially anhydrous ammonium glycolate salt is typically heated at a temperature of about 100° C. to no more than about 140° C. under a vacuum (0.5 to about 385 mm Hg absolute pressure) for a period time sufficient thermally decompose the salt into a product comprising glycolic acid. A vacuum is used to aid in the removal of ammonia. Suitable vacuum pressures can be determined by one of skill in the art. An example of a typical vacuum range is about 0.5 to about 385 mm Hg absolute pressure. The thermal decomposition of the ammonium salt can use any evaporator design, however a wipe film evaporator is preferred.

Thermally decomposing the salt under the specified conditions converts a significant portion of the molten ammonium glycolate salt into glycolic acid and some additional byproducts such as glycolide (cyclic dimer of glycolic acid), linear polymeric forms of glycolic acid (typically dimers up to pentamers), the ammonium salts of linear polymeric forms of glycolic acid (typically dimers up to pentamers), and glycolamide. One of skill in the art can adjust the conditions used to thermally decompose the ammonium glycolate to optimize free glycolic acid production while minimizing undesirable side reactions, such as the production of glycolamide. The ammonia produced during thermal decomposition can be recovered and recycled. Optionally, the aqueous ammonium glycolate solution is partially deammoniated to produce a deammoniated product that contains significantly less ammonium ion. This deammoniated product is particularly attractive for subsequent processing as less waste (mineral salts) is generated.

In addition to recovery of glycolic acid from a solution comprising ammonium glycolate, the solution comprising ammonium glycolate may be recovered directly by separation from the nitrilase catalyst by known techniques including but not limited to decantation or filtration, and subsequently optionally concentrated by distillation of water from the filtrate.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

GENERAL METHODS

Materials and methods suitable for the maintenance and growth of bacterial cultures are well known in the art. Techniques suitable for use in the following examples may be found as set out in *Manual of Methods for General Bacteriology* (1994) (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C.) or by Thomas D. Brock, in *Biotechnology: A Textbook of Industrial Microbiology*, (1989) Second Edition, (Sinauer Associates, Inc., Sunderland, Mass.).

Procedures required for genomic DNA preparation, PCR amplification, DNA modifications by endo- and exo-nucleases for generating desired ends for cloning of DNA, ligations, and bacterial transformation are well known in the art. Standard recombinant DNA and molecular cloning techniques used here are well known in the art and are described by Maniatis, supra; and by T. J. Silhavy, M. L. Bennan, and L. W. Enquist, *Experiments with Gene Fusions*, (1984) Cold Spring Harbor Laboratory Press, Cold Spring, N.Y.; and by Ausubel, F. M. et al., *Current Protocols in Molecular Biology*, (1994–1998) John Wiley & Sons, Inc., New York.

The abbreviations in the specification correspond to units of measure, techniques, properties, or compounds as follows: "sec" or "s" means second(s), "min" means minute(s), "h" or "hr" means hour(s), "d" means day(s), "µM" means micromolar, "mM" means millimolar, "M" means molar, "µmol" means micromoles, "mmol" means millimole(s), "wt" means weight, "wt %" means weight percent, "g" means grams, "µg" means micrograms, "L" means liters, "mL" means milliliters, "µL" means microliters, "kb" means kilobase(s), "kDa" means kilodalton, "HPLC" means high performance liquid chromatography, "OD" means optical density at the designated wavelength, "nm" means nanometers, "rpm" means revolutions per minute, "SDS-PAGE" means sodium dodecyl sulfate polyacrylamide gel electrophoresis, "dcw" means dry cell weight, "U" means units of nitrilase activity, "GLA" means glycolic acid or the corresponding ammonium salt, "NH$_4$GLA" means ammonium glycolate, "GLN" mean glycolonitrile, "Rxn" means reaction, "mM GLA/h" is the initial reaction rate measured in mM GLA per hour, "ca." means approximately, "HCN" means hydrogen cyanide, and "HCHO" means formaldehyde.

EXAMPLE 1

Construction of High Copy Nitrilase Expression Plasmid

Synthetic Oligonucleotide Primers

```
165
(5'-CGACTGCAGTAAGGAGGAATAGGACATGGTTTCGTATAACAGC
AAGTTC-3'; SEQ ID NO:1)
and 166
(5'-TGATCTAGAGCTTGGAGAATAAAGGGGAAGACCAGAGATG-
3'; SEQ ID NO:2)
```

(which incorporate PstI and XbaI restriction sites (underlined), respectively) were used to PCR amplify the nitrilase gene from *A. facilis* 72W (ATCC 55746) genomic DNA (SEQ ID NO:5).

Typical PCR parameters are as follows:

Step 1: 5 minutes at 95° C.

Step 2: 0.5 minute at 95° C. (denaturation)

Step 3: 0.5 minute at 55° C. (annealing)

Step 4: 1 minute at 74° C. (extension)

Steps 2–4 are repeated 25 cycles

PCR reagents are supplied by and used as recommended by Roche Diagnostics Corporation (Indianapolis, Ind.).

The only change from native *Acidovorax facilis* 72W sequence is a change to the first nucleotide from G to A to facilitate expression in *E. coli*. In so doing, the start codon of the nitrilase gene was changed from the native GTG to ATG. Accordingly, the first amino acid of the corresponding nitrilase protein is changed from the native valine to methionine (SEQ ID NO: 6). Oligonucleotide primer 165 also introduces a ribosome binding site (bold) and a codon (TAG) to stop translation of lacZ prior to initiation of translation of nitrilase. The PCR product was digested with PstI and XbaI, and cloned into pUC19 (GenBank® L09137; New England Biolabs, Beverly, Mass.) digested with PstI and XbaI, to generate the plasmid identified as pSW138.

EXAMPLE 2

Expression of Active Nitrilase in *E. coli*

Plasmid pSW138 was used to transform *E. coli* MG1655 (ATCC 47076) and *E. coli* FM5 (ATCC 53911) to generate the two strains identified as (1) MG1655/pSW138 and (2) FM5/pSW138, respectively. Each strain was grown, induced, harvested, and assayed for nitrilase activity (conversion of glycolonitrile to glycolic acid) as described below. Replicates of six are performed for each strain.

1. Bacterial Growth

Strain inoculums were grown in LB media supplemented with ampicillin (50 mg/L), at 37° C. with shaking (200 rpm) for 16–18 hours.

2. Induction of Nitrilase Expression

Sufficient inoculum was added to fresh LB media supplemented with ampicillin (50 mg/L) and IPTG (1 mM) to give an initial OD (600 nm) of approximately 0.1. Cultures were incubated at 37° C. with shaking (200 rpm) for approximately 6–8 hours.

3. Bacterial Harvest

Bacterial cells were harvested by centrifugation, removing as much liquid as possible, and cell pellets were frozen at −70° C.

4. Assay for Nitrilase Activity

Into a temperature controlled (25° C.) 20-mL glass scintillation vial equipped with a micro stir bar was added 3.0 mL of substrate solution (0.667 M glycolonitrile; TCI) and 1.0 mL of cell suspension (400 mg wet cell weight/mL in 100 mM sodium pyrophosphate pH 6.0, 1 µg/mL DNAse). Final glycolonitrile concentration was 500 mM and final cell concentration was 100 mg/mL. Samples (100 µL) were removed at 5, 10, 15, 30, 45 and 60 min and added to assay mix (100 µL deionized water, 3 µL 6.0 N HCl, 200 µL 200 mM n-propanol), followed by vortexing and centrifugation. Resulting supernatants were analyzed by HPLC (HPX 87H column, 30 cm×7.8 mm; 0.01 N $H_2SO_4$ mobile phase; 1.0 mL/min flow at 50° C.; 10-µL injection volume; 20 min analysis time) for glycolonitrile (GLN) and glycolic acid (GLA). Dry cell weights (dcw) were determined on duplicate samples by microwave drying. Nitrilase activity was reported as U/g dcw, where 1 unit (U) converts 1 µmol of GLN to GLA in 1 min at 25° C. (Table 1).

TABLE 1

| Strain | Nitrilase activity (U/g dcw) |
|---|---|
| MG1655/pSW138 | 22.1 |
| FM5/pSW138 | 3.3 |

EXAMPLE 3

Construction of A. facilis 72W Nitrilase Random Mutagenesis Libraries by Error-Prone Polymerase Chain Reaction Genomic DNA was prepared from A. facilis 72W (ATCC 55746) using a Puregene® DNA isolation kit according to the manufacturer's instructions (Gentra Systems, Minneapolis, Minn.). Error-prone PCR was performed on the A. facilis 72W nitrilase gene (coding sequence; SEQ ID NO:5) using primers identified as SEQ ID NO: 3 (5'-GCGCATATG GTTTCGTATAACAGCAAGTTCC-3') and SEQ ID NO: 4 (5'-ATAGGATCCTTATGGCTACTTTGCTGGGACCG-3') according to instructions supplied with the GeneMorph® PCR Mutagenesis Kit (Stratagene, La Jolla, Calif.). Reaction conditions recommended to produce a low mutation frequency (0–3 mutations/kb) and a medium mutation frequency (3–7 mutations/kb) were employed. Ten percent of the 1.1 kb PCR product was ligated into the expression vector pTrcHis2 TOPO® according to instructions supplied with the pTrcHis2 TOPO® TA Expression kit (Invitrogen, Carlsbad, Calif.). One half of the ligation mixture was transformed into E. coli TOP10 according to supplier's recommendations (Invitrogen). One percent of the transformation mixture was plated onto LB plates supplemented with 50 mg/L ampicillin. Resultant transformants numbered 200–400 colonies, suggesting that the total PCR product produced was capable of generating 400,000–800,000 colonies, more than enough required to screen for improved enzyme activity. Mutation frequencies were confirmed by nucleotide sequence analysis of a randomly selected sample of clones. Sequence analysis also confirmed that approximately 50% of inserts were in the forward orientation, as expected. SDS-PAGE analysis confirmed that essentially all clones with forward orientation inserts expressed the ~41 kDa nitrilase protein when grown and induced as recommended (Invitrogen).

In addition, the native A. facilis 72W nitrilase gene was amplified by standard PCR using primers identified as SEQ ID NO: 3 and SEQ ID NO: 4, and the resulting DNA product was cloned into pTrcHis2-TOPO® (Invitrogen) according to manufacturer recommendations, to generate the plasmid pNM18. Transformation of E. coli TOP10 or E. coli FM5 (ATCC 53911) with pNM18 produced strains useful as respective controls. The A. facilis 72W nitrilase "control" sequence in pNM18 (SEQ ID NO: 5) is identical to the coding sequence of the wild-type A. facilis 72W except for a change in the start codon from GTG to ATG, facilitating expression in E. coli.

EXAMPLE 4

Screening A. facilis 72W Nitrilase Random Mutagenesis Libraries for Increased Nitrilase Activity Approximately 10,000 colonies from the low mutation frequency error-prone PCR library (constructed as described in Example 3) were plated on LB agar supplemented with 50 mg/L ampicillin. High throughput screening was performed in 96-well microtiter plates using robotics. After growth of individual colonies in liquid LB supplemented with 50 mg/L ampicillin and 1 mM IPTG (isopropyl-β-D-thiogalactopyranoside) for 18 h at 37° C., 200 rpm shaking, cultures were supplied with 50 mM glycolonitrile (GLN) for 1 h at 37° C., 80 Hz linear shaking. Reactions were stopped by filtering out the bacterial cells, and supernatants to be analyzed were sealed in microtiter plates and stored at 4° C. until analysis.

Production of glycolic acid (GLA) was measured by atmospheric pressure chemical ionization (APCI) mass spectrometry in the negative ion mode monitoring the M−H ion, m/z 75, in single ion mode. The mass spectrometer used was a Micromass (Waters) Quattro Ultima triple quad, with the following settings: source temperature=150° C., probe temperature=300° C., cone gas=80 L/hr, Desolvation gas=700–800 L/hr. Cone voltage=35 V, Corona voltage=20 mA. Multiplier=600 V, Dwell=0.1 s, Interchannel Delay=0.02 s. The mobile phase was 50/50 MeOH/$H_2O$ at 3.5 mL/min per needle with a 1:5 split of eluent before introduction into the mass spectrometer using a LC Packings Acurate splitter. Samples were delivered by a Gilson 215 auto-sampler with a 889 serial injection 8-valve bank injecting 30 mL of sample into 5-mL sample loops. A Hudson Plate Crane XT plate handling robot delivered plates to the deck of the Gilson auto-sampler. A needle and injection port wash with the same solvent at 5 mL/min was performed between each set of 8 injections. By this method, seven strains with increased nitrilase activity were identified and isolated.

EXAMPLE 5

Identification of Mutations in *A. facilis* 72W Nitrilase Conferring Increased Nitrilase Activity Nucleotide sequence analysis was used to identify any mutations present in the nitrilase gene of the seven TOP10 mutant strains isolated as described in Example 4, and the corresponding amino acid changes were deduced. All 7 strains showed the identical nitrilase sequence (SEQ ID NO: 8), with a single amino acid change, Leu at position 201 changed to Gln (L201Q) in the plasmid identified as pNM18-201Q. This change had no detectable effect on nitrilase protein production (compared to the native enzyme), as measured by SDS-PAGE analysis.

EXAMPLE 6

Saturation Mutagenesis of Nitrilase at Amino Acid Residue Position 201

A saturation mutagenesis library at amino acid position 201 of the *A. facilis* 72W nitrilase enzyme was constructed using degenerate oligonucleotides and the QuikChange® Site-Directed Mutagenesis Kit (Stratagene, La Jolla, Calif.) according to the manufacturer's instructions. Approximately 500 members of this library were screened for increased nitrilase activity as previously described (Example 4). Nucleotide sequencing analysis was used to determine any amino acid changes at position 201 that conferred increased nitrilase activity. In addition to L201Q (SEQ ID NO: 8), the following mutations conferring increased nitrilase activity were identified from the screen: L201G (SEQ ID NO: 16), L201H (SEQ ID NO: 18), L201K (SEQ ID NO: 20), L201N (SEQ ID NO: 22), L201S (SEQ ID NO: 24), L201A (SEQ ID NO:10), L201C (SEQ ID NO: 12), and L201T (SEQ ID NO: 14) in the plasmids identified as pNM18-201G, pNM18-201H, pNM18-201K, pNM18-201N, pNM18-201S, pNM18-201A, pNM18-201C, and pNM18-201T, respectively.

EXAMPLE 7

Targeted Saturation Mutagenesis of the *A. facilis* 72W Nitrilase Catalytic Domain We hypothesized that the catalytic domain within the *A. facilis* 72W nitrilase (SEQ ID NO: 6) may be a suitable region to mutate in an attempt to increase nitrilase activity toward 2-hydroxynitriles, namely glycolic acid.

Saturation mutagenesis within the *A. facilis* 72W nitrilase (SEQ ID NO: 6) catalytic domain (160G 161G̲ 162L 163N̲ 164C 165W̲ 166E 167H̲ 168F̲ 169Q 170P̲ 171L 172S̲ 173K̲) of those residues not universally conserved among known bacterial nitrilases (underlined) was completed using degenerate oligonucleotides and the QuikChange® Site-Directed Mutagenesis Kit (Stratagene, La Jolla, Calif.) according to the manufacturer's instructions. Specifically, nine mini-libraries (500–1000 colonies) were constructed, one for each of the active site residues targeted (underlined above). These libraries were screened for increased nitrilase activity as previously described. Nucleotide sequencing analysis was used to determine any amino acid changes that conferred increased nitrilase activity. The following changes conferring increased nitrilase activity were identified: F168K (SEQ ID NO: 26), F168M (SEQ ID NO: 28), F168T (SEQ ID NO: 30), and F168V (SEQ ID NO: 32) in the plasmids identified as pNM18-168K, pNM18-168M, pNM18-168T, and pNM18-168V, respectively.

EXAMPLE 8

Construction of MG1655/pSW138-168K, MG1655/pSW138-168M, MG1655/pSW138-168T, MG1655/pSW138-168V, MG1655/pSW138-201Q, MG1655/pSW138-201G, MG1655/pSW138-201H. MG1655/pSW138-201K, MG1655/pSW138-201N, and MG1655/pSW138-201S Each of the plasmids pNM18-168K, pNM18-168M, pNM18-168T, pNM18-168V, pNM18-201Q, pNM18-201G, pNM18-201H, pNM18-201K, pNM18-201N, and pNM18-201S was cleaved with EcoRI and the smaller EcoRI fragment (907 bp) was subcloned into the plasmid pSW138 (described in Example 1) which had also been cleaved with EcoRI, to generate the plasmids pSW138-168K, pSW138-168M, pSW138-168T, pSW138-168V, pSW138-201 Q, pSW138-201 G, pSW138-201 H, pSW138-201K, pSW138-201N, and pSW138-201S, respectively. Each of the plasmids pSW138-168K, pSW138-168M, pSW138-168T, pSW138-168V, pSW138-201Q, pSW138-201G, pSW138-201H, pSW138-201K, pSW138-201N, and pSW138-201S was used to transform *E. coli* MG1655 to generate the strains MG1655/pSW138-168K, MG1655/pSW138-168M, MG1655/pSW138-168T, MG1655/pSW138-168V, MG1655/pSW138-201Q, MG1655/pSW138-201G, MG1655/pSW138-201H, MG1655/pSW138-201K, MG1655/pSW138-201N, and MG1655/pSW138-201S; respectively.

EXAMPLE 9

Nitrilase Activity of Mutants Produced by 10-Liter Fermentation

*E. coli* seed cultures were grown in 500 mL LB media supplemented with 0.1 mg ampicillin per mL for 6–10 h ($OD_{550}$=1–2) at 30° C. with shaking (300 rpm) prior to inoculation of the fermentor.

Growth of nitrilase strains was in 14-L Braun Biostat C fermentors (B. Braun Biotech International Gmbh, Melsungen, Germany) using mineral medium with glucose, ammonia, and salts. IPTG (for FM5/pNM18 based strains) or lactose (for MG1655/pSW138 based strains) was used for induction.

Pre-sterilization fermentor media (7.5 L) is described in Table 2. Post-sterilization additions include filter sterilized trace elements (Table 3), 0.1 mg ampicillin per mL, 2 g casamino acids (Difco) per L, 4 g glucose per L, and 500 mL seed culture.

Fermentation set points are described in Table 4. NH₄OH (40% w/v) and $H_2PO_4$ (20% w/v) were used for pH control. The dissolved oxygen concentration was controlled at 25% of air saturation with the agitation to rise first with increase oxygen demand and the aeration to follow. The fermentation feed protocols used with IPTG induction and lactose induction are given in Tables 5 and 6, respectively. Glucose feed rates were reduced if glucose accumulated above 5 g/L. For FM5/pNM18 based strains, IPTG was added to 0.5 mM at $OD_{550}$=20–30. After 40–56 hrs cells were chilled to 5–10° C. and harvested by centrifugation. Nitrilase activity was determined as described (Example 2) and results are shown in Table 7.

TABLE 2

Fermentation media, pre-sterilization.

| | |
|---|---|
| (NH$_4$)$_2$SO$_4$ | 5.0 g/L |
| K$_2$HPO$_4$ | 4.0 g/L |
| KH$_2$PO$_4$ | 3.5 g/L |
| MgSO$_4$*7H$_2$O | 0.6 g/L |
| Na$_3$Citrate*2H$_2$O | 1.0 g/L |
| NZ Amine AS (Quest) | 2.5 g/L |
| Antifoam - Biospumex 153K | 0.25 ml/L |

TABLE 3

Fermentation trace elements

| | Concentration |
|---|---|
| Citric acid | 10 g/L |
| CaCl$_2$*2H$_2$O | 1.5 g/L |
| FeSO$_4$*7H$_2$O | 5 g/L |
| ZnSO$_4$*7H$_2$O | 0.39 g/L |
| CuSO$_4$*5H$_2$O | 0.38 g/L |
| CoCl$_2$*6H$_2$O | 0.2 g/L |
| MnCl$_2$*4H$_2$O | 0.3 g/L |

TABLE 4

Fermentation set points

| | Initial Set-Point | Minimum | Maximum |
|---|---|---|---|
| Stirrer (rpm) | 400 | 400 | 1000 |
| Airflow (slpm) | 2 | 2 | 10 |
| pH | 6.8 | 6.8 | 6.8 |
| Pressure (kPa) | 0.5 | 0.5 | 0.5 |
| DO | 25% | 25% | 25% |
| Temperature ° C. | 30 | 30 | 30 |

TABLE 5

Fermentation feed protocol used with IPTG induction

| EFT (hr) | Feed Rate (g/min) | Substrate |
|---|---|---|
| 0 | 0 | Glucose (batched) |
| 5 | 0.27 | Glucose (50% w/w) |

TABLE 6

Fermentation feed protocol used with lactose induction

| EFT (hr) | Feed Rate (g/min) | Substrate |
|---|---|---|
| 0 | 0 | Glucose (batched) |
| 5 | 0.27 | Glucose (50% w/w) |
| 14 | 1.3 | Lactose (25% w/w) |

TABLE 7

Nitrilase Activity for Mutants Grown in 10-Liter Fermentations

| Mutation (SEQ ID NO.) | E. coli Strain | Nitrilase Activity (GLA U/g dcw) | Fold Increase vs. Respective Control |
|---|---|---|---|
| None (SEQ ID NO: 6) | FM5/pNM18 (control) | 387 | NA |
| None (SEQ ID NO: 6) | MG1655/pSW138 (control) | 490 | NA |
| F168K (SEQ ID NO: 26) | FM5/pNM18-168K | 1250 | 3.2 |
| F168K (SEQ ID NO: 26) | MG1655/pSW138-168K | 1230 | 2.5 |
| F168M (SEQ ID NO: 28) | MG1655/pSW138-168M | 1261 | 2.6 |
| F168T (SEQ ID NO: 30) | FM5/pNM18-168T | 2152 | 5.6 |
| F168T (SEQ ID NO: 30) | MG1655/pSW138-168T | 837 | 1.7 |
| F168V (SEQ ID NO: 32) | MG1655/pSW138-168V | 1763 | 3.6 |
| L201Q (SEQ ID NO: 8) | FM5/pNM18-201Q | 2603 | 6.7 |
| L201Q (SEQ ID NO: 8) | MG1655/pSW138-201Q | 2410 | 4.9 |
| L201G (SEQ ID NO: 16) | FM5/pNM18-201G | 2985 | 7.7 |
| L201H (SEQ ID NO: 18) | FM5/pNM18-201H | 2322 | 6.0 |
| L201H (SEQ ID NO: 18) | MG1655/pSW138-201H | 1334 | 2.7 |
| L201K (SEQ ID NO: 20) | FM5/pNM18-201K | 4434 | 11.5 |
| L201N (SEQ ID NO: 22) | FM5/pNM18-201N | 2542 | 6.6 |
| L201N (SEQ ID NO: 22) | MG1655/pSW138-201N | 2695 | 5.5 |
| L201S (SEQ ID NO: 24) | FM5/pNM18-201S | 1463 | 3.8 |

EXAMPLE 10

Determination of Nitrilase Activity for *E. coli* TOP10/pNM18, *E. Coli* TOP10/pNM18-201A, *E. coli* TOP10/pNM18-201C, and *E. coli* TOP10/pNM128-201T (Shake Flask)

In duplicate, 10 mL of an overnight culture (LB+50 µg/mL ampicillin, 37° C. with shaking) was added to 200 mL (LB+50 ug/ml ampicillin+1 mM IPTG) and incubated at 37° C. with shaking for 4–5 hrs (final OD600 approximately 2.0). Cells were collected by centrifugation at 4° C. and stored frozen at −80° C.

To a 4-mL glass vial equipped with a magnetic stir bar was added 1.0 mL of 1.0 M glycolonitrile in water, and the vial and its contents equilibrated to 25° C. in a temperature controlled water bath. With stirring, 1.0 mL of 0.100 M potassium phosphate buffer (pH 7.0) containing 40–100 mg wet cell paste pre-equilibrated to 25° C. was added to the vial (final [GLN]=0.5M). Samples (0.100 mL) were taken at predetermined times and mixed with a solution comprised of 0.100 mL water, 0.020 mL of 6.0 N acetic acid and 0.200 mL of 0.20 M sodium butyrate in water (HPLC external standard). The resulting mixture was centrifuged and the resulting supernatant analyzed by HPLC for glycolic acid using a Supelco® (Sigma Aldrich Corp.) LC-18-DB column (15 cm×4.6 mm): mobile phase: aqueous 10 mM sodium acetate (NaOAc), 10 mM acetic acid (AcOH), 7.5% (v/v) methanol. The dry cell weight (dcw) of each cell paste was determined and used to calculate cell-specific nitrilase activity. Table 8 summarizes the increases in nitrilase activity for the nitrilase mutants compared to the native nitrilase.

TABLE 8

Nitrilase activity for mutants L201A, L201C, and L201T versus control (shake flasks).

| Mutation (SEQ ID NO.) | E. Coli strain | Nitrilase Activity (GLA U/g dcw) | Fold Increase in activity (vs. control) |
|---|---|---|---|
| None (SEQ ID NO: 6) | TOP10/pNM18 (Control) | 135 | NA |
| L201A (SEQ ID NO: 10) | TOP10/ pNM18-201A | 371 | 2.7 |
| L201C (SEQ ID NO: 12) | TOP10/ pNM18-201C | 289 | 2.1 |
| L201T (SEQ ID NO: 14) | TOP10/ pNM18-201T | 308 | 2.3 |

EXAMPLE 11

Preparation of Immobilized E. coli SS1001 (ATCC PTA-1177)

E. coli strain SS1001 (ATCC PTA-1177) is a transformed E. coli strain expressing the Acidovorax facilis 72W nitrilase (U.S. Pat. No. 6,870,038; herein incorporated by reference). The coding sequence of the recombinantly expressed (E. coli SS1001) nitrilase (SEQ ID NOs: 37–38) contains 2 minor sequence changes in comparison to the wild-type 72W nitrilase sequence (SEQ ID NO: 5). The start codon was changed from GTG to ATG to facilitate recombinant expression and an artifact was introduced during cloning that resulted in a single amino acid change near the C-terminal (Pro367 [CCA]→Ser [TCA];).

This strain was grown in a 10-L fermentation as previously described (see Example 8 of U.S. Ser. No. 10/919182), and the cell paste (glycolonitrile (GLN) was used in a process to convert GLN to glycolic acid (GLA) as follows.

E. coli SS1001 cells were first immobilized in carrageenan beads (the immobilized E. coli SS1001) according to the following procedure. With rapid stirring, 9 g of carrageenan (FMC GP911; FMC Corp., Philadelphia, Pa.) was slowly added to 231 g deionized distilled water at 50° C., the resulting mixture heated to 80° C. until carrageenan was completely dissolved, and the resulting solution cooled with stirring to 47° C. In a separate beaker equipped with stir bar, 75.9 g of frozen E. coli SS1001 cells (39.53% dcw) was added to 84.1 g of 0.35 M $Na_2HPO_4$ (pH 7.3) at ca. 25° C. and mixed until the cells were suspended, then a deoxyribonuclease I solution (10 µL of 12,500 U/mL DNase (Sigma Aldrich, St. Louis, Mo.)/100 mL of cell suspension) was added. The cell suspension was heated with stirring to 45–46° C. immediately before addition to carrageenan solution. With stirring, 160.0 g of E. coli SS1001 cell suspension at 47° C. was added to the carrageenan solution at 47° C., and the resulting cell/carrageenan suspension was pumped through an electrically-heated 20 gauge needle at 47° C. and dripped into 0.25 M $KHCO_3$ (pH=7.3) with stirring at room temperature (ca. 21–22° C.); the flow rate through the needle was set at 5–8 mL/min. The resulting beads were allowed to harden for 1 h with stirring, and were stored in 0.25 M $KHCO_3$ (pH 7.3). Chemical crosslinking of the beads was performed by addition of 0.5 g of 25% glutaraldehyde (GA) in water (Sigma M 752-07) to 20 g suspended in 48 mL of 0.25 M $KHCO_3$ (pH 7.3), and stirring for 1 h at room temperature. To the suspension of beads was then added 2.0 g of 12.5 wt % polyethylenimine (PEI, BASF LUPASOL PS; BASF Aktiengesellschaft, Ludwigshafen, Germany) in water followed by mixing for an additional 1 h at room temperature. The GA/PEI-crosslinked beads were stored in 1.0 M $NH_4HCO_3$ (pH 7.3) at 5° C.

Biocatalytic conversion of GLN to GLA was followed by HPLC. Aliquots (0.2 mL) of the reaction mixture were added to 0.01 mL 6 M HCl and 0.8 mL of 0.25 M n-propanol in water (HPLC external standard), and analyzed by HPLC (HPX 87H column (Bio-Rad, Hercules, Calif.), 30 cm×7.8 mm; 0.01 N $H_2SO_4$ mobile phase; 1.0 mL/min flow at 50° C.; 10 µL injection volume; refractive index (RI) detector, 20 min analysis time) for GLN and GLA. The nitrilase activity of the GA/PEI-crosslinked carrageenan/7.5% (dcw) E. coli SS1001 beads, was ~12 U/g beads, where 1 unit (U) converts 1 µmol of GLN to GLA in 1 min at 25° C.

EXAMPLE 12

Conversion of 1 M Glycolonitrile (GLN) to Ammonium Glycolate ($NH_4GLA$)

A 50-mL jacketed reaction vessel with overhead stirring was charged with 4 g E. coli SS1001 beads (Example 11), 13.73 mL deionized water, 0.4 mL 5 M $NH_4GLA$, and 1.87 mL GLN (ca. 52 wt % in water (TCI)), 0.89 M GLN final concentration, pH adjusted to pH 7.6, the mixture stirred at 25° C., and 0.2 mL aliquots were taken out to follow the reaction progress by HPLC. When all GLN was converted to $NH_4GLA$, product solution was decanted, 14.13 mL deionized water and 1.87 mL GLN were added to biocatalyst, pH adjusted to pH 7.6, and biocatalyst recycle was repeated. The initial rate of $NH_4GLA$ synthesis at the first biocatalyst recycle was 143 mM/h. Percent decrease in initial rate of $NH_4GLA$ synthesis vs. the recycle number are shown in Table 9 ("1 M").

EXAMPLE 13

Conversion of Approximately 3 M Glycolonitrile (GLN) to Ammonium Glycolate ($NH_4GLA$)

A 50-mL jacketed reaction vessel with overhead stirring was charged with 4 g E. coli SS1001 beads (Example 11), 6.39 mL deionized water, 4 mL 1 M $KHCO_3$, and 5.61 mL GLN (ca. 52 wt % in water (TCI)), 2.68 M GLN final concentration, pH was adjusted to pH 7.6, the mixture stirred at pH 25° C., and 0.2 mL aliquots were taken out to follow the reaction progress by HPLC. When all GLN was converted to $NH_4GLA$, product solution was decanted, 6.39 mL deionized water, 4 mL 1 M $KHCO_3$, and 5.61 mL GLN were added to biocatalyst, pH adjusted to pH 7.6, and biocatalyst recycle was repeated. The initial rate of $NH_4GLA$ synthesis at the first biocatalyst recycle was 207 mM/h. Percent decrease in initial rate of $NH_4GLA$ synthesis vs. the recycle number are shown in Table 9 ("3 M").

EXAMPLE 14

Addition of Approximately 3 M Glycolonitrile in Approximately 1 M Increments (1 M+1 M+1 M) to Yield Ammonium Glycolate ($NH_4GLA$)

A 50-mL jacketed reaction vessel with overhead stirring was charged with 4 g E. coli SS1001 beads (Example 11), 8.13 mL deionized water, 4 mL 1 M $KHCO_3$, and 1.87 mL GLN (ca. 52 wt % in water (TCl)), 0.89 M GLN, pH was adjusted to pH 7.6, the mixture stirred at 25° C., and 0.2 mL aliquots were taken out to follow the reaction progress by HPLC. When all GLN was converted to $NH_4GLA$, second portion of 1.87 mL GLN was added, pH was adjusted to pH 7.6, and when all GLN was consumed, the third portion of 1.87 mL GLN was added, pH adjusted to pH 7.6, and reaction completed yielding approximately 3 M $NH_4GLA$ solution. Product solution was decanted, 8.13 mL deionized water, 4 mL 1M $KHCO_3$, and 1.87 mL GLN were added to biocatalyst, pH adjusted to pH 7.6, GLN conversion proceeded to completion, and addition of GLN, water and buffer, pH adjustment, and completion of GLN conversion were repeated twice more to finish the recycle (step-wise conversion of GLN in three approximately 1M increments), and biocatalyst recycles were repeated. The initial rate of $NH_4GLA$ synthesis in the first 1 M GLN solution in a first recycle (three ~1 M portions of GLN per recycle) was 155 mM/h. Percent decrease in initial rate of $NH_4GLA$ synthesis vs. the recycle number are shown in Table 9 ("(1 M+1 M+1 M) =3 M").

EXAMPLE 15

Continuous Addition of Glycolonitrile (GLN) to 0.2 M GLN to Yield Ammonium Glycolate ($NH_4GLA$)

A 50-mL jacketed reaction vessel with overhead stirring was charged with 4 g *E. coli* SS1001 beads (Example 11), 8 mL deionized water, 4 mL 1 M $KHCO_3$, and 0.4 mL GLN (ca. 52 wt % in water (TCl)), pH was adjusted to pH 7.6, the mixture stirred at 25° C., GLN solution was continuously added up to 3 M GLN at a rate of GLN consumption to keep GLN concentration around 0.2 M, and 0.2 mL aliquots were taken out to follow the reaction progress by HPLC. When all GLN was converted to $NH_4GLA$, product solution was decanted, 8 mL deionized water, 4 mL 1 M $KHCO_3$, and 0.4 mL GLN were added to biocatalyst, pH adjusted to pH 7.6, and a new biocatalyst recycle was repeated with GLN addition up to 3 M GLN at a rate of GLN consumption. The initial rate of $NH_4GLA$ synthesis for the first biocatalyst recycle (3 M GLN total per recycle) was 144 mM/h. Percent decrease in initial rate of $NH_4GLA$ synthesis vs the recycle number are shown in Table 9 ("0.2 M Continuous").

Table 9. Percent decrease in initial rate of $NH_4GLA$ synthesis vs. recycle number at 3 M GLN, 1 M GLN, addition of 3 M GLN in three 1 M increments, and at continuous addition of GLN starting with 0.2 M GLN (nd=not determined).

| Reaction # (reactions 2–19 are recycle reactions with the same catalyst as in reaction 1) | 3 M GLN (% initial reaction rate) | 1 M GLN (% initial reaction rate) | (1 M + 1 M + 1 M) = 3 M GLN (% initial reaction rate) | 0.2 M Continuous Feed GLN (% initial reaction rate) |
|---|---|---|---|---|
| 1 | 100 | 100 | 100 | 100 |
| 2 | 62 | nd | 89 | 95 |
| 3 | nd | 75 | nd | 56 |
| 4 | 7 | 95 | 88 | 52 |
| 5 |  | nd | nd |  |
| 6 |  | 78 | nd |  |
| 7 |  | nd | 59 |  |
| 8 |  | 79 |  |  |
| 9 |  | nd |  |  |
| 10 |  | nd |  |  |
| 11 |  | nd |  |  |
| 12 |  | nd |  |  |
| 13 |  | 44 |  |  |
| 14 |  | nd |  |  |
| 15 |  | nd |  |  |
| 16 |  | nd |  |  |
| 17 |  | nd |  |  |
| 18 |  | 29 |  |  |
| 19 |  | 25 |  |  |

EXAMPLE 16

Preparation of GA/PEI-Crosslinked Carrageenan/*E. coli* FM5/pNM18-210A Beads Comprised of Different Levels of Cross-Linking The plasmid pNM18-210A, which expresses the nitrilase mutant 210Ala (SEQ ID NO: 34) from the plasmid pTrcHis2-TOPO® was used to transform *E. coli* FM5, to generate the strain identified as FM5/pNM18-210A. This strain was grown in a 10-ml fermentation as previously described (see Example 8 of U.S. Ser. No. 10/919182; herein incorporated by reference), and the cell paste was used in a process to convert GLN to glycolic acid (GLA) as follows.

*E. coli* FM5/pNM18-210A cells were first immobilized in carrageenan beads according to the following procedure. With rapid stirring, 12 g of carrageenan (FMC GP911) was slowly added to 228 g deionized distilled water at 50° C., the resulting mixture heated to 80° C. until carrageenan was completely dissolved, and the resulting solution cooled with stirring to 52° C. In a separate beaker equipped with stir bar, 74.9 g of frozen *E. coli* FM5/pNM18-210A cells (26.7% dcw) was added to 85.1 g of 0.35 M $Na_2HPO_4$ (pH 7.3) at ca. 25° C. and mixed until the cells were suspended, then a deoxyribonuclease I solution (10 μL of 12,500 U/mL DNase (Sigma)/100 mL of cell suspension) was added. The cell suspension was filtered consecutively through a 230 micron and 140 micron Nupro TF strainer element filter, and heated with stirring to 50° C. immediately before addition to carrageenan solution. With stirring, 160.0 g of *E. coli* FM5/pNM18-210A cell suspension at 50° C. was added to the carrageenan solution at 52° C., and the resulting cell/carrageenan suspension was pumped through an electrically-heated 20 gauge needle at 47° C. and dripped into 0.25 M $KHCO_3$ (pH=7.3) with stirring at room temperature (ca. 21–22° C.); the flow rate through the needle was set at 5–8 mL/min. The resulting beads were allowed to harden for 1 h with stirring, and were stored in 0.25 M $KHCO_3$ (pH 7.3). Chemical crosslinking of the beads was performed by either addition of 0.5 g (hereinafter referred to as "Biocatalyst 1") or 2.0 g (hereinafter referred to as "Biocatalyst 2") of 25% glutaraldehyde (GA) in water (Sigma M 752-07) to 20 g beads suspended in 48 mL of 0.25 M $KHCO_3$ (pH 7.3), and stirring for 1 h at room temperature. To the suspension of beads was then added either 2.0 g (Biocatalyst 1) or 4.0 g (Biocatalyst 2) of 12.5 wt % polyethylenimine (PEI, BASF LUPASOL PS) in water, and mixing for an additional 18 h at room temperature. The GA/PEI-crosslinked beads were stored in 1.0 M $NH_4HCO_3$ (pH 7.3) at 5° C.

Biocatalytic conversion of GLN to GLA was followed by HPLC. Aliquots (0.2 mL) of the reaction mixture were added to 0.01 mL 6 M HCl and 0.8 mL of 0.25 M n-propanol in water (HPLC external standard), and analyzed by HPLC (HPX 87H column, 30 cm×7.8 mm; 0.01 N $H_2SO_4$ mobile phase; 1.0 mL/min flow at 50° C.; 10 μL injection volume; RI detector, 20 min analysis time) for GLN and GLA. The nitrilase activity of the GA/PEI-crosslinked carrageenan/5% (dcw) E. coli FM5/pNM18-210A beads for both Biocatalyst 1 and Biocatalyst 2, was ~13 U/g beads, where 1 unit (U) converts 1 μmol of GLN to GLA in 1 min at 25° C.

EXAMPLE 17 (COMPARATIVE)

Conversion of Glycolonitrile (GLN) to Ammonium Glycolate ($NH_4GLA$) Without Additives in Air A 50-mL jacketed reaction vessel with overhead stirring was charged with 4 g Biocatalyst 1, 12.42 mL deionized water, 0.5 mL 4 M $NH_4GLA$, and 1.78 mL GLN (ca. 52 wt % in water (Fluka)), 1 M GLN final concentration, at pH 7.6, the mixture stirred at 25° C., and 0.2 mL aliquots were taken out to follow the reaction progress by HPLC. When all GLN was converted to $NH_4GLA$, second portion of 1.78 mL GLN was added, pH was adjusted to pH 7.6 with ammonium hydroxide, and when all GLN was consumed, the third portion of 1.78 mL GLN was added, pH adjusted to pH 7.6, and reaction completed yielding 3.1 M $NH_4GLA$ solution. Product solution was decanted, 12.42 mL deionized water and 1.78 mL GLN were added to biocatalyst, pH adjusted to pH 7.6, GLN conversion proceeded to completion, and addition of GLN, pH adjustment, and completion of GLN conversion were repeated twice more to finish the recycle (step-wise conversion of GLN in three 1M increments), and biocatalyst recycles were repeated. Percent decrease in initial rate of conversion of the first 1 M GLN solution in the recycle vs recycle number are shown in Table 10 (recycle reactions are reactions 2 through 8).

EXAMPLE 18

Conversion of Glycolonitrile (GLN) to Ammonium Glycolate ($NH_4GLA$) Without Additives in Oxygen-Free Environment A 50-mL jacketed reaction vessel with overhead stirring under nitrogen was charged with 4 g Biocatalyst 1, 12.42 mL deionized water, 0.5 mL 4 M $NH_4GLA$, and 1.78 mL GLN (ca. 52 wt % in water (Fluka)), 1 M GLN final concentration, at pH 7.6, the mixture stirred at 25° C., and 0.2 mL aliquots were taken out to follow the reaction progress by HPLC. When all GLN was converted to $NH_4GLA$, 1.78 ml GLN and 0.2 mL water were added, pH was adjusted to pH 7.6 with ammonium hydroxide, and when all GLN was consumed, the third portion of 1.78 mL GLN and 0.2 mL deionized water were added, pH adjusted to pH 7.6, and reaction completed, yielding 3.1 M $NH_4GLA$ solution. Product solution was decanted, 12.62 mL deionized water and 1.78 mL GLN were added to biocatalyst, pH adjusted to pH 7.6, GLN conversion proceeded to completion, and addition of 1.78 mL GLN and 0.2 mL deionized water, pH adjustment, conversion of GLN to completion were repeated twice more to finish the recycle (step-wise conversion of GLN in three increments), and biocatalyst recycles were repeated. The percent decrease in the initial rate for conversion of the first 1 M GLN solution in a recycle reaction vs the recycle reaction number are shown in Table 10 (recycle reactions are reactions 2 through 8).

EXAMPLE 19

Converting Glycolonitrile (GLN) to Ammonium Glvcolate ($NH_4GLA$) in the Presence of Thiosulfate or Dithionite in Oxygen-Free Environment Biocatalyst recycles were performed as described in Example 18 except instead of 12.42 mL of deionized water, 12.22 mL of deionized water and 0.2 mL of 1 M solution of additive (potassium thiosulfate, $K_2S_2O_3$ or sodium dithionite, $K_2S_2O_4$,) in water were added to start the recycle, and instead of 0.2 mL water, 0.2 mL 1 M solution of additive in water was added to reaction vessel along with each addition of 1.78 mL GLN. Percent decrease in initial rate for conversion of the first 1 M GLN solution in a recycle vs the recycle number are shown in Table 10 (recycle reactions are reactions 2 through 8).

Table 10. Percent decrease in initial rate of $NH_4GLA$ synthesis for conversion of the first 1 M GLN solution in a recycle reaction (3 M GLN total per recycle) vs the recycle reaction number after addition of thiosulfate or dithionite to the reaction under nitrogen, or for GLN conversion without additives under nitrogen or in air (nd=not determined).

| Reaction # | $K_2S_2O_3/N_2$ (% initial reaction rate) | $Na_2S_2O_4/N_2$ (% initial reaction rate) | control/$N_2$ (% initial reaction rate) | control/air (% initial reaction rate) |
|---|---|---|---|---|
| 1 | 100 | 100 | 100 | 100 |
| 2 | 114 | 96 | 77 | 116 |
| 3 | 104 | 91 | 97 | 81 |
| 4 | 101 | 76 | 112 | nd |
| 5 | 104 | 72 | 74 | 66 |
| 6 | 102 | 79 | 74 | nd |
| 7 | 86 | 64 | 63 | 7 |
| 8 | 92 | 74 | 68 | |

EXAMPLE 20

Conversion of Glycolonitrile (GLN) to Ammonium Glycolate ($NH_4GLA$) Without Additives in Air at pH 6.0

A 50-mL jacketed reaction vessel with overhead stirring was charged with 4 g Biocatalyst 1, 12.42 mL deionized water, 0.5 mL 4 M $NH_4GLA$, and 1.78 mL GLN (ca. 52 wt % in water (Fluka)), 1 M GLN final concentration, at pH 6.0, the mixture stirred at 25° C., and 0.2 mL aliquots were taken out to follow the reaction progress by HPLC. When all GLN was converted to $NH_4GLA$, a second portion of 1.78 mL GLN was added, pH was adjusted to pH 6.0 with ammonium hydroxide, and when all GLN was consumed, a the third portion of 1.78 mL GLN was added, pH adjusted to pH 6.0, and the reaction completed yielding 3.1 M $NH_4GLA$ solution. Product solution was decanted, 12.42 mL deionized water and 1.78 mL GLN were added to biocatalyst, pH adjusted to pH 6.0, GLN conversion proceeded to completion, and addition of GLN, pH adjustment, and completion of GLN conversion were repeated twice more to finish the recycle reaction (step-wise conversion of GLN in three increments), and biocatalyst recycles were repeated. Decrease in initial rate of conversion of the first 1 M GLN solution in the recycle reaction vs recycle reaction number for Biocatalyst 1 are shown in Table 11 (recycle reactions are reactions 2 through 4)

Table 11. Percent decrease in initial rate of $NH_4GLA$ synthesis for conversion of first 1 M GLN solution in a recycle reaction (3 M GLN total per recycle) vs the recycle reaction number at pH 6.0 for Biocatalyst 1.

| Reaction # | Biocatalyst 1 (E. coli FM5/pNM18-210A) pH 6.0 (% initial reaction rate) |
|---|---|
| 1 | 100 |
| 2 | 71 |
| 3 | 50 |
| 4 | 24 |

EXAMPLE 21

Conversion of Glycolonitrile (GLN) to Ammonium Glycolate ($NH_4GLA$) Using Immobilized E. coli MG1655/pSW138 Cells Expressing A. facilis 72W Nitrilase at Various Reaction pHs A 50-mL jacketed reaction vessel equipped with overhead stirring and temperature control was charged with 4 g of GA/PEI-crosslinked carrageenan beads (prepared using the process as described in Example 11), washed twice for 15 min with 72 mL of 0.1 M $NH_4GLA$ (pH 7.0)) containing 5% (dcw) E. coli MG1655/pSW138 expressing the A. facilis 72W nitrilase (SEQ ID NO: 6). To the vessel was then added 10.88 g of distilled water and 2.98 mL 4.0 M $NH_4GLA$ (pH 7.5), the appropriate amounts of either 70 wt % glycolic acid (GLA) (Aldrich) or 1:4 dilution of ammonium hydroxide (28–30 wt %) in water (Table 12), and the reaction vessel was flushed with nitrogen. The mixture was stirred at 25° C. and 2.15 mL of 49.88 wt % glycolonitrile (GLN) in water (2.25 g, 19.6 mmol (Fluka)) was added to yield 1 M GLN at pH 4.0, 4.7, 5.5, 6.7, or 7.5 (Table 13).

Four 0.100-mL reaction samples were removed at predetermined times after the GLN addition and analyzed by HPLC to determine the initial reaction rate. The initial reaction rates as an average of rates in duplicate runs at each pH are listed in Table 13.

TABLE 12

Amounts of 70 wt % glycolic acid in water (GLA) or 1:4 dilution of 28–30 wt % ammonium hydroxide ($NH_4OH$) in water used to prepare reaction solutions of indicated pH.

| pH | Aqueous GLA (mL) | Aqueous $NH_4OH$ (mL) |
|---|---|---|
| 4.0 | 0.700 | 0 |
| 4.7 | 0.150 | 0 |
| 5.5 | 0 | 0 |
| 6.7 | 0 | 0.050 |
| 7.5 | 0 | 0.100 |

TABLE 13

Initial reaction rate for conversion of GLN to $NH_4GLA$ using immobilized E. coli MG1655/pSW138 cells expressing A. facilis 72W nitrilase at various pHs (average of duplicate reactions).

| pH | Initial Reaction Rate (mM GLA/h) |
|---|---|
| 4.0 | 0 |
| 4.7 | 68 |
| 5.5 | 347 |
| 6.7 | 354 |
| 7.5 | 351 |

EXAMPLE 22

Hydrolysis of Glycolonitrile to Ammonium Glycolate Using Immobilized E. coli FM5/pNM18 Expressing A. facilis 72W Nitrilase in the Presence or in the Absence of Hydrogen Cyanide (HCN)

A 50-mL jacketed reaction vessel equipped with overhead stirring and temperature control was charged with 4 g of GA/PEI-crosslinked carrageenan beads (prepared using the process described in Example 11), washed twice for 15 min with 72 mL of 0.1 M $NH_4GLA$ (pH 7.5)) containing 5% (dcw) E. coli FM5/pNM18 expressing the A. facilis 72W nitrilase (SEQ ID NO: 6). To the vessel was then added 10.9 g of distilled water and 3.0 mL 4.0 M $NH_4GLA$ (pH 7.5), and the reaction vessel was flushed with nitrogen. The mixture was stirred at 25° C. and an aliquot of 1.777 mL of 60.51 wt % glycolonitrile (GLN) in water (1.885 g, 20.0 mmol (Fluka, redistilled)) with or without 0.063 mL 50 wt % HCN in water (0.054 g, 1 mmol) was first added, followed immediately by addition of 0.320 mL of a 1:16 dilution of ammonium hydroxide (28–30 wt %) in water. Four 0.100-mL reaction samples were removed at predetermined times after the first GLN addition and analyzed by HPLC to determine the initial reaction rate. At completion of GLN conversion, the second aliquot each of GLN and ammonium hydroxide was added to maintain the concentration of GLN at $\leq 1$ M and pH within a range of 7.0–7.5, and after the GLN conversion was completed, the third aliquot of each of GLN and ammonium hydroxide was added. At completion of the reaction, there was 100% conversion of GLN to produce glycolic acid (as the ammonium salt) in >99% yield, and the concentration of ammonium glycolate produced from added GLN was approximately 2.5 M (3.0 M total ammonium glycolate, including initial ammonium glycolate buffer, in a final reaction volume of ca. 23.7 mL).

At the end of the first reaction, the aqueous product mixture was decanted from the catalyst (under nitrogen), to the reaction vessel then added 13.9 mL of distilled, deionized water, and a second reaction was performed at 25° C. by the addition of aliquots of aqueous GLN and ammonium hydroxide as described immediately above. The initial reaction rates for consecutive batch reactions with catalyst recycle are listed in Table 14 (recycle reactions are reactions 2 through 9).

TABLE 14

Initial reaction rate for conversion of GLN to GLA in consecutive batch reactions with catalyst recycle using immobilized E. coli FM5/pNM18 expressing A. facilis 72W nitrilase in the presence and in the absence of HCN.

| Reaction # | HCN (mM GLA/h) | No additive (mM GLA/h) |
|---|---|---|
| 1 | 260 | 183 |
| 2 | 289 | 269 |
| 3 | 291 | 218 |
| 4 | 271 | 222 |
| 5 | 238 | 235 |
| 6 | 257 | 240 |
| 7 | 250 | 208 |
| 8 | 239 | 177 |
| 9 | 213 | 188 |

EXAMPLE 24

Affect of Addition of Either Formaldehyde or Hydrogen Cyanide in Consecutive Catch Reactions for Hydrolysis of Glycolonitrile to Ammonium Glycolate Using Immobilized *E. coli* FM5/pNM18 Expressing *A. facilis* 72W Nitrilase The reactions were run, characterized, and the biocatalyst was recycled as described in Example 23 for reactions without addition of HCN, except that each aliquot of 1.777 mL of 60.51 wt % glycolonitrile (GLN) in water (1.885 g, 20.0 mmol (Fluka, redistilled)) contained either 0.074 mL 37 wt % HCHO in water (0.081 g, 1 mmol) (recycles 1, 2, 3, and 6) or 0.063 mL 50 wt % HCN in water (0.054 g, 1 mmol) (recycles 4, 5, and 7) (Table 15). The data for reactions without addition of HCHO or HCN are repeated from Table 14 for comparison.

TABLE 15

Initial reaction rate for conversion of GLN to GLA in consecutive batch reactions with catalyst recycle using immobilized *E. coli* FM5/pNM18 expressing *A. facilis* 72W nitrilase at addition of HCHO (reactions 1, 2, 3, and 6) or addition of HCN (reactions 4, 5, and 7) to the same reaction series, and without addition of HCHO or HCN.

| Reaction # | HCHO Initial rate (mM GLA/h) | HCN Initial rate (mM GLA/h) | No additives initial rate (mM GLA/h) |
|---|---|---|---|
| 1 | 192 |  | 183 |
| 2 | 152 |  | 269 |
| 3 | 90 |  | 218 |
| 4 |  | 234 | 222 |
| 5 |  | 218 | 235 |
| 6 | 113 |  | 240 |
| 7 |  | 219 | 208 |
| 8 |  |  | 177 |
| 9 |  |  | 188 |

EXAMPLE 25

Hydrolysis of Glycolonitrile to Ammonium Glycolate Using *E. coli* FM5/pNM18-L201Q Cells Expressing *A. facilis* 72W Nitrilase Mutant L201 Q A 50-mL centrifuge tube was charged with 1.25 mL uniform suspension obtained using 6 g of *E. coli* FM5/pNM18-L201Q expressing the *A. facilis* 72W nitrilase mutant L201Q (SEQ ID NO: 8) and 7.54 mL 0.35 M Na$_2$HPO$_4$ (pH 7.5), 35 ml 0.35 M Na$_2$HPO$_4$ (pH 7.5) was added, the tube was centrifuged at 5000 rpm for 20 min, the supernatant was carefully and fully removed from cell paste, and 935 mg of the centrifuged cell paste was transferred to a 150-mL jacketed reaction vessel equipped with overhead stirring and temperature control. To the vessel was then added 52.54 mL of 0.3 M NH$_4$GLA (pH 7.5), 7.88 mL 4.0 M NH$_4$GLA (pH 7.5), and 9.63 mL of distilled water, and the reaction vessel was flushed with nitrogen. The mixture was stirred at 25° C., 7.82 mL of 54.61 wt % glycolonitrile (GLN) in water (8.18 g, 78.3 mmol (Fluka)) was added, and pH was adjusted to pH 7.5 by a 1:4 dilution of ammonium hydroxide (28–30 wt %) in water. To determine the initial reaction rates, four 0.050-mL reaction samples were removed at predetermined times after the first GLN addition, added to assay mix (0.025 mL of 6.0 N HCl and 0.800 mL 0.18 M n-propanol), vortexed, centrifuged at 12,000 rpm for 6 min, and supernate was analyzed by HPLC as described in Example 2. At completion of GLN conversion, the second aliquot of GLN was added, pH was adjusted to 7.5 with ammonium hydroxide, and after the GLN conversion was completed, the third GLN aliquot was added and pH was adjusted to pH 7.5. At completion of the reaction, there was 100% conversion of GLN to produce glycolic acid (as the ammonium salt) in >99% yield, and the concentration of ammonium glycolate produced from added GLN was approximately 2.5 M (2.9 M total ammonium glycolate, including initial ammonium glycolate buffer, in a final reaction volume of ca. 94.05 mL).

At the end of the first reaction, the aqueous product mixture was centrifuged from the cell pastes (5000 rpm, 20 min), the cell paste was weighed and transferred back to the reaction vessel. To the vessel then added 52.54 mL 0.3 M NH$_4$GLA (pH 7.5), 7.88 mL 4.0 M NH$_4$GLA (pH 7.5) and 9.63 mL of distilled water, the reaction vessel was flushed with nitrogen, and a second reaction was performed at 25° C. by the addition of aliquots of aqueous GLN and ammonium hydroxide as described immediately above. The weight of cell paste recovered after reaction 4 by centrifugation of reaction solution as described above was 964 mg, The initial reaction rates for consecutive batch reactions with catalyst recycle are listed in Table 16 (recycle reactions are reactions 2 through 4).

TABLE 16

Initial reaction rate for conversion of GLN to GLA in consecutive batch reactions with catalyst recycle using *E. coli* FM5/pNM18-L201Q cell paste expressing *A. facilis* 72W nitrilase mutant L201Q.

| Reaction # | Initial Rate (mM GLA/h) |
|---|---|
| 1 | 180 |
| 2 | 157 |
| 3 | 147 |
| 4 | 133 |

EXAMPLE 26

Hydrolysis of Glycolonitrile to Ammonium Glycolate Using Immobilized *E. coli* MG1655/pSW138 Transformants Expressing *A. facilis* 72W Nitrilase or *A. facilis* 72W Nitrilase Mutants A 50-mL jacketed reaction vessel equipped with overhead stirring and temperature control was charged with 8 g of GA/PEI-crosslinked carrageenan beads (prepared using the process as described in Example 11), washed twice for 15 min with 72 mL of 0.1M NH$_4$GLA (pH 7.0)) containing 5% (dcw) *E. coli* MG1655/pSW138 transformant expressing the *A. facilis* 72W nitrilase (SEQ ID NO: 6), or the A. facilis 72W nitrilase mutants F168V (SEQ ID NO: 32), F168M (SEQ ID NO: 28), F168K (SEQ ID NO: 26), F168T (SEQ ID NO: 30), and L201Q (SEQ ID NO: 8). To the vessel was then added 14.632 g of distilled water and 6.0 mL 4.0 M NH$_4$GLA (pH 7.0), and the reaction vessel flushed with nitrogen. The mixture was stirred at 25° C. while programmable syringe pumps were used to add eight aliquots of 1.08 mL of 59 wt % glycolonitrile (GLN) in water (1.14 g, 12.0 mmol (Fluka, redistilled)) and 0.288 mL of a 1:16 dilution of ammonium hydroxide (28–30 wt %) in water (2.304 mL total); one aliquot each of GLN and ammonium hydroxide was added simultaneously every 2 h to maintain the concentration of GLN at $\leq 400$ mM and the pH within a range of 6.5–7.5. Four 0.050-mL reaction samples were removed at predetermined times after the first GLN addition and analyzed by HPLC to determine the initial reaction rate. At completion of the reaction, there was 100% conversion of GLN to produce glycolic acid (as the ammonium salt) in >99% yield, and the concentration of ammonium glycolate produced from added GLN was approximately 2.4 M (3.0 M total ammonium glycolate, including initial ammonium glycolate buffer, in a final reaction volume of ca. 39.5 mL).

At the end of the first reaction, the aqueous product mixture was decanted from the catalyst (under nitrogen), leaving ca. 10.3 g of a mixture of immobilized cell catalyst (8.0 g) and remaining product mixture (ca. 2.3 g). To the reaction vessel then added 18.3 mL of distilled, deionized water, and a second reaction was performed at 25° C. by the addition of aliquots of aqueous GLN and ammonium hydroxide as described immediately above. The initial reaction rates for consecutive batch reactions with catalyst recycle are listed in Table 17 (recycle reactions are reactions 2 through 55).

The catalyst productivity (total grams GLA produced/ gram dry cell weight (dcw) enzyme catalyst) was calculated for each nitrilase from the total number of consecutive batch reactions with catalyst recycle that resulted in 100% conversion of glycolonitrile. The catalyst productivity for each enzyme catalyst was: *E. coli* MG1655/pSW138-F168V, 1001 g GLA/g dcw (55 consecutive batch reactions); *E. coli* MG1655/pSW138-F168M, 473 g GLA/g dcw (26 consecutive batch reactions); *E. coli* MG1655/pSW138-F168K, 473 g GLA/g dcw (26 consecutive batch reactions); *E. coli* MG1655/pSW138-F168T, 364 g GLA/g dcw (20 consecutive batch reactions); *E. coli* MG1655/pSW138-L201Q, 346 g GLA/g dcw (19 consecutive batch reactions); *E. coli* MG1655/pSW138, 182 g GLA/g dcw (10 consecutive batch reactions).

TABLE 17

Initial reaction rates for conversion of GLN to GLA in consecutive batch reactions with catalyst recycle using immobilized *E. coli* MG1655/pSW138 transformants expressing *A. facilis* 72W nitrilase or *A. facilis* 72W nitrilase mutants (nd = not determined).

| Rxn # | MG1655/ pSW138- F168V (mM GLA/h) | MG1655/ pSW138- F168M (mM GLA/h) | MG1655/ pSW138- F168K (mM GLA/h) | MG1655/ pSW138- F168T (mM GLA/h) | MG1655/ pSW138- L201Q (mM GLA/h) | MG1655/ pSW138 (mM GLA/h) |
|---|---|---|---|---|---|---|
| 1 | 1050 | 658 | 652 | 423 | 757 | 330 |
| 2 | 698 | 538 | 560 | 389 | 611 | 220 |
| 3 | 719 | 488 | 394 | 453 | 497 | 207 |
| 4 | 654 | 452 | nd | 311 | 435 | 174 |
| 5 | 719 | 441 | 322 | 494 | 549 | 193 |
| 6 | 559 | 378 | 439 | 456 | 416 | 171 |
| 7 | 531 | 258 | 435 | 408 | 482 | 207 |
| 8 | 634 | 407 | 209 | 378 | 453 | 141 |
| 9 | 586 | 340 | 294 | 502 | 653 | 123 |
| 10 | 609 | 303 | 420 | 468 | 537 | 92 |
| 11 | 432 | 313 | 426 | 428 | 443 | 76 |
| 12 | 397 | 560 | 361 | 481 | 388 | |
| 13 | 318 | 430 | 422 | 391 | 359 | |
| 14 | 449 | 391 | 387 | 255 | 302 | |
| 15 | 259 | 304 | 444 | 260 | 246 | |
| 16 | 370 | 308 | 452 | 362 | 377 | |
| 17 | 401 | 330 | 448 | 318 | 307 | |
| 18 | 579 | 384 | nd | 299 | 252 | |
| 19 | 392 | 253 | nd | 233 | 282 | |
| 20 | nd | nd | 487 | 372 | 209 | |
| 21 | nd | nd | nd | nd | nd | |
| 22 | 356 | 247 | nd | 144 | 116 | |
| 23 | nd | nd | 355 | 165 | 129 | |
| 24 | nd | nd | 300 | | | |
| 25 | 402 | 219 | 252 | | | |
| 26 | 407 | 134 | 270 | | | |
| 27 | 390 | 87 | 141 | | | |
| 28 | 280 | 45 | | | | |
| 29 | 297 | 24 | | | | |
| 30 | 277 | | | | | |
| 31 | 300 | | | | | |
| 32 | 325 | | | | | |
| 33 | 344 | | | | | |
| 34 | 340 | | | | | |
| 35 | 317 | | | | | |
| 36 | 277 | | | | | |
| 37 | 191 | | | | | |
| 38 | 279 | | | | | |
| 39 | 325 | | | | | |
| 40 | 372 | | | | | |
| 41 | 257 | | | | | |
| 42 | 329 | | | | | |
| 43 | 530 | | | | | |
| 44 | 235 | | | | | |
| 45 | 291 | | | | | |
| 46 | 339 | | | | | |
| 47 | 226 | | | | | |
| 48 | 309 | | | | | |

TABLE 17-continued

Initial reaction rates for conversion of GLN to GLA in consecutive batch reactions with catalyst recycle using immobilized E. coli MG1655/pSW138 transformants expressing A. facilis 72W nitrilase or A. facilis 72W nitrilase mutants (nd = not determined).

| Rxn # | MG1655/ pSW138- F168V (mM GLA/h) | MG1655/ pSW138- F168M (mM GLA/h) | MG1655/ pSW138- F168K (mM GLA/h) | MG1655/ pSW138- F168T (mM GLA/h) | MG1655/ pSW138- L201Q (mM GLA/h) | MG1655/ pSW138 (mM GLA/h) |
|---|---|---|---|---|---|---|
| 49 | 406 | | | | | |
| 50 | 456 | | | | | |
| 51 | 242 | | | | | |
| 52 | 168 | | | | | |
| 53 | 217 | | | | | |
| 54 | 220 | | | | | |
| 55 | 59 | | | | | |

EXAMPLE 27

Characterization of Ammonium Glycolate Obtained by Conversion of GLN Using Immobilized E. coli MG1655/pSW138 Transformant Expressing A. facilis 72W Nitrilase Mutant F168V To evaluate composition of product solutions obtained by GLN (Fluka, redistilled) hydrolysis with immobilized MG1655/pSW138-F168V biocatalyst (see Example 26, Table 17), the product solutions produced in reactions 5, 10, and 38 were characterized by HPLC and $^1$H NMR spectroscopy. Concentration of glycolate determined by HPLC was 3.1 M. Quantitative $^1$H NMR spectra were obtained using a Varian Unity Inova spectrometer (Varian, Inc., Palo Alto, Calif.) operating at 500 MHz. Samples were prepared by adding 150 μL of the reaction product along with 400 μL of $D_2O$ to a 5 mm NMR tube.

$^1$H NMR spectra were acquired using a spectral width of 6000 Hz with the transmitter located at 5 ppm, and a 90-degree pulse (5.9 microseconds at a transmitter power of 49 db). An acquisition time of 4 seconds was used which led to a total data size of 48,000 points. The longest $^1$H $T_1$ (8 sec) was associated with the methanol $CH_3$ protons, and the total delay time prior to acquisition was therefore set to 50 seconds (i.e., more than 5 times the methanol $CH_3$ $T_1$). This pre-delay time was split between a simple delay time ("d1") and a solvent saturation pulse of 30 seconds applied on resonance for residual water at a transmitter power of –6 db. Signal averaging of 32 scans was preceded by 4 steady-state ("dummy") scans to give a total experiment time of approximately 32 minutes. Assignments were obtained by comparison of $^1$H NMR chemical shifts with those obtained in previous 2-dimensional NMR correlation experiments, and by spiking experiments.

The impurities observed in the ammonium glycolate product solutions by $^1$H NMR spectroscopy were categorized, on the basis of their functional groups, into the following functional group categories: formaldehyde-derived, formic acid-derived, methanol-derived, and methyl-derived. Integrated peak areas of proton signals for each of the categories were assigned as follows: two protons were assigned to formaldehyde functionality, one proton assigned to formic acid functionality, three protons assigned to methanol functionality, and three protons assigned to methyl functionality. Integrated peak areas for ammonium glycolate were divided by 2 (the number of ammonium glycolate protons) and assigned a value of 100%. Integrated peak areas of the protons observed for each of the impurity functional group categories were divided by the number of corresponding protons (see above), and the resulting integrated peak area divided by the integrated peak area of one glycolate proton present in the sample to determine the percent concentration of the impurity relative to the concentration of ammonium glycolate present. The yield of ammonium glycolate (based on 100% conversion of GLN) and the % purity of ammonium glycolate (based on relative concentration of glycolate and total impurities) is listed in Table 18.

TABLE 18

Yield and purity of ammonium glycolate produced by the conversion of GLN using immobilized E. coli MG1655/pSW138 transformant expressing A. facilis 72W nitrilase mutant F168V.

| Reaction # | Ammonium glycolate yield (%) | Ammonium glycolate purity (%) |
|---|---|---|
| Example 26, reaction 5 | 99% | 98.5 |
| Example 26, reaction 10 | 99% | 98.5 |
| Example 26, reaction 38 | 99% | 98.8 |

EXAMPLE 28

Isolation of Glycolic Acid from Ammonium Glycolate by Fixed-Bed Ion Exchange Chromatography GLN synthesized from hydrogen cyanide and formaldehyde as described in Examples 4–8 of copending U.S. provisional application 60/638127 (herein incorporated by reference), was converted to ammonium glycolate as described in Example 12, without additives (except that the reaction volume was scaled-up 18-fold), and fixed-bed ion exchange was used to convert the ammonium glycolate product solution to glycolic acid.

A 5 cm ID×60 cm borosilicate glass column (Spectrum-Chromatography) fitted with Teflone® PTFE end caps and Dowex® G-26 strongly acidic cation resin in the $H^+$ form (Dow Chemical Co) were used. A 5-gallon polypropylene feed jug was used to supply ultrapure water (18+MΩ, produced by a Sybron-Barnstead Nanopure II unit) to the column feed pump (Cole-Parmer variable-speed diaphragm pump with all-Teflon® head) for resin pre- and post-rinsing. The jug was nitrogen-purged at all times to prevent absorption of atmospheric $CO_2$. After pre-rinsing the filled column (initial height=23", bed volume=1147 mL) with ultrapure water to an effluent of >5 MΩ, the ammonium glycolate (1.3 liters (1428 g), pH=7.09) was pumped through the bed upflow at 40 mL; when the glycolate was depleted, the unit was switched back to ultrapure water pumping at the same rate to continue pushing the feed material through the bed. During the run the column effluent was captured continuously in 50 mL increments using pre-rinsed HDPP (high density polypropylene) sample bottles; a total of thirty-eight 50-mL samples of effluent were taken continuously and were analyzed for pH (pH meter), glycolate concentration (HPLC), and ammonium ion content (via ion chromatography).

Determination of ammonium ion content was done using Dionex IP25 pump equipped with CD20 conductivity detector and Dionex CS17 column (3–11 mM Methane Sulfonic Acid, 1.0 mL/min, suppressed with a Dionex CSRS ultra set to 100 microamp, 1.0 mL/min, 100 microliters sample loop), and cation 3–11 mM CS17 method was applied for the analysis.

Fractions 12 to 23 were combined (600 mL total), stirred overnight with 5 g fresh Dowex® G-26 resin (pre-rinsed 3 times with 45 mL of deionized water for 20 min), 651 g of glycolic acid solution was collected by filtration. The solution was concentrated by rotary evaporation to produce 70 wt % glycolic acid (140 g product). Analysis of the 70 wt % glycolic acid for impurities indicated the purity of glycolic acid was greater than 99.9%.

---

What is claimed is:

1. A process to produce glycolic acid from glycolonitrile comprising:
   a) contacting glycolonitrile in a suitable aqueous reaction mixture with an enzyme catalyst comprising a polypeptide having nitrilase activity, said polypeptide having an amino acid sequence of SEQ ID NO: 6 with an amino acid substitution selected from the group consisting of:
   1) a substitution at amino acid residue 168 with lysine, methionine, threonine or valine; and
   2) a substitution at amino acid residue 201 with glutamine, glycine, histidine, lysine, asparagine, serine, alanine, cysteine, or threonine;
   whereby glycolic acid is produced; and
   b) recovering the glycolic acid produced in (a) in the form of a salt or acid; wherein said enzyme catalyst provides at least a 1.5-fold increase in nitrilase activity relative to the nitrilase activity of the *Acidovorax facilis* 72W nitrilase when converting glycolonitrile to glycolic acid under identical reaction conditions.

2. The process of claim 1 wherein said amino acid sequence is selected from the group consisting of SEQ ID NOs: 8, 10, 12, 14, 16, 18, 20, 22, 24, 26, 28, 30, and 32.

3. The process of claim 1 wherein the enzyme catalyst is an improved nitrilase catalyst providing at least about a 2-fold improvement in nitrilase activity when converting glycolonitrile to glycolic acid relative to the activity of the *A. facilis* 72W (ATCC 55746) nitrilase under identical reaction conditions.

4. The process of claim 2 wherein the enzyme catalyst is an improved nitrilase catalyst providing at least about a 4-fold improvement in nitrilase activity when converting glycolonitrile to glycolic acid relative to the activity of the *A. facilis* 72W (ATCC 55746) nitrilase under identical reaction conditions.

5. The process of claim 1 wherein the enzyme catalyst is in the form of whole microbial cells, permeabilized microbial cells, one or more cell components of a microbial cell extract, partially purified enzyme, or purified enzyme.

6. The process of claim 5 wherein said whole microbial cell is a transformed microbial host cell recombinantly expressing said polypeptide.

7. The process of claim 5 wherein the transformed microbial host cell is selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Zygosaccharomyces* sp., *Pichia* sp., *Kluyveromyces* sp., *Candida* sp., *Hansenula* sp., *Dunaliella* sp., *Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp.

8. The process of claim 7 wherein the transformed microbial host cell is *Escherichia coli*.

9. The process of claim 8 wherein the transformed microbial host cell is an *Escherichia coli* strain selected from the group consisting of *E. coli* MG1655 having international depository number ATCC 47076 and *E. coli* FM5 having international depository number ATCC 53911.

10. The process of any one of claims 1–9 wherein the enzyme catalyst is immobilized in or on a soluble or insoluble support.

11. The process of claim 1 wherein the concentration of ammonium glycolate produced in the aqueous reaction mixture is about 0.02 wt % to about 90 wt %

12. The process of claim 11 wherein the concentration of ammonium glycolate produced in the aqueous reaction mixture is about 0.02 wt % to about 40 wt %.

13. The process of claim 10 wherein the glycolonitrile concentration in the aqueous reaction mixture is in the range of about 5 mM to about 1 M.

14. The process of claim 13 wherein the glycolonitrile concentration in the aqueous reaction mixture is maintained by continuous or aliquot addition.

15. The process of claim 1 wherein the pH in the aqueous reaction mixture is maintained between about 5.5 and about 7.7.

16. The process of claim 1 wherein the enzymatic conversion of glycolonitrile to glycolic acid occurs under substantially oxygen free conditions.

17. The process of claim 1 wherein the aqueous reaction mixture further comprises a stabilizer selected form the group consisting of potassium thiosulfate and sodium dithionite at a concentration of less than 5 wt %.

18. The process of claim 1 wherein the enzyme catalyst is a recycled enzyme catalyst.

19. The process of claim 1 wherein the enzyme catalyst provides a catalyst productivity of at least 300 grams of glycolic acid per gram of dry cell weight enzyme catalyst.

20. The process of claim 19 wherein the enzyme catalyst provides a catalyst productivity of at least 450 grams of glycolic acid per gram of dry cell weight enzyme catalyst.

21. The process of claim 20 wherein the enzyme catalyst provides a catalyst productivity of at least 1000 grams of glycolic acid per gram of dry cell weight enzyme catalyst.

* * * * *